(12) United States Patent
Stevens et al.

(10) Patent No.: US 7,303,869 B2
(45) Date of Patent: *Dec. 4, 2007

(54) SOLID-PHASE REACTIONS

(75) Inventors: Priscilla Wilkins Stevens, Evanston, IL (US); David Kelso, Wilmette, IL (US); Victor Lyamichev, Madison, WI (US); Jeff Hall, Madison, WI (US); Bruce P. Neri, Madison, WI (US); Robert W. Kwiatkowski, Jr., Verona, WI (US); Lloyd M. Smith, Madison, WI (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/269,222

(22) Filed: Oct. 11, 2002

(65) Prior Publication Data

US 2003/0143585 A1 Jul. 31, 2003

Related U.S. Application Data

(60) Provisional application No. 60/306,010, filed on Jul. 17, 2001, provisional application No. 60/328,947, filed on Oct. 12, 2001.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/23.1; 536/24.3

(58) Field of Classification Search .............. 435/6, 435/91.2, 91.1; 536/24.32, 24.33, 253; 422/68.1
See application file for complete search history.

(56) References Cited

U.S. PATENT DOCUMENTS

| | | | |
|---|---|---|---|
| 5,846,717 A | 12/1998 | Brow et al. ............... | 435/6 |
| 5,985,557 A | 11/1999 | Prudent et al. ............ | 435/6 |
| 5,994,069 A | 11/1999 | Hall et al. ............... | 435/6 |
| 6,001,567 A | 12/1999 | Brow et al. ............... | 435/6 |
| 6,060,288 A * | 5/2000 | Adams et al. ............. | 435/91.2 |
| 6,090,543 A | 7/2000 | Prudent et al. ............ | 435/6 |
| 6,194,149 B1 | 2/2001 | Neri et al. ............... | 436/6 |
| 6,348,314 B1 | 2/2002 | Prudent et al. ............ | 435/6 |
| 6,372,424 B1 | 4/2002 | Brow et al. ............... | 436/5 |
| 6,458,535 B1 | 10/2002 | Hall et al. ............... | 435/6 |
| 6,500,622 B2 * | 12/2002 | Bruchez et al. ............ | 435/6 |
| 6,548,021 B1 * | 4/2003 | Church et al. ............. | 422/68.1 |
| 6,692,917 B2 | 2/2004 | Neri et al. ............... | 435/6 |
| 2003/0104470 A1 | 6/2003 | Fors et al. | |
| 2004/0018491 A1* | 1/2004 | Gunderson et al. .......... | 435/6 |

FOREIGN PATENT DOCUMENTS

| WO | WO 97/27214 | 7/1997 |
|---|---|---|
| WO | WO 98/15267 | 4/1998 |
| WO | WO 98/42873 | 10/1998 |
| WO | WO 98/50403 | 11/1998 |

OTHER PUBLICATIONS

Maskos et al. oligonucleotide hybridization on glass supports: a novel linker for oligonucleotide synthesis and hybridization properties of oligonucleotides synthesized in situ. Nucleic acid Research, vol. 20, No. 7, pp. 1679-1684, Apr. 1992.*
Fors et al. large-scale SNP scoring from unamplified genomic DNA. Pharmacogenomics. vol. 1, No. 2, pp. 219-229, May 2000.*
Sojka et al. Evaluating the quality of oligonucleotides that are immobilized on glass supports for biosensor development. Analytica Chimica Acta. vol. 395, pp. 273-284, 1999.*
Griffin et al. Direct genetic analysis by matrix-assisted laser desorption/ionization mass spectrometery. Proc, Natl. Acad. sci. USA, vol. 96, pp. 6301-6306, May 1999.*
Griffin et al. PNAS, vol. 96, pp. 6301-6306, May 1999.*
Fors et al. Pharmacogenomics, vol. 1, No. 2, pp. 219-229, May 2000.*
Maskos et al. Nucleic acids Research, vol. 20, No. 7, pp. 1679-1684, 1992.*
Sojka et al. Analytica Chimica Acta, vol. 395, pp. 273-284, 1999.*
Kremsky, J.N. et al., "Immobilization of DNA via oligonucleotides containing an aldehyde or carboxylic acid group at the 5' terminus", Nucl. Acids Res., vol. 15, pp. 2891-2909 (1987).*
Brookes, A. J., "The essence of SNPs", Gene, vol. 234, pp. 177-186 (1999).*
Nolan, J.P. et al., "The emergence of flow cytometry for sensitive, real-time measurements of molecular interactions", Nature Biotechnol., vol. 16, pp. 633-638 (1998).*
U.S. Appl. No. 09/723,622, filed Dec. 8, 2000, Neri et al.
Lyamichev et al., Nat. Biotech., 17:292 (1999).
Hall et al., PNAS, USA, 97:8272 (2000).
Agarwal et al., Diagn. Mol. Pathol. 9:158 [2000].
Cooksey et al., Antimicrob. Agents Chemother. 44:1296 [2000].
Griffin and Smith, Trends Biotechnol., 18:77 [2000].
Griffin and Smith, Analytical Chemistry 72:3298 [2000].
Hessner et al., Clin. Chem. 46:1051 [2000].
Ledford et al., J. Molec. Diagnostics 2,:97 [2000].
Lyamichev et al., Biochemistry 39:9523 [2000].
Mein et al., Genome Res., 10:330 [2000].
Neri et al., Advances in Nucleic Acid and Protein Analysis 3826:117 [2000].
Fors et al., Pharmacogenomics 1:219 [2000].
Griffin et al., Proc. Natl. Acad. Sci. USA 96:6301 [1999].
Kwiatkowski et al., Mol. Diagn. 4:353 [1999].
Ryan et al., Mol. Diagn. 4:135 [1999].
Ma et al., J. Biol. Chem., 275:24693 [2000].
Reynaldo et al., J. Mol. Biol., 297:511 [2000].
Kaiser et al., J. Biol. Chem., 274:21387 [1999].

* cited by examiner

*Primary Examiner*—Teresa E. Strzelecka
(74) *Attorney, Agent, or Firm*—Medlen & Carroll, LLP

(57) ABSTRACT

The present invention relates to systems, compositions, and methods for the detection and characterization of nucleic acid sequences and variations in nucleic acid sequences. The present invention relates to methods for attaching nucleic acids to solid supports and modifying nucleic acids. For example, in some embodiments, the 5' nuclease activity of a cleavage agent is used to cleave a cleavage structure formed on the solid support, the occurrence of the cleavage event indicating the presence of specific nucleic acid sequences.

9 Claims, 18 Drawing Sheets

SEQUENCE LISTING

<160> NUMBER OF SEQ ID NOS: 19

<210> SEQ ID NO 1
<211> LENGTH: 30
<212> TYPE: DNA
<213> ORGANISM: Artificial Sequence
<220> FEATURE:
<223> OTHER INFORMATION: Synthetic

<400> SEQUENCE: 1
atagagccat aaactcaaag tggtaataat                                          30

<210> SEQ ID NO 2
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: The residue at this position is linked to a
      spacer bearing a Cy3 dye.
<220> FEATURE:
<221> NAME/KEY: misc_feature
<222> LOCATION: (12)..(12)
<223> OTHER INFORMATION: The residue at this position is attached to a
      Biotin.

<400> SEQUENCE: 2
gagtcctgtg atc                                                            13

<210> SEQ ID NO 3
<211> LENGTH: 49
<212> TYPE: DNA
<213> ORGANISM: Artificial Sequence
<220> FEATURE:
<223> OTHER INFORMATION: Synthetic

<400> SEQUENCE: 3
tgacaaaatc acaggtactc ttattaccac tttgagttta tggctctat                     49

<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
ccccggcctg gtacactgcc aggct                                               25

<210> SEQ ID NO 5
<211> LENGTH: 25
<212> TYPE: DNA
<213> ORGANISM: Artificial Sequence
<220> FEATURE:
<223> OTHER INFORMATION: Synthetic

<400> SEQUENCE: 5
ccccggcctg gtacactgcc aggct                                               25

<210> SEQ ID NO 6
<211> LENGTH: 18
<212> TYPE: DNA
<213> ORGANISM: Artificial Sequence

```
<220> FEATURE:
<223> OTHER INFORMATION: Synthetic
<220> FEATURE:
<221> NAME/KEY: modified_base
<222> LOCATION: (5)..(5)
<223> OTHER INFORMATION: The residue at this position is a fluorescein
      deoxythymidylic acid.

<400> SEQUENCE: 6
acttttgcag gtcatcgg                                                      18

<210> SEQ ID NO 7
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (5)..(5)
<223> OTHER INFORMATION: The residue at this position is a fluorescein
      deoxythymidylic acid.

<400> SEQUENCE: 7
acttttgcag gtcatcgg                                                      18

<210> SEQ ID NO 8
<211> LENGTH: 56
<212> TYPE: DNA
<213> ORGANISM: Artificial Sequence
<220> FEATURE:
<223> OTHER INFORMATION: Synthetic

<400> SEQUENCE: 8
cgcgatgccg atgacctgca gaagtgcctg gcagtgtacc aggccggggc ccgcga          56

<210> SEQ ID NO 9
<211> LENGTH: 56
<212> TYPE: DNA
<213> ORGANISM: Artificial Sequence
<220> FEATURE:
<223> OTHER INFORMATION: Synthetic

<400> SEQUENCE: 9
cgcgatgccg atgacctgca gaagcgcctg gcagtgtacc aggccggggc ccgcga          56

<210> SEQ ID NO 10
<211> LENGTH: 28
<212> TYPE: DNA
<213> ORGANISM: Artificial Sequence
<220> FEATURE:
<223> OTHER INFORMATION: Synthetic

<400> SEQUENCE: 10
cgcgccgagg gcttctgcag gtcatcgg                                           28

<210> SEQ ID NO 11
<211> LENGTH: 28
<212> TYPE: DNA
<213> ORGANISM: Artificial Sequence
<220> FEATURE:
<223> OTHER INFORMATION: Synthetic

<400> SEQUENCE: 11
cgcgccgagg gcttctgcag gtcatcgg                                           28

<210> SEQ ID NO 12
```

```
<211> LENGTH: 28
<212> TYPE: DNA
<213> ORGANISM: Artificial Sequence
<220> FEATURE:
<223> OTHER INFORMATION: Synthetic

<400> SEQUENCE: 12
cgcgccgagg gcttctgcag gtcatcgg                                              28

<210> SEQ ID NO 13
<211> LENGTH: 28
<212> TYPE: DNA
<213> ORGANISM: Artificial Sequence
<220> FEATURE:
<223> OTHER INFORMATION: Synthetic

<400> SEQUENCE: 13
cgcgccgagg gcttctgcag gtcatcgg                                              28

<210> SEQ ID NO 14
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: The residue at this position is attached to a
      quencher dye.

<400> SEQUENCE: 14
cgcgccgagg gcttctgcag gtcatcgg                                              28

<210> SEQ ID NO 15
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: The residue at this position is attached to a
      quencher dye.

<400> SEQUENCE: 15
cgcgccgagg gcttctgcag gtcatcgg                                              28

<210> SEQ ID NO 16
<211> LENGTH: 25
<212> TYPE: DNA
<213> ORGANISM: Artificial Sequence
<220> FEATURE:
<223> OTHER INFORMATION: Synthetic

<400> SEQUENCE: 16
ccccggcctg gtacactgcc aggct                                                 25

<210> SEQ ID NO 17
<211> LENGTH: 16
<212> TYPE: DNA
<213> ORGANISM: Artificial Sequence
<220> FEATURE:
<223> OTHER INFORMATION: Synthetic

<400> SEQUENCE: 17
ggtacactgc caggct                                                           16
```

```
<210> SEQ ID NO 18
<211> LENGTH: 15
<212> TYPE: DNA
<213> ORGANISM: Artificial Sequence
<220> FEATURE:
<223> OTHER INFORMATION: Synthetic

<400> SEQUENCE: 18
gtacactgcc aggct                                                15

<210> SEQ ID NO 19
<211> LENGTH: 12
<212> TYPE: DNA
<213> ORGANISM: Artificial Sequence
<220> FEATURE:
<223> OTHER INFORMATION: Synthetic

<400> SEQUENCE: 19
cactgccagg ct                                                   12
```

SOLID-PHASE REACTIONS

The present application claims priority to U.S. Provisional Application Ser. No. 60/328,947, filed Oct. 12, 2001, and U.S. patent application Ser. No. 10/197,189, filed Jul. 17, 2002, which claims priority to U.S. Provisional Application Ser. No. 60/306,010, filed Jul. 17, 2001, each of which is herein incorporated by reference.

FIELD OF THE INVENTION

The present invention relates to systems, compositions, and methods for the detection and characterization of nucleic acid sequences and variations in nucleic acid sequences. The present invention relates to methods for attaching nucleic acids to solid supports and modifying nucleic acids. For example, in some embodiments, the 5' nuclease activity of a cleavage agent is used to cleave a cleavage structure formed on the solid support, the occurrence of the cleavage event indicating the presence of specific nucleic acid sequences.

BACKGROUND OF THE INVENTION

Methods for the detection and characterization of specific nucleic acid sequences and sequence variations have been used to detect the presence of viral or bacterial nucleic acid sequences indicative of an infection and to detect the presence of variants or alleles of genes associated with diseases, conditions, and cancers. These methods also find application in the identification of sources of nucleic acids such as in forensic analysis or for paternity determinations.

Various methods are known in the art that may be used to detect and characterize specific nucleic acid sequences and sequence variants. Nonetheless, with the completion of the nucleic acid sequencing of the human genome, as well as the genomes of numerous pathogenic organisms, the demand for fast, reliable, cost-effective and user-friendly tests for the detection of specific nucleic acid sequences continues to grow. Importantly, these tests must be able to create a detectable signal from samples that contain very few copies of the sequence of interest.

Currently available technologies include signal amplification technologies including, the polymerase chain reaction (PCR) (as described in U.S. Pat. Nos. 4,683,195, 4,683,202, and 4,965,188, the disclosures of which are hereby incorporated by reference), the ligase chain reaction (LCR) (sometimes referred to as "Ligase Amplification Reaction" [LAR] described by Barany, Proc. Natl. Acad. Sci., 88:189 [1991]; Barany, PCR Methods and Applic., 1:5 [1991]; and Wu and Wallace, Genomics 4:560 [1989]), and the self-sustained sequence replication reaction (3SR) (See e.g., Guatelli et al., Proc. Natl. Acad. Sci., 87:1874-1878 [1990], with an erratum at Proc. Natl. Acad. Sci., 87:7797 [1990]; Kwok et al., Proc. Natl. Acad. Sci., 86:1173-1177 [1989]; and Fahy et al., PCR Meth. Appl., 1:25-33 [1991]). Other available technologies include direct detection technologies for quantitative detection of sequences, including the cycling probe reaction (CPR) (Duck et al., BioTech., 9:142 [1990]) and the use of branched DNA (bDNA), described by Urdea et al., Gene 61:253-264 (1987). While these techniques have been useful in certain contexts, improved systems and methods are needed to allow fast, reliable, cost-effective detection of nucleic acids without requiring inordinate amounts of sample.

SUMMARY OF THE INVENTION

The present invention relates to systems, compositions, and methods for the detection and characterization of nucleic acid sequences and variations in nucleic acid sequences. The present invention relates to methods for attaching nucleic acids to solid supports and modifying nucleic acids. For example, in some embodiments, the 5' nuclease activity of a cleavage agent is used to cleave a cleavage structure formed on the solid support, the occurrence of the cleavage event indicating the presence of specific nucleic acid sequences.

The present invention provides fast, reliable, cost-effective systems and methods for the detection of nucleic acids, including detection systems and methods that find use with trace amounts of target nucleic acid in a sample. While the present invention may be utilized with any number of detection technologies, alone, or in combination, the description provided herein focuses on the application to the INVADER assay (See e.g., Patents to Third Wave Technologies including U.S. Pat. Nos. 5,846,717; 6,090,543; 6,001,567; 5,985,557; 5,994,069, 6,214,545, 6,210,880, and 6,194,880; Lyamichev et al., Nat. Biotech., 17:292 (1999), Hall et al., PNAS, USA, 97:8272 (2000), Agarwal et al., Diagn. Mol. Pathol. 9:158 [2000], Cooksey et al., Antimicrob. Agents Chemother. 44:1296 [2000], Griffin and Smith, Trends Biotechnol., 18:77 [2000], Griffin and Smith, Analytical Chemistry 72:3298 [2000], Hessner et al., Clin. Chem. 46:1051 [2000], Ledford et al., J. Molec. Diagnostics 2,:97 [2000], Lyamichev et al., Biochemistry 39:9523 [2000], Mein et al., Genome Res., 10:330 [2000], Neri et al., Advances in Nucleic Acid and Protein Analysis 3826:117 [2000], Fors et al., Pharmacogenomics 1:219 [2000], Griffin et al., Proc. Natl. Acad. Sci. USA 96:6301 [1999], Kwiatkowski et al., Mol. Diagn. 4:353 [1999], and Ryan et al., Mol. Diagn. 4:135 [1999], Ma et al., J. Biol. Chem., 275: 24693 [2000], Reynaldo et al., J. Mol. Biol., 297:511 [2000], and Kaiser et al., J. Biol. Chem., 274:21387 [1999]; and PCT publications WO97/27214, WO98/42873, and WO98/50403, each of which is herein incorporated by reference in their entirety for all purposes) to illustrate preferred features of the present invention.

Currently there is a great deal of interest in solid-phase assays for nucleic acids analysis. DNA chips (Giles et al., Nature Biotechnol., 17:365 [1999]), microarrays (Southern et al., Nature Genetics Suppl., 21:5 [1999]), fiber-optic arrays (Steemers et al., Nature Biotechnol., 18:91 [2000]), and particle-based assays (Brenner et al., Nature Biotechnol., 18:630 [2000]) are all gaining prominence for nucleic acid applications. They offer the multiplexing capabilities required for high throughput analysis since a large number of different assays can be conducted simultaneously on a single sample. Many solid-phase techniques are based solely on hybridization, although single base differences are often difficult to uncover with hybridization-only approaches (Guo et al., Nucleic Acids Res., 22:5456 [1994], Guo et al., Nature Biotechnol., 15:331 [1997], and Howell et al., Nature Biotechnol., 17:87 [1999]). Other techniques, such as the oligonucleotide ligation assay, for example, incorporate the specificity of an enzyme to enhance discrimination of sequences that differ at only a single position (Landegren et al., Science 241:1077 [1988] and Gerry et al., J. Mol. Biol., 292:251 [1999]). In some embodiments, the present invention provides alternative enzymatic approaches on solid-phase platforms.

For example, the INVADER assay (Third Wave Technologies, Madison, Wis.) is a probe-cycling, signal-amplification reaction used for detection of single nucleotide polymorphisms (SNPs) and quantitative determination of gene expression and viral load. Typically, an invasive signal amplification reaction generates 30-50 cleaved probes per target per minute resulting in $10^3$- to $10^4$-fold signal amplification in a 1-3 h reaction (Lyamichev et al., Biochemistry 39:9523 [2000]). By combining two invasive cleavage reactions into a serial assay, the signal amplification can be increased to $10^7$-fold, which is sufficient to detect 600 copies of unique sequences in samples of human genomic DNA in 2-4 hours using a standard fluorescence plate reader (Hall et al., Proc. Natl. Acad. Sci. USA 97:8272 [2000]).

The number of different formats that can be applied for signal detection emphasizes the versatility of the invasive cleavage assay. These include electrophoresis (O'Connell et al., Electrophoresis 20:1211 [1999], Sander et al., Electophoresis 20:1131 [1999], and Oldenburg and Siebert, Bio-Techniques 28:351 [2000]), microplate enzyme-linked immunosorbent assay (ELISA) (Lyamichev et al., Nature Biotechnol., 17:292 [1999]), and matrix-assisted laser desorption/ionization time-of-flight (MADLI-TOF) mass spectrometry methods (Griffin et al., Proc. Natl. Acad. Sci. USA 96:6301 [1999]). More recently, a fluorescence resonance energy transfer (FRET) methodology enabled homogenous detection of SNPs by the invasive cleavage reaction using zeptomole ($10^{-21}$ mol) amounts of target DNA (Hall et al., Proc. Natl. Acad. Sci. USA 97:8272 [2000]).

The application of the invasive cleavage assay to a solid-phase format by the present invention provides the ability to analyze multiple SNPs in parallel. Publications report that SNP detection using the invasive cleavage reaction is performed in 96-well microplates with nanogram amounts of human genomic DNA per SNP (Hall et al., Proc. Natl. Acad. Sci. USA 97:8272 [2000]). Assuming that the total number of SNPs in the human genome is $3 \times 10^6$ (Brookes, Gene 234:177 [1999]), a complete genotype analysis of a single individual would require $3 \times 10^4$ plates and tens of milligrams of the DNA. The solid-phase formats of the present invention reduce the analysis to, for example, a single SNP chip that interrogates a small-volume sample of human DNA. Results of experiments conducted during the development of the present invention demonstrate that the multi-component substrate for the INVADER assay reaction can be properly assembled, accurately recognized by structure-specific nucleases, and efficiently cleaved on a solid surface. As in solution-phase assays, a single target molecule associates sequentially with multiple probe molecules and facilitates cleavage of these probes, thus yielding linear amplification of the signal. All solid-phase assay formats tested resulted in target-specific detection, regardless of which oligonucleotide(s) were attached to the surface or how labels were oriented on the cycling probe. Thus, in all formats and orientations tested, the properly assembled three-component substrate (target hybridized to upstream oligonucleotide and probe) was specifically recognized and cleaved by the enzyme.

Thus, in some embodiments of the present invention that are directed to invasive cleavage assays, the present invention provides a method for detecting a target sequence (e.g., a mutation, polymorphism, etc) comprising, providing a sample suspected of containing the target sequence; oligonucleotides capable of forming an invasive cleavage structure in the presence of the target sequence; and an agent for detecting the presence of an invasive cleavage structure, wherein one or more of the oligonucleotides or the agent is attached to a solid support; and exposing the sample to the oligonucleotides and the agent. In some embodiments, the method further comprises the step of detecting a complex comprising the agent and the invasive cleavage structure (directly or indirectly).

In some embodiments, the agent comprises a cleavage agent. In some preferred embodiments, the exposing of the sample to the oligonucleotides and the agent comprises exposing the sample to the oligonucleotides and the agent under conditions wherein an invasive cleavage structure is formed between the target sequence and the oligonucleotides if the target sequence is present in the sample, wherein the invasive cleavage structure is cleaved by the cleavage agent to form a cleavage product. In some embodiments, the method further comprises the step of detecting the cleavage product. In some embodiments, the target sequence comprises a first region and a second region, the second region downstream of and contiguous to the first region, wherein the oligonucleotides comprise first and second oligonucleotides, wherein at least a portion of the first oligonucleotide is completely complementary to the first portion of the target sequence and wherein the second oligonucleotide comprises a 3' portion and a 5' portion, wherein the 5' portion is completely complementary to the second portion of said target nucleic acid.

The present invention also provides a kit for detecting such target sequences, said kit comprising oligonucleotides capable of forming an invasive cleavage structure in the presence of the target sequence. In some embodiments, the kit further comprises an agent for detecting the presence of an invasive cleavage structure (e.g., a cleavage agent). In some embodiments, the oligonucleotides comprise first and second oligonucleotides, said first oligonucleotide comprising a 5' portion complementary to a first region of the target nucleic acid and said second oligonucleotide comprising a 3' portion and a 5' portion, said 5' portion complementary to a second region of the target nucleic acid downstream of and contiguous to the first portion.

The present invention also provides methods for detecting the presence of a target nucleic acid molecule by detecting non-target cleavage products comprising, providing: a cleavage agent; a source of target nucleic acid, the target nucleic acid comprising a first region and a second region, the second region downstream of and contiguous to the first region; a first oligonucleotide, wherein at least a portion of the first oligonucleotide is completely complementary to the first portion of the target nucleic acid; and a second oligonucleotide comprising a 3' portion and a 5' portion, wherein the 5' portion is completely complementary to the second portion of the target nucleic acid, wherein the cleavage agent, the target nucleic acid, the first oligonucleotide, and/or the second oligonucleotide is attached to a solid support; mixing the cleavage agent, the target nucleic acid, the first oligonucleotide and the second oligonucleotide to create a reaction mixture under reaction conditions such that at least the portion of the first oligonucleotide is annealed to the first region of said target nucleic acid and wherein at least the 5' portion of the second oligonucleotide is annealed to the second region of the target nucleic acid so as to create a cleavage structure, and wherein cleavage of the cleavage structure occurs to generate non-target cleavage product; and detecting the cleavage of the cleavage structure.

The detection of the cleavage of the cleavage structure can be carried out in any manner. In some embodiments, the detection of the cleavage of the cleavage structure comprises detecting the non-target cleavage product. In yet other embodiments, the detection of the cleavage of the cleavage structure comprises detection of fluorescence, mass, or fluorescence energy transfer. Other detection methods include, but are not limited to detection of radioactivity, luminescence, phosphorescence, fluorescence polarization, and charge.

The present invention is not limited by the nature of the 3' portion of the second oligonucleotide. In some preferred embodiments, the 3' portion of the second oligonucleotide comprises a 3' terminal nucleotide not complementary to the target nucleic acid. In some embodiments, the 3' portion of the second oligonucleotide consists of a single nucleotide not complementary to the target nucleic acid. In other embodiments, the 3' portion has a sequence identical to a sequence of the first oligonucleotide, such that the first and second oligonucleotides each share a sequence complementary to the same portion of the target nucleic acid.

Any of the components of the method may be attached to a solid support. For example, in some embodiments, the first oligonucleotide is attached to a solid support. In other embodiments, the second oligonucleotide is attached to a solid support. In yet other embodiments, the first and second oligonucleotides are attached to a solid support.

The cleavage agent can be any agent that is capable of cleaving invasive cleavage structures. In some preferred embodiments, the cleavage agent comprises a structure-specific nuclease. In particularly preferred embodiments, the structure-specific nuclease comprises a thermostable structure-specific nuclease (e.g., a thermostable 5' nuclease). Thermostable structure-specific nucleases include, but are not limited to, those having an amino acid sequence homologous to a portion of the amino acid sequence of a thermostable DNA polymerase derived from a thermophilic organism (e.g., *Thermus aquaticus, Thermus flavus*, and *Thermus thermophilus*). In other embodiments, the thermostable structure-specific nuclease is from the FEN-1, RAD2 or XPG class of nucleases, or a chimerical structure containing one or more portions of any of the above cleavage agents.

The method is not limited by the nature of the target nucleic acid. In some embodiments, the target nucleic acid is single stranded or double stranded DNA or RNA (e.g., genomic DNA, expressed RNA, pooled DNA or RNA, synthetic DNA or RNA, protein nucleic acid (PNA), etc.). In certain embodiments, the target nucleic acid is amplified (e.g. by PCR). In some embodiments, double stranded nucleic acid is rendered single stranded (e.g., by heat) prior to formation of the cleavage structure. In some embodiment, the source of target nucleic acid comprises a sample containing genomic DNA. Samples include, but are not limited to, blood, saliva, cerebral spinal fluid, pleural fluid, milk, lymph, sputum, semen, and plants.

In some embodiments, the reaction conditions for the method comprise providing a source of divalent cations. In some preferred embodiments, the divalent cation is selected from the group comprising $Mn^{2+}$ and $Mg^{2+}$ ions. In some embodiments, the reaction conditions for the method comprise providing the first and the second oligonucleotides in concentration excess compared to the target nucleic acid.

In some embodiments, the method further comprises providing a third oligonucleotide complementary to a third portion of said target nucleic acid upstream of the first portion of the target nucleic acid, wherein the third oligonucleotide is mixed with the reaction mixture.

In some embodiments, the reaction is run under conditions that allow the formation of multiple cleavage structures on a single target nucleic acid. For example, in some embodiments, the conditions comprise isothermal conditions that permit a plurality of first oligonucleotides to disassociate from the target nucleic acid. While the present invention is not limited by the number of cleavage structures formed on a particular target nucleic acid, in some preferred embodiments, two or more (3, 4, 5, . . . , 10, . . . , 10000, . . . ) of the plurality of first oligonucleotides form cleavage structures with a particular target nucleic acid, wherein the cleavage structures are cleaved to produce the non-target cleavage products.

The present invention also provides methods where a cleavage product from the above methods is used in a further invasive cleavage reaction or in another detection reaction.

The invention is not limited by the nature or composition of the oligonucleotides. These oligonucleotides may comprise DNA, RNA, protein nucleic acid (PNA) and combinations thereof as well as comprise modified nucleotides, universal bases, adducts, etc. Further, one or more of the oligonucleotides may contain a dideoxynucleotide at the 3' terminus.

In some preferred embodiments, the target nucleic acid is not completely complementary to one or more of the oligonucleotides. In a particularly preferred embodiment, the target nucleic acid is not completely complementary to the second oligonucleotide.

In some embodiments, oligonucleotides or other components are attached to solid supports through a spacer molecule. While the present invention is not limited by the nature of the spacer molecule, in some embodiments, spacer molecules include, but are not limited to, carbon chains, polynucleotides, biotin, and polyglycols.

The present invention is also not limited by the nature of the solid support. In some preferred embodiments, solid supports comprise glass, latex, or hydrogel solid supports. In other preferred embodiments, the solid supports comprise a bead, multi-well plate, column, or microarray. In still further preferred embodiments, the solid supports are coated with a material (e.g., gold, streptavidin, etc.).

In some embodiments, the present invention provides systems and methods for detection of polymorphisms directly from genomic DNA without amplification of the genomic DNA. For example, the present invention provides a method for detecting polymorphisms in unamplified genomic DNA, comprising, providing: a) unamplified genomic DNA and b) reagents for conducting an invasive cleavage reaction, wherein at least one of said reagents is attached to a solid surface; and treating the unamplified genomic DNA with the reagents under conditions such that the presence or absence of a polymorphism in the genomic DNA is identified. In some embodiments, the reagents are configured to detect a plurality of different polymorphisms in the genomic DNA (e.g., 100 or more, 1000 or more, 1,000,000 or more polymorphisms). In some preferred embodiments, the solid surface comprises a microsphere or a plurality of microspheres. Use of a plurality of microspheres allows large numbers of different invasive cleavage assays to be run in a small reaction volume (e.g., in a single reaction vessel) and allows small amounts of genomic DNA to be used (e.g., 50 micrograms or less of genomic DNA).

DEFINITIONS

To facilitate an understanding of the present invention, a number of terms and phrases are defined below:

As used herein, the terms "complementary" or "complementarity" are used in reference to polynucleotides (i.e., a sequence of nucleotides such as an oligonucleotide or a target nucleic acid) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The term "homology" and "homologous" refers to a degree of identity. There may be partial homology or complete homology. A partially homologous sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is influenced by such factors as the degree of complementarity between the nucleic acids, stringency of the conditions involved, and the $T_m$ of the formed hybrid. "Hybridization" methods involve the annealing of one nucleic acid to another complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

With regard to complementarity, it is important for some diagnostic applications to determine whether the hybridization represents complete or partial complementarity. For example, where it is desired to detect simply the presence or absence of pathogen DNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, may require that the hybridization method distinguish between partial and complete complementarity. It may be of interest to detect genetic polymorphisms. For example, human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia. It is well known that the genetic basis of the amino acid change involves a single base difference between the normal allele DNA sequence and the mutant allele DNA sequence.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "$T_m$" is used in reference to the "melting temperature." The melting temperature is the temperature at which a population of double-stranded nucleic acid molecules becomes half disassociated into single strands. Several equations for calculating the $T_m$ of nucleic acids are well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr. Thermodynamics and NMR of internal G.T mismatches in DNA. Biochemistry 36, 10581-94 (1997)) include more sophisticated computations which take structural and environmental, as well as sequence characteristics into account for the calculation of $T_m$.

As used herein the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids that are not completely complementary to one another be hybridized or annealed together.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 g/ml denatured salmon sperm DNA followed by washing in a solution comprising 5×SSPE, 0.1% SDS at 42° C. when a probe of about 500 nucleotides in length is employed.

The term "gene" refers to a DNA sequence that comprises control and coding sequences necessary for the production of an RNA having a non-coding function (e.g., a ribosomal or transfer RNA) or encoding a polypeptide or a precursor. The RNA or polypeptide can be encoded by a full-length coding sequence or by any portion of the coding sequence so long as the desired activity or function is retained.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified," "mutant," or "polymorphic" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprising two or more deoxyribonucleotides or ribonucleotides, preferably at least 5 nucleotides, more preferably at least about 10-15 nucleotides and more preferably at least about 15 to 30 or more nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "label" as used herein refers to any atom or molecule that can be used to provide a detectable (preferably quantifiable) effect, and that can be attached to a nucleic acid or protein. Labels include but are not limited to dyes; radiolabels such as $^{32}P$; binding moieties such as biotin; haptens such as digoxgenin; luminogenic, phosphorescent or fluorogenic moieties; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable.

The term "signal" as used herein refers to any detectable effect, such as would be caused or provided by a label or an assay reaction.

As used herein, the term "detector" refers to a system or component of a system, e.g., an instrument (e.g. a camera, fluorimeter, charge-coupled device, scintillation counter, etc.) or a reactive medium (X-ray or camera film, pH indicator, etc.), that can convey to a user or to another component of a system (e.g., a computer or controller) the presence of a signal or effect. A detector can be a photometric or spectrophotometric system, which can detect ultraviolet, visible or infrared light, including fluorescence or chemiluminescence; a radiation detection system; a spectroscopic system such as nuclear magnetic resonance spectroscopy, mass spectrometry or surface enhanced Raman spectrometry; a system such as gel or capillary electrophoresis or gel exclusion chromatography; or other detection systems known in the art, or combinations thereof.

The term "cleavage structure" as used herein, refers to a structure that is formed by the interaction of at least one probe oligonucleotide and a target nucleic acid, forming a structure comprising a duplex, the resulting structure being cleavable by a cleavage agent, including but not limited to an enzyme. The cleavage structure is a substrate for specific cleavage by the cleavage agent in contrast to a nucleic acid molecule that is a substrate for non-specific cleavage by agents such as phosphodiesterases that cleave nucleic acid molecules without regard to secondary structure (i.e., no formation of a duplexed structure is required).

The term "folded cleavage structure" as used herein, refers to a region of a single-stranded nucleic acid substrate containing secondary structure, the region being cleavable by an enzymatic cleavage agent. The cleavage structure is a substrate for specific cleavage by the cleavage agent in contrast to a nucleic acid molecule that is a substrate for non-specific cleavage by agents such as phosphodiesterases that cleave nucleic acid molecules without regard to secondary structure (i.e., no folding of the substrate is required).

As used herein, the term "folded target" refers to a nucleic acid strand that contains at least one region of secondary structure (i.e., at least one double stranded region and at least one single-stranded region within a single strand of the nucleic acid). A folded target may comprise regions of tertiary structure in addition to regions of secondary structure.

The term "cleavage means" or "cleavage agent" as used herein refers to any agent that is capable of cleaving a cleavage structure, including but not limited to enzymes. "Structure-specific nucleases" or "structure-specific enzymes" are enzymes that recognize specific secondary structures in a nucleic acid molecule and cleave these structures. The cleavage agents of the invention cleave a nucleic acid molecule in response to the formation of cleavage structures; it is not necessary that the cleavage agents cleave the cleavage structure at any particular location within the cleavage structure.

The term "thermostable" when used in reference to an enzyme, such as a 5' nuclease, indicates that the enzyme is functional or active (i.e., can perform catalysis) at an elevated temperature, i.e., at about 55° C. or higher.

The term "cleavage products" as used herein, refers to products generated by the reaction of a cleavage agent with a cleavage structure (i.e., the treatment of a cleavage structure with a cleavage agent).

The term "target nucleic acid" refers to a nucleic acid molecule to be detected. In some embodiments, target nucleic acids contain a sequence that has at least partial complementarity with at least a probe oligonucleotide and may also have at least partial complementarity with an INVADER oligonucleotide (described below). The target nucleic acid may comprise single- or double-stranded DNA or RNA.

The term "probe oligonucleotide" refers to an oligonucleotide that interacts with a target nucleic acid to form a detection complex or cleavage structure. When annealed to the target nucleic acid to form a cleavage structure, cleavage occurs within the probe oligonucleotide.

As used herein, the term "signal probe" refers to a probe oligonucleotide containing a detectable moiety. The present invention is not limited by the nature of the detectable moiety.

As used herein, the terms "quencher" and "quencher moiety" refer to a molecule or material that suppresses or diminishes the detectable signal from a detectable moiety when the quencher is in the physical vicinity of the detectable moiety. For example, in some embodiments, quenchers are molecules that suppress the amount of detectable fluorescent signal from an oligonucleotide containing a fluorescent label when the quencher is physically near the fluorescent label.

The term "non-target cleavage product" refers to a product of a cleavage reaction that is not derived from the target nucleic acid. As discussed above, in the methods of the present invention, cleavage of a cleavage structure generally occurs within the probe oligonucleotide. The fragments of the probe oligonucleotide generated by this target nucleic acid-dependent cleavage are "non-target cleavage products."

The term "INVADER oligonucleotide" refers to an oligonucleotide that hybridizes to a target nucleic acid at a location near the region of hybridization between a probe and the target nucleic acid, wherein the INVADER oligonucleotide comprises a portion (e.g., a chemical moiety, or nucleotide—whether complementary to that target or not) that overlaps with the region of hybridization between the probe and target. In some embodiments, the INVADER oligonucleotide contains sequences at its 3' end that are substantially the same as sequences located at the 5' end of a probe oligonucleotide.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "liberating" as used herein refers to the release of a nucleic acid fragment from a larger nucleic acid fragment, such as an oligonucleotide, by the action of, for example, a 5' nuclease such that the released fragment is no longer covalently attached to the remainder of the oligonucleotide.

The term "$K_m$" as used herein refers to the Michaelis-Menten constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides.

The term "polymorphic locus" is a locus present in a population that shows variation between members of the population (e.g., the most common allele has a frequency of less than 0.95). In contrast, a "monomorphic locus" is a genetic locus at which little or no variation is seen between members of the population (generally taken to be a locus at which the most common allele exceeds a frequency of 0.95 in the gene pool of the population).

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "source of target nucleic acid" refers to any sample that contains nucleic acids (RNA or DNA). Particularly preferred sources of target nucleic acids are biological samples including, but not limited to cell lysates, blood, saliva, cerebral spinal fluid, pleural fluid, milk, lymph, sputum and semen.

An oligonucleotide is said to be present in "excess" relative to another oligonucleotide (or target nucleic acid sequence) if that oligonucleotide is present at a higher molar concentration than the other oligonucleotide (or target nucleic acid sequence). When an oligonucleotide such as a probe oligonucleotide is present in a cleavage reaction in excess relative to the concentration of the complementary target nucleic acid sequence, the reaction may be used to indicate the amount of the target nucleic acid present. Typically, when present in excess, the probe oligonucleotide will be present in at least a 100-fold molar excess; typically at least 1 pmole of each probe oligonucleotide would be used when the target nucleic acid sequence was present at about 10 fmoles or less.

A sample "suspected of containing" a first and a second target nucleic acid may contain either, both or neither target nucleic acid molecule.

The term "charge-balanced" oligonucleotide refers to an oligonucleotide (the input oligonucleotide in a reaction) that has been modified such that the modified oligonucleotide bears a charge, such that when the modified oligonucleotide is either cleaved (i.e., shortened) or elongated, a resulting product bears a charge different from the input oligonucleotide (the "charge-unbalanced" oligonucleotide) thereby permitting separation of the input and reacted oligonucleotides on the basis of charge. The term "charge-balanced" does not imply that the modified or balanced oligonucleotide has a net neutral charge (although this can be the case). Charge-balancing refers to the design and modification of an oligonucleotide such that a specific reaction product generated from this input oligonucleotide can be separated on the basis of charge from the input oligonucleotide.

The term "net neutral charge" when used in reference to an oligonucleotide, including modified oligonucleotides, indicates that the sum of the charges present (i.e., $R-NH_3^+$ groups on thymidines, the N3 nitrogen of cytosine, presence or absence or phosphate groups, etc.) under the desired reaction or separation conditions is essentially zero. An oligonucleotide having a net neutral charge would not migrate in an electrical field.

The term "net positive charge" when used in reference to an oligonucleotide, including modified oligonucleotides, indicates that the sum of the charges present (i.e., $R-NH_3^+$ groups on thymidines, the N3 nitrogen of cytosine, presence or absence or phosphate groups, etc.) under the desired reaction conditions is +1 or greater. An oligonucleotide having a net positive charge would migrate toward the negative electrode in an electrical field.

The term "net negative charge" when used in reference to an oligonucleotide, including modified oligonucleotides, indicates that the sum of the charges present (i.e., $R-NH_3^+$ groups on thymidines, the N3 nitrogen of cytosine, presence or absence or phosphate groups, etc.) under the desired reaction conditions is −1 or lower. An oligonucleotide having a net negative charge would migrate toward the positive electrode in an electrical field.

The term "polymerization means" or "polymerization agent" refers to any agent capable of facilitating the addition of nucleoside triphosphates to an oligonucleotide. Preferred polymerization means comprise DNA and RNA polymerases.

The term "ligation means" or "ligation agent" refers to any agent capable of facilitating the ligation (i.e., the formation of a phosphodiester bond between a 3'-OH and a 5' P located at the termini of two strands of nucleic acid). Preferred ligation means comprise DNA ligases and RNA ligases.

The term "reactant" is used herein in its broadest sense. The reactant can comprise, for example, an enzymatic reactant, a chemical reactant or light (e.g., ultraviolet light, particularly short wavelength ultraviolet light is known to break oligonucleotide chains). Any agent capable of reacting with an oligonucleotide to either shorten (i.e., cleave) or elongate the oligonucleotide is encompassed within the term "reactant."

The term "adduct" is used herein in its broadest sense to indicate any compound or element that can be added to an oligonucleotide. An adduct may be charged (positively or negatively) or may be charge-neutral. An adduct may be added to the oligonucleotide via covalent or non-covalent linkages. Examples of adducts include, but are not limited to, indodicarbocyanine dye amidites, amino-substituted nucleotides, ethidium bromide, ethidium homodimer, (1,3-propanediamino)propidium, (diethylenetriamino)propidium, thiazole orange, (N-N'-tetramethyl-1,3-propanediamino)propyl thiazole orange, (N-N'-tetramethyl-1,2-ethanediamino)propyl thiazole orange, thiazole orange-thiazole orange homodimer (TOTO), thiazole orange-thiazole blue heterodimer (TOTAB), thiazole orange-ethidium heterodimer 1 (TOED1), thiazole orange-ethidium heterodimer 2 (TOED2) and fluorescein-ethidium heterodimer (FED), psoralens, biotin, streptavidin, avidin, dabcyl, fluorescein, etc.

As used herein, the terms "purified" or "substantially purified" refer to molecules, either nucleic acid or amino acid sequences, that are removed from their natural environment, isolated or separated, and are preferably at least 60% free, more preferably 75% free, and most preferably 90% free from other components with which they are naturally associated. A molecule (e.g., a nucleic acid molecule) that is increased in relative amount compared to other molecules (e.g., by amplification) may also be said to be purified. An "isolated polynucleotide" or "isolated oligonucleotide" is therefore a substantially purified polynucleotide.

The term "ARRESTOR molecule" refers to an agent added to or included in an invasive cleavage reaction in order to stop one or more reaction components from participating in a subsequent action or reaction. This may be done by sequestering or inactivating some reaction component (e.g., by binding or base-pairing a nucleic acid component, or by binding to a protein component). The term "ARRESTOR oligonucleotide" refers to an oligonucleotide included in an invasive cleavage reaction in order to stop or arrest one or more aspects of any reaction (e.g., the first reaction and/or any subsequent reactions or actions; it is not intended that the ARRESTOR oligonucleotide be limited to any particular reaction or reaction step). However, it is not intended that the term be so limited as to just situations in which a reaction component is sequestered.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As used herein, the terms "solid support" or "support" refer to any material that provides a solid or semi-solid structure with which another material can be attached. Such materials include smooth supports (e.g., metal, glass, plastic, silicon, and ceramic surfaces) as well as textured and porous materials. Such materials also include, but are not limited to, gels, rubbers, polymers, and other non-rigid materials. Solid supports need not be flat. Supports include any type of shape including spherical shapes (e.g., beads). Materials attached to solid support may be attached to any portion of the solid support (e.g., may be attached to an interior portion of a porous solid support material). Preferred embodiments of the present invention have biological molecules such as nucleic acid molecules and proteins attached to solid supports. A biological material is "attached" to a solid support when it is associated with the solid support through a non-random chemical or physical interaction. In some preferred embodiments, the attachment is through a covalent bond. However, attachments need not be covalent or permanent. In some embodiments, materials are attached to a solid support through a "spacer molecule" or "linker group." Such spacer molecules are molecules that have a first portion that attaches to the biological material and a second portion that attaches to the solid support. Thus, when attached to the solid support, the spacer molecule separates the solid support and the biological materials, but is attached to both.

As used herein, the terms "bead" and "particle" and "microsphere" refer to small solid supports that are capable of moving about in a solution (i.e., have dimensions smaller than those of the enclosure in which they reside). In some preferred embodiments, beads are completely or partially spherical or cylindrical. However, beads are not limited to any particular three-dimensional shape.

As used herein, the term "microarray" refers to a solid support with a plurality of molecules (e.g., nucleotides) bound to its surface. Microarrays, for example, are described generally in Schena, "Microarray Biochip Technology," Eaton Publishing, Natick, Mass., 2000. Additionally, the term "patterned microarrays" refers to microarray substrates with a plurality of molecules non-randomly bound to its surface.

DESCRIPTION OF THE INVENTION

Figure 1:
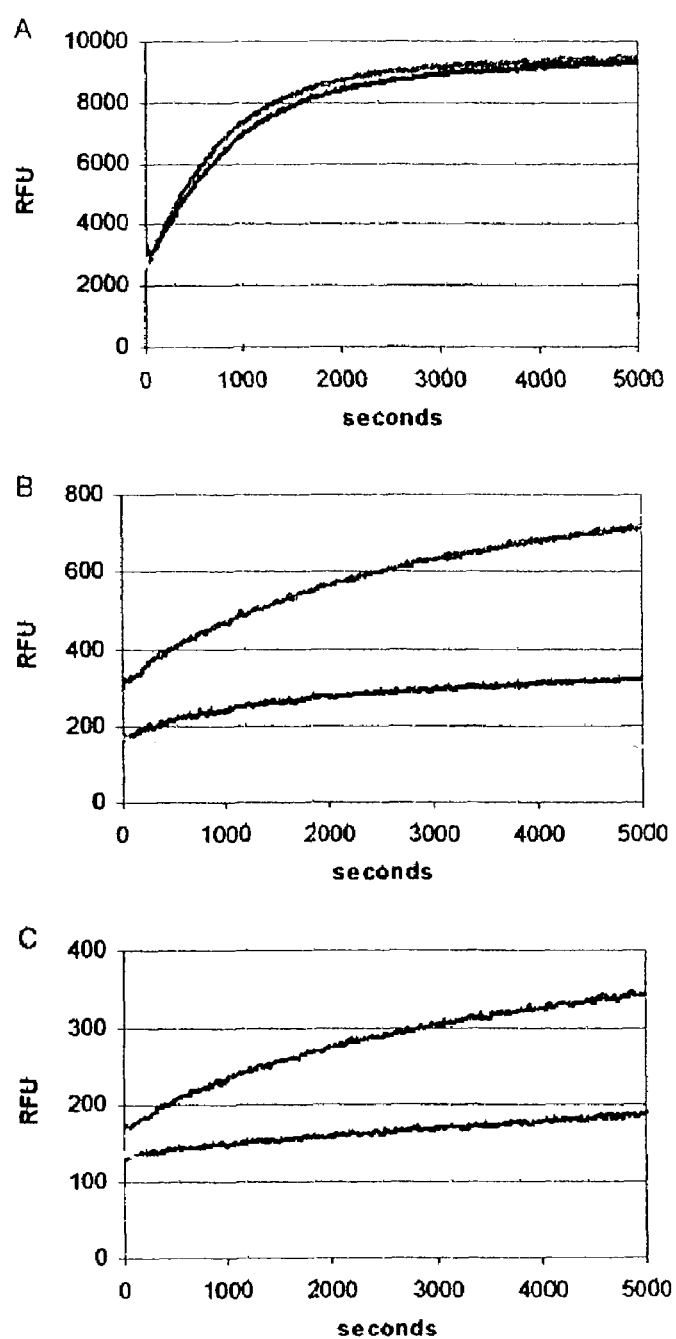
FIGS. 1A-C show graphs plotting signal generation versus time for model-system solid-phase and solution-phase invasive cleavage reactions.

The present invention relates to systems, methods and compositions for treating nucleic acids, and in particular, systems, methods and compositions for detection and characterization of nucleic acid sequences and sequence changes.

The detailed description of the invention is presented in the following sections: I) Solid Phase Invasive Cleavage Reactions; II) Other Solid Phase Reactions; and III) Kits.

I. Solid Phase Invasive Cleavage Reactions

A. Existing Technology

The majority of methods for scoring known SNPs/mutations fall into two broad categories: (1) hybridization methods, i.e. those that detect mutations based on the effects that a mismatch causes on the thermodynamics of oligonucleotide hybridization (i.e. melting temperature, or $T_m$); and (2) enzymatic methods that amplify, cleave, or extend nucleic acids based on either their sequence, their structure, or both.

1. Hybridization-Based Methods

One area of extremely active technology development is an array-based approach to DNA sequencing, or sequencing by hybridization (SBH). These methods employ a solid phase probing system (Smith et al., J. Comput. Biol., 5:255 [1998]). This allows for facilitated sample handling and oligonucleotide purification, decreased losses during sample handling, reduction of interference between oligonucleotides and, perhaps most importantly, unique identifying information through "addressing" of oligonucleotides. Second, the ability to attach thousands of oligonucleotides (or target molecules) gives these methods the potential to interrogate vast numbers of loci in parallel.

SBH is based on the well-established principle of allele-specific oligonucleotide hybridization (ASO). Instead of using chemistry to fractionate DNA based on its sequence, SBH relies on elucidating sequence by virtue of complementarity of a test sequence, i.e. a target molecule, to an array of oligonucleotides of known sequence. There are two principal formats being developed at present. In Format 1, the DNA target is affixed to a solid support in multiple, repeating arrays of microspots (~6 mm$^2$; Drmanac et al., Nature Biotechnology, 16:54 [1998]). These arrays are compartmentalized, either physically (e.g. with a metal grid) or chemically (e.g. with hydrophobic substances). Each compartment becomes a hybridization chamber to which distinct sets of oligonucleotides are added. This approach was pioneered by Hyseq (Sunnyvale, Calif.), which claims the ability to analyze multiple targets per array as a key advantage of this design.

Format 2 relies on an inverse approach. Multiple oligonucleotides are bound to the solid support—typically the oligonucleotides are synthesized directly on the surface by combinatorial masking—and the DNA target, which must be a small, amplified locus, is simultaneously interrogated by the entire array. Affymetrix (Santa Clara, Calif.) has led the field in developing high-resolution photolithographic processes for creating increasingly complex arrays. As many as 400,000 oligonucleotides have been synthesized on 1.6 cm$^2$ chip surfaces, though published studies have emphasized arrays comprising 96,000 (Hacia et al., Nature Genetics 14:441 [1996]) to 135,000 (Chee et al., Science, 274:610 [1996]) elements. The application of electric fields to each hybridization position is a variation of this approach, developed by Nanogen (San Diego, Calif.), that dramatically reduces the time required for hybridization from 1-2 hours to a matter of seconds (Sosonowski et al., PNAS, 94:1119 [1997]).

The use of such arrays for SNP discovery requires as many as 8-16 oligonucleotides per nucleotide interrogated, hence the complex arrays comprising hundreds of thousands of elements. However, their use for SNP scoring is potentially much less complicated. Two oligonucleotides, one in which the central position is designed to be complementary to the SNP, and another complementary to the wild type sequence, are sufficient to indicate the presence or absence of a given polymorphism. Nonetheless, SBH applications suffer from significant limitations that preclude their immediate adoption as a broad-based solution to SNP genotyping. Most notably, they are only appropriate for those applications in which fewer than 100 samples are processed per day in a given laboratory. Furthermore, reliance on PCR (or other target amplification procedures) to generate ample copies of target molecules for analysis severely limits throughput and increases cost. SBH is also hampered by the very nature of allele specific hybridization. Namely, the efficiency of hybridization and the thermal stability of hybrids formed between the target and a short oligonucleotide depend strongly on the particular sequences involved. So too, the degree of destabilization of the target molecule mismatched with an oligonucleotide at a single position depends on the sequence of the bases flanking the mismatch. Thus, it is impossible to design a single set of hybridization conditions that would function optimally for a large number of oligonucleotide elements (Pastinen et al., Genome Research, 7:606 [1997]). There have been reports of the use of small molecule additives that may minimize sequence dependent hybridization differences; however, at present little information on these innovations is available.

2. Multiplexed Allele-Specific Diagnostic Assay (MASDA)

MASDA is a forward dot blot procedure in which hundreds of target samples are spotted onto a membrane and then hybridized with a multiplexed solution of pooled, labeled probes (Shuber et al., Human Molecular Genetics, 6:337 [1997]). The labeled probes are then eluted from the filter and identified by conventional sequencing or chemical cleavage methods. The chief advantage of this method is its suitability for analyzing large numbers of target sequences (>500) with large numbers of probes (>100) in a single hybridization assay, though each target-probe hybrid must be analyzed individually. MASDA is extremely cumbersome, not amenable to automation, and dependent on target amplification to obtain sufficient amounts of hybrid for analysis.

3. Enzymatic Approaches i. Minisequencing

One method designed to circumvent the inherent limitations of allele specific hybridization is minisequencing. This technique, designed to detect SNPs/point mutations, uses a DNA polymerase to extend an oligonucleotide primer immediately adjacent to the polymorphism on an amplified target molecule (Pastinen et al., Genome Research, 7: 606 [1997]). A single labeled nucleotide and the remaining three unlabeled dNTPs are then added. DNA polymerization is allowed to occur for only a few seconds, such that the primer is extended by only a small number of bases. When a test molecule is compared to a reference, all positions, except that of the SNP, are identical. By relying on enzymatic activity rather than on the thermodynamics of hybrid formation to detect point mutations, this assay is able to achieve at least an order of magnitude greater degree of discrimination between mutant and wild type samples. Pastinen et al. have recently demonstrated that this technique can be carried out in a chip format (Pastinen et al., Genome Research, 7: 606 [1997]). Despite the potential of this approach to overcome some of the shortcomings of ASO-based SNP scoring, minisequencing is limited to examination of amplified targets, limiting its potential throughput.

ii. Taq Man and Other PCR-based Assays

Methods that rely on enzymatic or chemical agents to detect the presence of a mismatch can be considered to be structure, rather than sequence, specific. These methods include Allele-specific PCR, PCR-Ligase Detection Reaction (PCR-LDR), PCR-TaqMan (PE Biosystems, Foster City, Calif.), and Bridge Amplification Technology (Mosaic Technologies, Boston, Mass.). Allele-specific PCR makes use of PCR primers designed to amplify one allele but not another. The most common approach is to position the polymorphic base at the 3' terminus of a primer (Kwok et al., Nuc. Acid. Res., 18:999 [1990]). Although such 3' terminal mismatches do not significantly destabilize the primer, they are less efficiently extended by DNA polymerases. This discrimination, however, is considered to be very "leaky", meaning that many such mismatches are extended to some degree. PCR-LDR is an elegant means of evaluating PCR products that has been successfully applied to detection of drug resistance mutations in HIV (Landegren et al., Science, 241:1077 [1988]). In this approach, the ability to discriminate single base changes relies on the requirements of DNA ligase for fully annealed 3' ends of the upstream fragments being ligated to downstream primers (Landegren et al., Science, 241:1077 [1988]). However, in a best case, this method achieves only about 10% discrimination of mutant from wild type virus when multiple variants are present in a single sample. TaqMan is based on exonucleolytic degradation of a labeled probe hybridized to a PCR product (Livak et al., PCR Methods and Applications, 4:357 [1995]). The presence of a mismatch impairs hybridization, resulting in a reduction of signal generated from the mismatched probe and making the technique of questionable value for mixed samples, particularly when one allele is present as a small fraction of the total population. Because it is dependent on target amplification, the TaqMan procedure is typically carried out in sealed chambers in a dedicated, semi-automated fluorescence detection instrument.

Bridge Amplification Technology (Mosiac Technologies, Waltham, Mass.) is another method utilizing PCR for highly multiplexed detection. The basis of this approach is that the two PCR primers are affixed adjacent to one another on a solid surface. Double stranded target DNA is denatured and allowed to anneal to the primers. During the first annealing, each target strand hybridizes to a bound primer. During the extension, complementary strands are synthesized and are covalently attached to the surface via a primer. During the second annealing step, the 3' end of each newly synthesized single strand anneals with an adjacent primer, which is then extended to create a covalently attached, double-stranded product. By relying on primers bound to the surface, this technique avoids many of the shortcomings of PCR amplification that have precluded its widespread use for clinical applications. The most important of these is that this method does not promote carry-over contamination, which is the single greatest obstacle to the use of PCR in clinical settings. This method is suitable for high level multiplexing and parallel analysis of hundreds or thousands of loci from a single sample; however, it has yet to be applied to single base discrimination. Moreover, any SNP analysis based on this approach will by necessity rely on the allelic discrimination inherent in the PCR reaction. As described above, such methods are leaky and not likely to allow precise detection of a rare allele present as less than ~10% of a mixed population (Shafer et al., J. clinical Microbiology, 34:1849 [1996]).

B. Solid-Phase INVADER Assay-Based SNP Genotyping

The existing SNP genotyping technologies fall short in key areas. Notably, most existing methods rely on investigating small loci (usually no more than a few hundred base pairs) generated by target amplification procedures, usually PCR. Furthermore, target amplification methods are notoriously low throughput, costly, and cumbersome to execute.

An ideal method for SNP genotyping would be capable of massively parallel analysis of multiple sites (Wang et al., Science, 280:1077 [1998]), be suitable for the analysis of genomic DNA extracted from patient samples, i.e. without intervening target amplification steps (Pastinen et al., Genome Research, 7: 606 [1997]), be able to detect a rare allele in a mixed population of nucleic acid molecules, provide a high degree of discrimination between wild type and polymorphic sequences (Pastinen et al., Genome Research, 7: 606 [1997]), be readily adapted to include additional SNPs as they are discovered (Wang et al., Science, 280:1077 [1998]; Collins et al., Science, 278:1580 [1997]), be able to include an internal control or reference sample (Wang et al., Science, 280:1077 [1998]), and be inexpensive, simple to execute and automatable.

As the discovery of SNPs accelerates due to the rapid progress of the Human Genome Project, it is clear that there will be an acute need for high throughput methods that meet all of these criteria.

Accordingly, in some embodiments, the present invention provides a solid phase INVADER assay system suitable for the analysis of multiple polymorphisms from a single genomic sample. In some embodiments, the target molecule is provided in solution and one or more of the oligonucleotides used in the INVADER assay reaction are immobilized. However, in other embodiments, any or all of the nucleic acids, including the target, is immobilized. Additionally, in yet other embodiments, the cleavage agent (e.g., enzyme) and one or more of the nucleic acids are immobilized.

The INVADER assay (Third Wave Technologies, Madison, Wis.) is described in a number of patents and publications (See e.g., U.S. Pat. Nos. 5,846,717, 6,090,543, 6,001,567, 5,985,557, and 5,994,069; Lyamichev et al., Nat. Biotech., 17:292 (1999), Hall et al., PNAS, USA, 97:8272 (2000), Agarwal et al., Diagn. Mol. Pathol. 9:158 [2000], Cooksey et al., Antimicrob. Agents Chemother. 44:1296 [2000], Griffin and Smith, Trends Biotechnol., 18:77 [2000], Griffin and Smith, Analytical Chemistry 72:3298 [2000], Hessner et al., Clin. Chem. 46:1051 [2000], Ledford et al., J. Molec. Diagnostics 2,:97 [2000], Lyamichev et al., Biochemistry 39:9523 [2000], Mein et al., Genome Res., 10:330 [2000], Neri et al., Advances in Nucleic Acid and Protein Analysis 3826:117 [2000], Fors et al., Pharmacogenomics 1:219 [2000], Griffin et al., Proc. Natl. Acad. Sci. USA 96:6301 [1999], Kwiatkowski et al., Mol. Diagn. 4:353 [1999], and Ryan et al., Mol. Diagn. 4:135 [1999], Ma et al., J. Biol. Chem., 275:24693 [2000], Reynaldo et al., J. Mol. Biol., 297:511 [2000], and Kaiser et al., J. Biol. Chem., 274:21387 [1999]; and PCT publications WO97/27214 and WO9842873, each of which is herein incorporated by reference in their entireties).

The present invention provides means for forming a nucleic acid cleavage structure that is dependent upon the presence of a target nucleic acid and cleaving the nucleic acid cleavage structure so as to release distinctive cleavage products. 5' nuclease activity, for example, is used to cleave the target-dependent cleavage structure and the resulting cleavage products are indicative of the presence of specific target nucleic acid sequences in the sample. When two strands of nucleic acid, or oligonucleotides, both hybridize to a target nucleic acid strand such that they form an overlapping invasive cleavage structure, as described below, invasive cleavage can occur. Through the interaction of a cleavage agent (e.g., a 5' nuclease) and the upstream oligonucleotide, the cleavage agent can be made to cleave the downstream oligonucleotide at an internal site in such a way that a distinctive fragment is produced. Such embodiments have been termed the INVADER assay.

The present invention further provides assays in which the target nucleic acid is reused or recycled during multiple rounds of hybridization with oligonucleotide probes and cleavage of the probes without the need to use temperature cycling (i.e., for periodic denaturation of target nucleic acid strands) or nucleic acid synthesis (i.e., for the polymerization-based displacement of target or probe nucleic acid strands). When a cleavage reaction is run under conditions in which the probes are continuously replaced on the target strand (e.g. through probe-probe displacement or through an equilibrium between probe/target association and disassociation, or through a combination comprising these mechanisms, [Reynaldo et al., J. Mol. Biol., 97:511 (2000)]) multiple probes can hybridize to the same target, allowing multiple cleavages, and the generation of multiple cleavage products.

By the extent of its complementarity to a target nucleic acid strand, an oligonucleotide may be said to define a specific region of said target. In an invasive cleavage structure, the two oligonucleotides define and hybridize to regions of the target that are adjacent to one another (i.e., regions without any additional region of the target between them). Either or both oligonucleotides may comprise additional portions that are not complementary to the target strand. In addition to hybridizing adjacently, in order to form an invasive cleavage structure, the 3' end of the upstream oligonucleotide comprises an additional moiety. When both oligonucleotides are hybridized to a target strand to form a structure and such a 3' moiety is present on the upstream oligonucleotide within the structure, the oligonucleotides may be said to overlap, and the structure may be described as an overlapping, or invasive cleavage structure.

In one embodiment, the 3' moiety of the invasive cleavage structure is a single nucleotide. In this embodiment the 3' moiety may be any nucleotide (i.e., it may be, but it need not be complementary to the target strand). In a preferred embodiment the 3' moiety is a single nucleotide that is not complementary to the target strand. In another embodiment, the 3' moiety is a nucleotide-like compound (i.e., a moiety having chemical features similar to a nucleotide, such as a nucleotide analog or an organic ring compound; See e.g., U.S. Pat. No. 5,985,557). In yet another embodiment the 3' moiety is one or more nucleotides that duplicate in sequence one or more nucleotides present at the 5' end of the hybridized region of the downstream oligonucleotide. In a further embodiment, the duplicated sequence of nucleotides of the 3' moiety is followed by a single nucleotide that is not further duplicative of the downstream oligonucleotide sequence, and that may be any other nucleotide. In yet another embodiment, the duplicated sequence of nucleotides of the 3' moiety is followed by a nucleotide-like compound, as described above.

The downstream oligonucleotide may have, but need not have, additional moieties attached to either end of the region that hybridizes to the target nucleic acid strand. In a preferred embodiment, the downstream oligonucleotide comprises a moiety at its 5' end (i.e., a 5' moiety). In a particularly preferred embodiment, said 5' moiety is a 5' flap or arm comprising a sequence of nucleotides that is not complementary to the target nucleic acid strand.

When an overlapping cleavage structure is formed, it can be recognized and cleaved by a nuclease that is specific for this structure (i.e., a nuclease that will cleave one or more of the nucleic acids in the overlapping structure based on recognition of this structure, rather than on recognition of a nucleotide sequence of any of the nucleic acids forming the structure). Such a nuclease may be termed a "structure-specific nuclease". In some embodiments, the structure-specific nuclease is a 5' nuclease. In a preferred embodiment, the structure-specific nuclease is the 5' nuclease of a DNA polymerase. In another preferred embodiment, the DNA polymerase having the 5' nuclease is synthesis-deficient. In another preferred embodiment, the 5' nuclease is a FEN-1 endonuclease. In a particularly preferred embodiment, the 5' nuclease is thermostable.

In some embodiments, said structure-specific nuclease preferentially cleaves the downstream oligonucleotide. In a preferred embodiment, the downstream oligonucleotide is cleaved one nucleotide into the 5' end of the region that is hybridized to the target within the overlapping structure. Cleavage of the overlapping structure at any location by a structure-specific nuclease produces one or more released portions or fragments of nucleic acid, termed "cleavage products."

In some embodiments, cleavage of an overlapping structure is performed under conditions wherein one or more of the nucleic acids in the structure can disassociate (i.e. un-hybridize, or melt) from the structure. In one embodiment, full or partial disassociation of a first cleavage structure allows the target nucleic acid to participate in the formation of one or more additional overlapping cleavage structures. In a preferred embodiment, the first cleavage structure is partially disassociated. In a particularly preferred embodiment only the oligonucleotide that is cleaved disassociates from the first cleavage structure, such that it may be replaced by another copy of the same oligonucleotide. In some embodiments, said disassociation is induced by an increase in temperature, such that one or more oligonucleotides can no longer hybridize to the target strand. In other embodiments, said disassociation occurs because cleavage of an oligonucleotide produces only cleavage products that cannot bind to the target strand under the conditions of the reaction. In a preferred embodiment, conditions are selected wherein an oligonucleotide may associate with (i.e., hybridize to) and disassociate from a target strand regardless of cleavage, and wherein the oligonucleotide may be cleaved when it is hybridized to the target as part of an overlapping cleavage structure. In a particularly preferred embodiment, conditions are selected such that the number of copies of the oligonucleotide that can be cleaved when part of an overlapping structure exceeds the number of copies of the target nucleic acid strand by a sufficient amount that when the first cleavage structure disassociates, the probability that the target strand will associate with an intact copy of the oligonucleotide is greater than the probability that it will associate with a cleaved copy of the oligonucleotide.

In some embodiments, cleavage is performed by a structure-specific nuclease that can recognize and cleave structures that do not have an overlap. In a preferred embodiment, cleavage is performed by a structure-specific nuclease having a lower rate of cleavage of nucleic acid structures that do not comprise an overlap, compared to the rate of cleavage of structures comprising an overlap. In a particularly preferred embodiment, cleavage is performed by a structure-specific nuclease having less than 10% (e.g., less than 1%) of the rate of cleavage of nucleic acid structures that do not comprise an overlap, compared to the rate of cleavage of structures comprising an overlap.

In some embodiments it is desirable to detect the cleavage of the overlapping cleavage structure. Detection may be by analysis of cleavage products or by analysis of one or more of the remaining uncleaved nucleic acids. For convenience, the following discussion will refer to the analysis of cleavage products, but it will be appreciated by those skilled in the art that these methods may as easily be applied to analysis of the uncleaved nucleic acids in an invasive cleavage reaction. Any method known in the art for analysis of nucleic acids, nucleic acid fragments or oligonucleotides may be applied to the detection of cleavage products.

In one embodiment, the cleavage products may be identified by chemical content, e.g., the relative amounts of each atom, each particular type of reactive group or each nucleotide base (Chargaff et al., *J. Biol. Chem.* 177: 405 [1949]) they contain. In this way, a cleavage product may be distinguished from a longer nucleic acid from which it was released by cleavage, or from other nucleic acids.

In another embodiment, the cleavage products may be distinguished by a particular physical attribute, including but not limited to length, mass, charge, or charge-to-mass ratio. In yet another embodiment, the cleavage product may be distinguished by a behavior that is related to a physical attribute, including but not limited to rate of rotation in solution, rate of migration during electrophoresis, coefficient of sedimentation in centrifugation, time of flight in MALDI-TOF mass spectrometry, migration rate or other behavior in chromatography, melting temperature from a complementary nucleic acid, or precipitability from solution.

Detection of the cleavage products may be through release of a label. Such labels may include, but are not limited to one or more of any of dyes, radiolabels such as $^{32}$P or $^{35}$S, binding moieties such as biotin, mass tags, such as metal ions or chemical groups, charge tags, such as polyamines or charged dyes, haptens such as digoxigenin, luminogenic, phosphorescent or fluorogenic moieties, and fluorescent dyes, either alone or in combination with moieties that can suppress or shift emission spectra, such as by fluorescence resonance energy transfer (FRET) or collisional fluorescence energy transfer.

In some embodiments, analysis of cleavage products may include physical resolution or separation, for example by electrophoresis, hybridization or by selective binding to a support, or by mass spectrometry methods such as MALDI-TOF. In other embodiments, the analysis may be performed without any physical resolution or separation, such as by detection of cleavage-induced changes in fluorescence as in FRET-based analysis, or by cleavage-induced changes in the rotation rate of a nucleic acid in solution as in fluorescence polarization analysis.

Cleavage products can be used subsequently in any reaction or read-out method that can make use of oligonucleotides. Such reactions include, but are not limited to, modification reactions, such as ligation, tailing with a template-independent nucleic acid polymerase and primer extension with a template-dependent nucleic acid polymerase. The modification of the cleavage products may be for purposes including, but not limited to, addition of one or more labels or binding moieties, alteration of mass, addition of specific sequences, or for any other purpose that would facilitate analysis of either the cleavage products or analysis of any other by-product, result or consequence of the cleavage reaction.

Analysis of the cleavage products may involve subsequent steps or reactions that do not modify the cleavage products themselves. For example, cleavage products may be used to complete a functional structure, such as a competent promoter for in vitro transcription or another protein binding site. Analysis may include the step of using the completed structure for or to perform its function. One or more cleavage products may also be used to complete an overlapping cleavage structure, thereby enabling a subsequent cleavage reaction, the products of which may be detected or used by any of the methods described herein, including the participation in further cleavage reactions.

Target nucleic acids that may be analyzed using the methods of the present invention that employ a 5' nuclease or other appropriate cleavage agents include both RNA and DNA. Such nucleic acids may be obtained using standard molecular biological techniques. For example, nucleic acids (RNA or DNA) may be isolated from a tissue sample (e.g., a biopsy specimen), tissue culture cells, samples containing bacteria and/or viruses (including cultures of bacteria and/or viruses), etc. The target nucleic acid may also be transcribed in vitro from a DNA template or may be chemically synthesized or amplified by polymerase chain reaction. Furthermore, nucleic acids may be isolated from an organism, either as genomic material or as a plasmid or similar extrachromosomal DNA, or they may be a fragment of such material generated by treatment with a restriction endonuclease or other cleavage agent, or a shearing force, or it may be synthetic.

Assembly of the target, probe, and INVADER oligonucleotide nucleic acids into the cleavage reaction of the present invention uses principles commonly used in the design of oligonucleotide-based enzymatic assays, such as dideoxynucleotide sequencing and polymerase chain reaction (PCR). As is done in these assays, the oligonucleotides are provided in sufficient excess that the rate of hybridization to the target nucleic acid is very rapid. These assays are commonly performed with 50 fmoles to 2 pmoles of each oligonucleotide per microliter of reaction mixture, although they are not necessarily limited to this range. In some preferred embodiments, amounts of oligonucleotides ranging from 250 fmoles to 5 pmoles per microliter of reaction volume are used. Other (e.g., lower) oligonucleotide concentrations commonly used in other molecular biological reactions are also contemplated.

It is desirable that an INVADER oligonucleotide be immediately available to direct the cleavage of each probe oligonucleotide that hybridizes to a target nucleic acid. In some embodiments described herein, the INVADER oligonucleotide is provided in excess over the probe oligonucleotide. While this is an effective means of making the INVADER oligonucleotide immediately available in such embodiments it is not intended that the practice of the present invention be limited to conditions wherein the INVADER oligonucleotide is in excess over the probe, or to any particular ratio of INVADER-to-probe (e.g., in some preferred embodiments described herein, the probe is provided in excess over the INVADER oligonucleotide). Another means of assuring the presence of an INVADER oligonucleotide whenever a probe binds to a target nucleic acid is to design the INVADER oligonucleotide to hybridize more stably to the target, i.e., to have a higher $T_m$ than the probe. This can be accomplished by any of the means of increasing nucleic acid duplex stability discussed herein (e.g., by increasing the amount of complementarity to the target nucleic acid).

Buffer conditions should be chosen that are compatible with both the oligonucleotide/target hybridization and with the activity of the cleavage agent. The optimal buffer conditions for nucleic acid modification enzymes, and particularly DNA modification enzymes, generally included enough mono- and di-valent salts to allow association of nucleic acid strands by base-pairing. If the method of the present invention is performed using an enzymatic cleavage agent other than those specifically described here, the reactions may generally be performed in any such buffer reported to be optimal for the nuclease function of the cleavage agent. In general, to test the utility of any cleavage agent in this method, test reactions are performed wherein the cleavage agent of interest is tested in the MOPS/MnCl$_2$/KCl buffer or Mg-containing buffers described herein and in whatever buffer has been reported to be suitable for use with that agent, in a manufacturer's data sheet, a journal article, or in personal communication.

The INVADER oligonucleotide-directed cleavage reaction is useful to detect the presence of specific nucleic acids. In addition to the considerations listed above for the selection and design of the INVADER and probe oligonucleotides, the conditions under which the reaction is to be performed may be optimized for detection of a specific target sequence.

One objective in optimizing the INVADER oligonucleotide-directed cleavage assay is to allow specific detection of the fewest copies of a target nucleic acid. To achieve this end, it is desirable that the combined elements of the reaction interact with the maximum efficiency, so that the rate of the reaction (e.g., the number of cleavage events per minute) is maximized. Elements contributing to the overall efficiency of the reaction include the rate of hybridization, the rate of cleavage, and the efficiency of the release of the cleaved probe.

The rate of cleavage is a function of the cleavage means chosen, and may be made optimal according to the manufacturer's instructions when using commercial preparations of enzymes or as described in the examples herein. The other elements (rate of hybridization, efficiency of release) depend upon the execution of the reaction, and optimization of these elements is discussed below.

Three elements of the cleavage reaction that significantly affect the rate of nucleic acid hybridization are the concentration of the nucleic acids, the temperature at which the cleavage reaction is performed and the concentration of salts and/or other charge-shielding ions in the reaction solution.

The concentrations at which oligonucleotide probes are used in assays of this type are well known in the art, and are discussed above. One example of a common approach to optimizing an oligonucleotide concentration is to choose a starting amount of oligonucleotide for pilot tests; 0.01 to 2 µM is a concentration range used in many oligonucleotide-based assays. When initial cleavage reactions are performed, the following questions may be asked of the data: Is the reaction performed in the absence of the target nucleic acid substantially free of the cleavage product?; Is the site of cleavage specifically positioned in accordance with the design of the INVADER oligonucleotide?; Is the specific cleavage product easily detected in the presence of the uncleaved probe (or is the amount of uncut material overwhelming the chosen visualization method)?

A negative answer to any of these questions would suggest that the probe concentration is too high, and that a set of reactions using serial dilutions of the probe should be performed until the appropriate amount is identified. Once identified for a given target nucleic acid in a given sample type (e.g., purified genomic DNA, body fluid extract, lysed bacterial extract), it should not need to be re-optimized. The sample type is important because the complexity of the material present may influence the probe concentration optimum.

Conversely, if the chosen initial probe concentration is too low, the reaction may be slow, due to inefficient hybridization. Tests with increasing quantities of the probe will identify the point at which the concentration exceeds the optimum (e.g., at which it produces an undesirable effect, such as background cleavage not dependent on the target sequence, or interference with detection of the cleaved products). Since the hybridization will be facilitated by excess of probe, it is desirable, but not required, that the reaction be performed using probe concentrations just below this point.

The concentration of INVADER oligonucleotide can be chosen based on the design considerations discussed above. In some embodiments, the INVADER oligonucleotide is in excess of the probe oligonucleotide. In a preferred embodiment, the probe oligonucleotide is in excess of the INVADER oligonucleotide.

Temperature is also an important factor in the hybridization of oligonucleotides. The range of temperature tested will depend in large part on the design of the oligonucleotides, as discussed above. Where it is desired to have a reaction be run at a particular temperature (e.g., because of an enzyme requirement, for convenience, for compatibility with assay or detection apparatuses, etc.), the oligonucleotides that function in the reaction can be designed to optimally perform at the desired reaction temperature. Each INVADER reaction includes at least two target sequence-specific oligonucleotides for the primary reaction: an upstream INVADER oligonucleotide and a downstream probe oligonucleotide. In some preferred embodiments, the INVADER oligonucleotide is designed to bind stably at the reaction temperature, while the probe is designed to freely associate and disassociate with the target strand, with cleavage occurring only when an uncut probe hybridizes adjacent to an overlapping INVADER oligonucleotide. In preferred embodiments, the probe includes a 5' flap that is not complementary to the target, and this flap is released from the probe when cleavage occurs. The released flap can be detected directly or indirectly. In some preferred embodiments, as discussed in detail below, the released flap participate as an INVADER oligonucleotide in a secondary reaction.

Optimum conditions for the INVADER assay are generally those that allow specific detection of the smallest amount of a target nucleic acid. Such conditions may be characterized as those that yield the highest target-dependent signal in a given timeframe, or for a given amount of target nucleic acid, or that allow the highest rate of probe cleavage (i.e., probes cleaved per minute). To select a probe sequence that will perform optimally at a pre-selected reaction temperature, the melting temperature ($T_m$) of its analyte specific region (ASR, the region that is complementary to the target nucleic acid) is calculated using the nearest-neighbor model and published parameters for DNA duplex formation (SantaLucia, J., *Proc Natl Acad Sci USA* 95, 1460-5 (1998), Allawi, H. T. & SantaLucia, J., Jr. *Biochemistry* 36, 10581-94 (1997). However, there are several differences between the conditions under which the published parameters were measured and the conditions under which the INVADER assay is run in preferred embodiments. The salt concentrations are often different than the solution conditions in which the nearest-neighbor parameters were obtained (1M NaCl and no divalent metals). One can compensate for this factor by varying the value provided for the salt concentration within the melting temperature calculations. In addition to the salt concentration, the presence of and concentration of the enzyme influences the optimal reaction temperature, and an additional adjustment should be made to the calculated $T_m$ to determine the optimal temperature at which to perform a reaction. By observing the optimal temperature for a number of INVADER assay reactions (i.e., the temperature at which the rate of signal accumulation is highest) it is possible to further alter the value for salt concentration within these calculations to allow the algorithm for $T_m$ calculation to be modified to instead provide an optimal cleavage reaction temperature for a given probe sequence. This additional adjustment is termed a "salt correction." As used herein, the term "salt correction" refers to a variation made in the value provided for a salt concentration, for the purpose of reflecting the effect on a $T_m$ calculation for a nucleic acid duplex of a non-salt parameter or condition affecting said duplex. Variation of the values provided for the strand concentrations will also affect the outcome of these calculations. By using a value of 0.5 M NaCl (Santa-Lucia, J., *Proc Natl Acad Sci USA* 95, 1460-5 [1998]) and strand concentrations of about 1 µM of the probe and 1 fM target, the algorithm used for calculating probe-target melting temperature has been adapted for use in predicting optimal INVADER assay reaction temperature. For a set of about 30 probes, the average deviation between optimal assay temperatures calculated by this method and those experimentally determined was about 1.5° C.

As noted above, the concentration of the cleavage agent can affect the actual optimum temperature for a cleavage reaction. Additionally, different cleavage agents, even if used at identical concentrations, can affect reaction temperature optima differently (e.g., the difference between the calculated probe $T_m$ and the observed optimal reaction temperature may be greater for one enzyme than for another). Determination of appropriate salt corrections for reactions using different enzymes or concentrations of enzymes, or for any other variation made in reaction conditions, involves a two step process of a) measuring reaction temperature optima under the new reaction conditions, and varying the salt concentration within the $T_m$ algorithm to produce a calculated temperature matching or closely approximating the observed optima. Measurement of an optimum reaction temperature generally involves performing reactions at a range of temperatures selected such that the range allows observation of an increase in performance as an optimal temperature is approached (either by increasing or decreasing temperatures), and a decrease in performance when an optimal temperature has been passed, thereby allowing identification of the optimal temperature or temperature range (See e.g., Lyamichev et al., Biochemistry 39:9523 [2000]).

The length of the downstream probe analyte-specific region (ASR) is defined by the temperature selected for running the reaction. To select a probe sequence based on a desired reaction temperature, the probe sequence is selected in the following way (as illustrated for the design of a probe for the detection of a sequence difference at a particular location). Starting from the position of the variant nucleotide on the target DNA, the target base that is paired to the probe nucleotide 5' of the intended cleavage site), an iterative procedure is used by which the length of the ASR is increased by one base pair until a calculated optimal reaction temperature ($T_m$ plus salt correction to compensate for enzyme and any other reaction conditions effects) matching the desired reaction temperature is reached. The noncomplementary arm of the probe is preferably selected (by a similar iterative process) to allow the secondary reaction to cycle at the same reaction temperature, and the entire probe design (ASR and 5' noncomplementary arm) is screened using programs such as mfold (Zuker, Science 244, 48-52 [1989]) or Oligo 5.0 (Rychlik and Rhoads, Nucleic Acids Res. 17:8543 [1989]) for the possible formation of dimer complexes or secondary structures that could interfere with the reaction. The same principles are also followed for INVADER oligonucleotide design. The following describes design of an INVADER assay embodiment wherein the 3' end of the INVADER oligonucleotide, at a position N on the target DNA, is designed to have a nucleotide not complementary to either allele suspected of being contained in the sample to be tested. The mismatch does not adversely affect cleavage (Lyamichev et al. Nature Biotechnology 17:292 [1999]), and it can enhance probe cycling, presumably by minimizing coaxial stabilization effects between the two probes. Briefly, starting from the position N, additional residues complementary to the target DNA starting from residue N-1 are then added in the upstream direction until the stability of the INVADER-target hybrid exceeds that of the probe (and therefore the planned assay reaction temperature). In preferred embodiments, the stability of the INVADER-target hybrid exceeds that of the probe-target hybrid by 15-20° C.

In some embodiments, where the released cleavage fragment from a primary reaction is to be used in a secondary reaction, one should also consider the reaction conditions of the secondary reaction in designing the oligonucleotides for the primary reaction (e.g., the sequence of the released non-complementary 5' flap of the probe in the primary reaction can be designed to optimally function in a secondary reaction). For example, in some embodiments, a secondary reaction is used where the released cleavage fragment from a primary reaction hybridizes to a synthetic cassette to form a secondary cleavage reaction. In some preferred embodiments, the cassette comprises a fluorescing moiety and a quenching moiety, wherein cleavage of the secondary cleavage structure separates the fluorescing moiety from the quenching moiety, resulting in a detectable signal (e.g., FRET detection). The secondary reaction can be configured a number of different ways. For example, in some embodiments, the synthetic cassette comprises two oligonucleotides: an oligonucleotide that contains the FRET moieties and a FRET/INVADER oligonucleotide bridging oligonucleotide that allows the INVADER oligonucleotide (i.e., the released flap from the primary reaction) and the FRET oligonucleotide to hybridize thereto, such that a cleavage structure is formed. In some embodiments, the synthetic cassette is provided as a single oligonucleotide, comprising a hairpin structure (i.e., the FRET oligonucleotide is connected at its 3' end to the bridging oligonucleotide by a loop). The loop may be nucleic acid, or a non-nucleic acid spacer or linker. The linked molecules may together be described as a FRET cassette. In the secondary reaction using a FRET cassette the released flap from the primary reaction, which acts as an INVADER oligonucleotide, should be able to associate and disassociate with the FRET cassette freely, so that one released flap can direct the cleavage of multiple FRET cassettes. It is one aspect of the assay design that all of the probe sequences may be selected to allow the primary and secondary reactions to occur at the same optimal temperature, so that the reaction steps can run simultaneously. In an alternative embodiment, the probes may be designed to operate at different optimal temperatures, so that the reactions steps are not simultaneously at their temperature optima. As noted above, the same iterative process used to select the ASR of the probe can be used in the design of the portion of the primary probe that participates in a secondary reaction.

Another determinant of hybridization efficiency is the salt concentration of the reaction. In large part, the choice of solution conditions will depend on the requirements of the cleavage agent, and for reagents obtained commercially, the manufacturer's instructions are a resource for this information. When developing an assay utilizing any particular cleavage agent, the oligonucleotide and temperature optimizations described above should be performed in the buffer conditions best suited to that cleavage agent.

A "no enzyme" control allows the assessment of the stability of the labeled oligonucleotides under particular reaction conditions, or in the presence of the sample to be tested (e.g., in assessing the sample for contaminating nucleases). In this manner, the substrate and oligonucleotides are brought together (e.g., in a tube, on a chip, etc.) with all desired reaction components, except the enzyme and treated the same as the enzyme-containing reactions. Other controls may also be included. For example, a reaction with all of the components except the target nucleic acid will serve to confirm the dependence of the cleavage on the presence of the target sequence. In some embodiments of the present invention, assay design is carried out using INVADERCREATOR software (Third Wave Technologies, Madison, Wis.), which calculates ideal oligonucleotide sequences and reaction conditions for conducting invasive cleavage reactions.

Cleavage agents are selected to provide the desired assay outcome, depending on a number of factors, including the type of target sequence. Some 5' nucleases do not require an upstream oligonucleotide to be active in a cleavage reaction. Although cleavage may be slower without the upstream oligonucleotide, it may still occur (Lyamichev et al., Science 260:778 [1993], Kaiser et al., J. Biol. Chem., 274:21387 [1999]). When a DNA strand is the template or target strand to which probe oligonucleotides are hybridized, the 5' nucleases derived from DNA polymerases and some flap endonucleases (FENs), such as that from *Methanococcus jannaschii*, can cleave quite well without an upstream oligonucleotide providing an overlap (Lyamichev et al., Science 260:778 [1993], Kaiser et al., J. Biol. Chem., 274: 21387 [1999], and U.S. Pat. No. 5,843,669, herein incorporated by reference in its entirety). These nucleases may be selected for use in some embodiments of the INVADER assay, e.g., in embodiments wherein cleavage of the probe in the absence of an INVADER oligonucleotide gives a different cleavage product, which does not interfere with the intended analysis, or wherein both types of cleavage, INVADER oligonucleotide-directed and INVADER oligonucleotide-independent, are intended to occur.

In other embodiments it is preferred that cleavage of the probe be dependent on the presence of an upstream INVADER oligonucleotide, and enzyme having this requirement would be used. Other FENs, such as those from *Archeaoglobus fulgidus* (Afu) and *Pyrococcus furiosus* (Pfu), cleave an overlapped structure on a DNA target at so much greater a rate than they do a non-overlapping structure (i.e., either missing the upstream oligonucleotide or having a non-overlapping upstream oligonucleotide) that they can be viewed as having an essentially absolute requirement for the overlap (Lyamichev et al., Nat. Biotechnol., 17:292 [1999], Kaiser et al., J. Biol. Chem., 274:21387 [1999]). When an RNA target is hybridized to DNA oligonucleotide probes to form a cleavage structure, many FENs cleave the downstream DNA probe poorly, regardless of the presence of an overlap. On such an RNA-containing structure, the 5' nucleases derived from DNA polymerases have a strong requirement for the overlap, and are essentially inactive in its absence.

In some embodiments, additional components may be used in an invasive cleavage reaction. For example, in some embodiments (e.g., embodiments where the target is RNA) an ARRESTOR oligonucleotide is employed per the teachings PCT Publication WO98/42873.

C. Formats for INVADER Assay on a Solid Support

The present invention is not limited to a particular configuration of the INVADER assay. Any number of suitable configurations of the component oligonucleotides may be utilized. For example, in some embodiments of the present invention, the probe oligonucleotide is bound to a solid support and the INVADER oligonucleotide and DNA (or RNA) target are provided in solution. In other embodiments of the present invention, the INVADER oligonucleotide is bound to the support and the probe and target are in solution. In yet other embodiments, both the probe and INVADER oligonucleotides are bound to the solid support. In further embodiments, the target nucleic acid is bound directly or indirectly (e.g., through hybridization to a bound oligonucleotide that is not part of a cleavage structure) to a solid support, and either or both of the probe and INVADER oligonucleotides are provided either in solution, or bound to a support. In still further embodiments, a primary INVADER assay reaction is carried out in solution and one or more components of a secondary reaction are bound to a solid support. In yet other embodiments, all of the components necessary for an INVADER assay reaction, including cleavage agents, are bound to a solid support.

The present invention is not limited to the configurations described herein. Indeed, one skilled in the art recognizes that any number of additional configurations may be utilized. Any configuration that supports a detectable invasive cleavage reaction may be utilized.

1. Probe Oligonucleotide Bound

In some embodiments, the probe oligonucleotide is bound to a solid support. In some embodiments, the probe is a labeled signal probe oligonucleotide. The signal probe is cleaved to release a signal molecule indicative of the presence of a given target molecule. In some embodiments, the signal molecule is a fluorescence donor in an energy transfer reaction (e.g., FRET), whose emission increases in response to separation from a quenching fluorescence acceptor. In other embodiments, the signal molecule is a fluorescent moiety that is detected only upon its release into solution. It yet other embodiments, the signal molecule is a fluorescently labeled small molecule that is separated from the full length Signal Probe by carrying a distinct charge.

In some embodiments, a system is designed in which no separation steps are required to visualize the signal generated by the reaction. In some embodiments, this is accomplished in the FRET system in which the fluorescence donor remains affixed to the solid support following cleavage of the signal probe. This design has several complexities that stem from the nature of the FRET reaction. The quenching in the FRET signal molecule is only 97-99% efficient (i.e. not all of the energy emitted by the donor will be absorbed by the quencher). To detect the fluorescence of the unquenched donor above the background of the uncleaved probes, it is necessary to cleave 1-3% of the probe molecules. Assuming that in a 100 µm×100 µm area, there are ~$10^8$ probes bound, then ~$10^6$ should be cleaved to generate a signal detectable above the inherent background generated by those probes. Probe cycling in an INVADER assay reaction on a single target molecule can generate approximately 1000-2000 cleaved probe molecules per hour (assuming a turnover rate of 15-30 events/target/min). Roughly 1000 target molecules are required to generate this level of cleaved signal probes. Assuming a reaction volume of 1 nL, the necessary target concentration becomes 1 pM, well within the range of the maximum that can be manipulated (e.g., 0.5-2.5 pM). At less than maximal probe densities, it would nonetheless be necessary to deliver at least 10-20 target molecules (i.e. a 10-20 fM solution) to each reaction area to ensure a statistical likelihood that each will contain target. The same target concentration considerations apply to other, non-FRET alternatives, for example, release of a single fluorescent group into solution, with or without a quenching fluorophore and release of a positively charged signal molecule even though <1% cleavage would be detectable with these other methods. Accordingly, in some embodiments, dilute solutions are used in conjunction with longer reaction times (e.g. a 100 fM solution could be applied and the reactions run for 10-24 hours).

Figure 6:
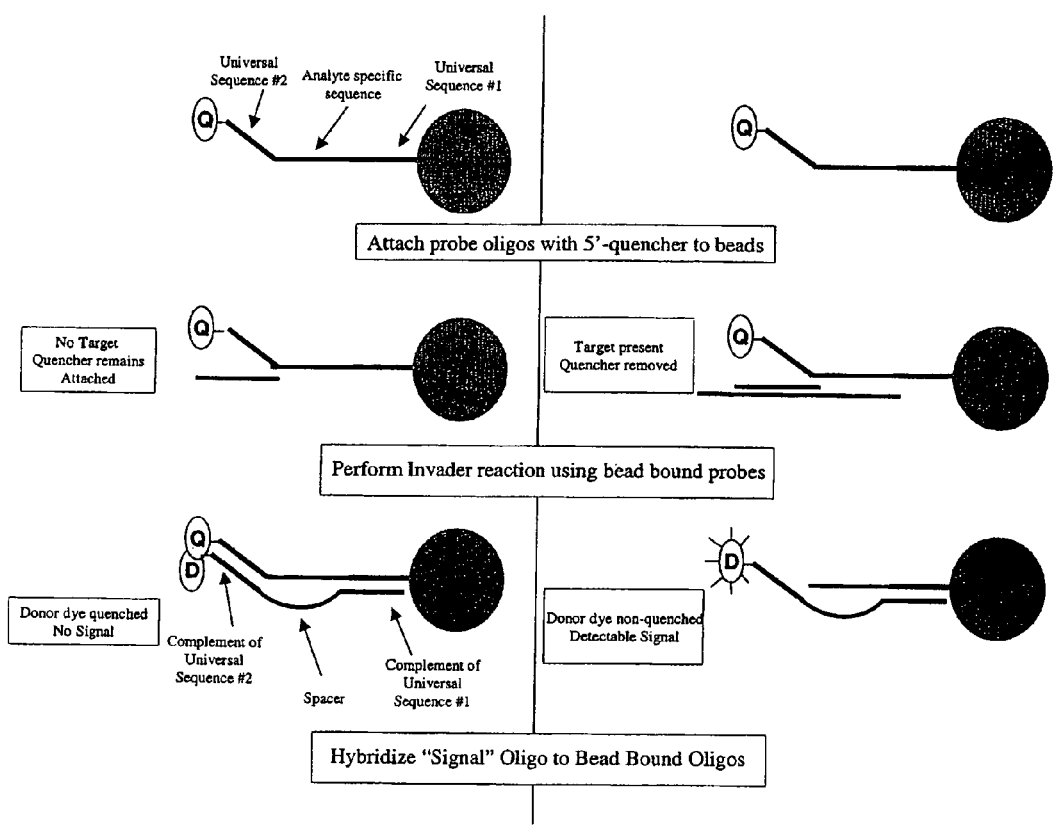
FIG. 6 shows a schematic diagram of invasive cleavage reactions in some embodiments of the present invention.

In some embodiments, the probe is designed with a 5' quencher group, with the 3' end of the probe attached to a solid surface. When the target nucleic is present in a sample, the 5' quencher group is released. An oligonucleotide bearing a dye is then introduced, wherein the oligonucleotide binds to the probe. The dye is quenched in samples without the target nucleic acid while the dye is not quenched in sample where the quencher had been released in the presence of a target nucleic acid. An example of such an embodiment is shown in FIG. 6. The probe in this example contains a quencher group (Q) attached to a universal sequence (e.g., a 5' flap sequence that may be used in conjunction with any probe). The middle portion of the probe contains an analyte-specific sequence that is complementary to the target nucleic acid. The 3' portion of the probe is attached to a solid surface and contains a second universal sequence (shown as Universal Sequence #1 in FIG. 6). The middle of FIG. 6 shows examples of structures formed in the presence of an INVADER oligonucleotide and in the presence or absence of a target nucleic acid. In the left panel, no target is present and no cleavage occurs. In the right panel, a target nucleic is present, forming an invasive cleavage structure and resulting in the cleavage of the 5' flap, which is then released. In the bottom portion of FIG. 6, an oligonucleotide is introduced that is capable of hybridizing to the probe only when the 5' flap is present. The oligonucleotide contains a dye linked to a universal sequence that is complementary to the 5' flap of the probe, a spacer molecule (See e.g., U.S. Pat. Nos. 6,210,880 and 6,194,149, herein incorporated by reference in their entireties, for a description of spacer molecules used in such bridging oligonucleotides), and a universal sequence that is complementary to the "Universal Sequence #1" shown in FIG. 6. Where a target nucleic acid is present and the 5' flap has been removed, the oligonucleotide binds but is unquenched, producing a detectable signal. Where a target nucleic is not present, the 5' flap remains associated with the probe and the dye on the oligonucleotide is quenched, producing little or no detectable signal.

In some embodiments, the sequence indicated as "Universal Sequence #1" is not present. Thus, the probe simply contains the 5' flap with a quencher group and a analyte-specific sequence and the additional oligonucleotide contains a sequence complementary to the 5' flap and the analyte specific sequence. In some such embodiments, the probe is attached to the solid surface though a linker group (e.g., ten C18 spacers linked to biotin (Glen Research)). For illustration purposes, probe sequences that find use in the detection of the ApoE arg allele include:

5'-dabcyl-cgcgccgaggGcttctgcaggtcatcgg-(C18×10)-biotin-3' (SEQ ID NO:10)

5'-dabcyl-cgcgccgaggGcttctgcaggtcatcgg-biotin-3' (SEQ ID NO:11)

5'-BHQ1-cgcgccgaggGcttctgcaggtcatcgg-(C18×10)-biotin-3' (SEQ ID NO:12)

5'-BHQ2-cgcgccgaggGcttctgcaggtcatcgg-(C18×10)-biotin-3' (SEQ ID NO:13)

5'-cg$^{/BHQ2\backslash}$cgccgaggGcttctgcaggtcatcgg-(C18×10)-biotin-3' (SEQ ID NO:14)

5'-cg$^{/BHQ}$2\cgccgaggGcttctgcaggtcatcgg-(C18×10)-biotin-3' (SEQ ID NO:15)

where BHQ1 is black hole quencher #1 and BHQ2 is black hole quencher #2 (Biosearch Technologies, Inc., Novato, Calif.).

2. INVADER Oligonucleotide Bound

In some embodiment of the present invention, the INVADER oligonucleotide is bound to the solid support and the probe oligonucleotide is free in solution. In this embodiment, there are no restrictions on the length of the INVADER oligonucleotide-target duplex, since the INVADER oligonucleotide does not need to cycle on and off the target, as does the signal probe. Thus, in some embodiments where the INVADER oligonucleotide is bound to a solid support, the INVADER oligonucleotide is used as a "capture" oligonucleotide to concentrate target molecules from solution onto the solid phase through continuous application of sample to the solid support. For example, by applying 1 ml of a 1 mg/ml target solution, it is possible to bind $10^6$-$10^8$ target molecules in a 100 μm×100 μm area. Moreover, because the INVADER oligonucleotide-target interaction is designed to be stable, in some embodiments, the support is washed to remove unbound target and unwanted sample impurities prior to applying the signal probes, enzyme, etc., to ensure even lower background levels. In other embodiments, a capture oligonucleotide complementary to a distinct region in the proximity of the locus being investigated is utilized.

Several possibilities exist for separation of cleaved from uncleaved signal probes where INVADER oligonucleotides are bound to the solid support and signal probe oligonucleotides are free in solution. In preferred embodiments, a labeling strategy is utilized that makes it possible to chemically differentiate cleaved from uncleaved probe since both full length and cleaved probes are in solution. For example, in some embodiments (e.g., using FRET signal probes), full-length probe is quenched but the cleavage product generates fluorescent signal. In other embodiments (e.g., charge separation techniques described below), the full-length probe is negatively charged but the cleaved probe is positively charged. In such embodiments, the cleaved signal probes generated by the charge separation approach are actively captured on a negatively charged electrode. This capture results in partitioning from uncleaved molecules as well as concentration of the labeled, cleaved probes by as much as an order of magnitude. Second, the use of an electric field to capture the cleaved probe eliminates the need to micromachine tiny wells to prevent diffusion of the cleaved probes.

3. Both Probe and INVADER Oligonucleotide Bound

In some embodiments of the present invention, both a probe and an INVADER oligonucleotide are bound to a solid support. In preferred embodiments, probe and INVADER oligonucleotides are placed in close proximity on the same solid support such that a target nucleic acid may bind both the probe and INVADER oligonucleotides. In some embodiments, the oligonucleotides are attached via spacer molecules in order to improve their accessibility and decrease interactions between oligonucleotides.

In some preferred embodiments, a single INVADER oligonucleotide is configured to allow it to contact and initiate multiple cleavage reactions. For example, in some embodiments, one INVADER oligonucleotide is surrounded on a solid support by multiple signal probe oligonucleotides. A target nucleic acid binds to an INVADER oligonucleotide and a probe oligonucleotide. The signal probe is cleaved (generating signal) and released, leaving the target bound to the INVADER oligonucleotide. This target:INVADER oligonucleotide complex is then able to contact another signal probe and promote another cleavage event. In this manner, the signal generated from one target and one INVADER oligonucleotide is amplified.

In other embodiments, the probe and INVADER oligoucleotides are combined in one molecule. The connection between the probe and INVADER oligonucleotide portions of the single molecule may be nucleic acid, or may be a non-nucleic acid linker (e.g., a carbon linker, a peptide chain, etc.).

4. Secondary Reaction Bound

In some embodiments, a primary INVADER assay reaction is performed in solution and a secondary reaction is performed on a solid support. Cleaved probes from the primary INVADER assay reaction are contacted with a solid support containing one or more components of a cleavage structure, including but not limited to a secondary target nucleic acid, a secondary probe or a secondary INVADER oligonucleotide. In a preferred embodiment, the component is a one-piece secondary oligonucleotide, or cassette, comprising both a secondary target portion and a secondary probe portion. In a particularly preferred embodiment, the cassette is labeled to allow detection of cleavage of the cassette by a FRET mechanism. The secondary signal oligonucleotide may be labeled using any suitable method including, but not limited to, those disclosed herein. It will be appreciated that any of the embodiments described above for configuring an INVADER assay reaction on a support may be used in configuring secondary or subsequent INVADER assay reactions on a support.

5. Target Bound

In some embodiments of the present invention, the target nucleic acid (e.g., genomic DNA) is bound to the solid support. In some embodiments, the INVADER and probe oligonucleotides are free in solution. In other embodiments, the target nucleic acid, the INVADER oligonucleotide, and the probe (e.g., signal probe) oligonucleotides are bound. In yet other embodiments, a secondary oligonucleotide (e.g., a FRET oligonucleotide) is included in the reaction. In some embodiments, the FRET oligonucleotide is free in solution. In other embodiments, the FRET oligonucleotide is bound to the solid support.

6. Enzyme Bound

In some embodiments, the cleavage agent (e.g., enzyme) is bound to a solid support. In some embodiments, the target nucleic acid, probe oligonucleotide, and INVADER oligonucleotide are provided in solution. In other embodiments, one or more of the nucleic acids is bound to the solid support. Any suitable method may be used for the attachment of a cleavage enzyme to a solid support, including, but not limited to, covalent attachment to a support (See e.g., Chernukhin and Klenova, Anal. Biochem., 280:178 [2000]), biotinylation of the enzyme and attachment via avidin or streptavidin (See e.g., Suter et al., Immunol. Lett. 13:313 [1986]), and attachment via antibodies (See e.g., Bilkova et al., J. Chromatogr. A, 852:141 [1999]).

D. Spacers

In some embodiments of the present invention, oligonucleotides are attached to a solid surface via a spacer or linker molecule. The present invention is not limited to any one mechanism. Indeed, an understanding of the mechanism is not necessary to practice the present invention. Nonetheless, it is contemplated that spacer molecules enhance INVADER assay reactions by improving the accessibility of oligonucleotides and decreasing interactions between oligonucleotides. The use of linkers, which can be incorporated during oligonucleotide synthesis, has been shown to increase hybridization efficiency relative to capture oligonucleotides that contain no linkers (Guo et al., Nucleic Acids Res., 22:5456 [1994]; Maskos and Southern, Nucleic Acids Res., 20:1679 [1992]; Shchepinov et al., Nucleic Acids Research 25:1155 [1997]).

Spacer molecules may be comprised of any suitable material. Preferred materials are those that are stable under reaction conditions utilized and non-reactive with the components of the INVADER assay. Suitable materials include, but are not limited to, carbon chains (e.g., including but not limited to $C_{18}$), polynucleotides (e.g., including, but not limited to, polyl, polyT, polyG, polyC, and polyA), and polyglycols (e.g., hexaethylene glycol).

Spacer molecules may be of any length. Accordingly in some embodiments, multiple spacer molecules are attached end to end to achieve the desired length spacer. For example, in some embodiments, multiple $C_{18}$ or hexaethylene glycol spacers (e.g., including, but not limited to, 5, 10, or 20 spacer molecules) are combined. The optimum spacer length is dependent on the particular application and solid support used. To determine the appropriate length, different lengths are selected (e.g., 5, 10, or 20 $C_{18}$ or hexaethylene glycol spacers molecules or multiple polyglycols) and reactions are performed as described herein to determine which spacer gives the most efficient reaction.

E. Solid Supports

The present invention is not limited to any one solid support. In some embodiments, reactions are performed on microtiter plates (e.g., polystyrene plates containing 96 or 384 wells). For example, in some embodiments, streptavidin (SA) coated 96-well or 384-well microtiter plates (Boehringer Mannheim Biochemicals, Indianapolis, Ind.) are used as solid supports. In such embodiments, signal can be measured using standard fluorescent, chemiluminescent or colorimetric microtiter plate readers.

In some embodiments, INVADER assay reactions are carried out on particles or beads. The particles can be made of any suitable material, including, but not limited to, latex. In some embodiments, columns containing a particle matrix suitable for attachment of oligonucleotides are used. In some embodiments, reactions are performed in minicolumns (e.g. DARAS, Tepnel, Cheshire, England). The columns contain microbeads to which oligonucleotides are covalently bound and subsequently used as capture probes or in enzymatic reactions. The use of minicolumns allows approximation of the bound oligonucleotide concentrations that will be attainable in a miniaturized chip format. Oligonucleotide binding is limited by the capacity of the support. Thus, bound oligonucleotide concentration can only be increased by increasing the surface area to volume ratio of the reaction vessel. For example, one well of a 96-well microtiter plate, with a surface area of ~1 $cm^2$ and a volume of 400 μl has a maximal bound oligonucleotide concentration of ~25 nM. On the other hand, a 100 μm×100 μm×100 μm volume in a microchip has a surface area of $10^4$ $\mu m^2$ and a volume of 1 nL, resulting in a bound oligonucleotide concentration of 0.2 µM. Similar increased surface area:volume ratios can be obtained by using microbeads. Given a binding capacity of $\geq 10^{14}$ oligonucleotides in a 30 µl volume, these beads allow bound oligonucleotide concentrations of 0.2-10 µM, i.e. comparable to those anticipated for microchips. In some embodiments, beads or other microparticles of the present invention are analysed using flow cytometry (e.g., FACS analysis). Microparticles have been used as a solid phase in flow cytometric assays (e.g., U.S. Pat. No. 5,981,180, hereby incorporated by reference). It is contemplated that the detection assay sensitivity is increased with flow cytometric detection, as individual particles may be detected instead of bulk suspensions.

In some embodiments, INVADER reactions are carried out on a HydroGel (Packard Instrument Company, Meriden, Conn.) support. HydroGel is porous 3D hydrophilic polymer matrix. The matrix consists of a film of polyacrylamide polymerized onto a microscope slide. A coupling moiety is co-polymerized into the matrix that permits the immobilization of aminated oligonucleotide molecules by reductive amination. Covalent attachment by amine groups permits the immobilization of nucleic acid probes at specific attachment points (usually their ends), and the hydrogel provides a 3D matrix approximating a bulk solution phase, avoiding a solid/solution phase interface.

In other embodiments, INVADER reactions are conducted on a solid support using a BEADARRAY (Illumina, San Diego, Calif.) technology. The technology combines fiber optic bundles and beads that self-assemble into an array. Each fiber optic bundle contains thousands to millions of individual fibers depending on the diameter of the bundle. Sensors are affixed to each bead in a given batch. The particular molecules on a bead define that bead's function as a sensor. To form an array, fiber optic bundles are dipped into pools of coated beads. The coated beads are drawn into the wells, one bead per well, on the end of each fiber in the bundle.

The present invention is not limited to the solid supports described above. Indeed, a variety of other solid supports are contemplated including, but not limited to, glass microscope slides, glass wafers, gold, silicon, microchips, and other plastic, metal, ceramic, or biological surfaces.

F. Surface Coating and Attachment Chemistries

In some embodiments of the present invention, solid supports are coated with a material to aid in the attachment of oligonucleotides. The present invention is not limited to any one surface coating. Indeed, a variety of coatings are contemplated including, but not limited to, those described below.

In some embodiments, solid support INVADER assay reactions are carried out on solid supports coated with gold. The gold can be attached to any suitable solid support including, but not limited to, microparticles, microbeads, microscope slides, and microtiter plates. In some embodiments, the gold is functionalized with thiol-reactive maleimide moieties that can be reacted with thiol modified DNA (See e.g., Frutos et al., Nuc. Acid. Res., 25:4748 [1997]; Frey and Corn, Analytical Chem, 68:3187 [1996]; Jordan et al., Analytical Chem, 694939 [1997]; and U.S. Pat. No. 5,472,881; herein incorporated by reference).

In other embodiments, solid support INVADER assay reactions are carried out on supports coated with silicon. The silicon can be attached to any suitable support, including, but not limited to, those described above and in the illustrative examples provided below.

Additionally, in some embodiments, solid supports are coated with a molecule (e.g., a protein) to aid in the attachment of nucleic acids. The present invention is not limited to any particular surface coating. Any suitable material may be utilized including, but not limited to, proteins such as streptavidin. Thus, in some embodiments, oligonucleotides are attached to solid supports via terminal biotin or $NH_2$-mediated linkages included during oligonucleotide synthesis. In preferred embodiments, INVADER oligonucleotides are attached to the support at their 5' ends and signal probes are attached at their 3' ends. In some embodiment, oligonucleotides are attached via a linker proximal to the attachment point. In a preferred embodiment, attachment is via a 40 atom linker with a low negative charge density as described in Schepinov et al. (Nucleic Acids Research 25:1155 [1997]).

In other embodiments, oligonucleotides are attached to solid support via antigen:antibody interaction. For Example, in some embodiments, an antigen (e.g., protein A or Protein G) is attached to a solid support and IgG is attached to oligonucleotides. In other embodiments, IgG is attached to a solid support and an antigen (e.g., Protein A or Protein G) is attached to oligonucleotides.

G. Addressing of Oligonucleotides

In some embodiments, oligonucleotides are targeted to specific sites on the solid support. Any number of techniques for the addressing of oligonucleotides may be utilized. For example, in some embodiments, solid support surfaces are electrically polarized at one given site in order to attract a particular DNA molecule (e.g., Nanogen, CA, See e.g., U.S. Pat. Nos. 5,605,662, 5,632,957, 5,849,486, 5,929,208, 5,965,452, 6,017,696, 6,048,690, 6,051,380, 6,068,818, 6,071,394, 6,099,803, 6,129,828, 6,162,603, 6,225,059, 6,238,624, 6,245,508, 6,245,827, and 6,258,606, and PCT Publications WO 01/34765, WO 01/23082, WO 01/13126, WO 01/06496, WO 00/62036, WO 00/61818, WO 00/61817, WO 00/61805, WO 00/61803, WO 00/60919, and WO 00/58522 herein incorporated by reference in their entireties). In other embodiments, a pin tool may be used to load the array mechanically (Shalon, Genome Methods, 6:639 [1996]). In other embodiments, ink jet technology is used to print oligonucleotides onto an active surface (e.g., O'Donnelly-Maloney et al., Genetic Analysis:Biomolecular Engineering, 13:151 [1996]).

In some preferred embodiments utilizing gold surfaces, the gold surfaces are further modified to create addressable DNA arrays by photopatterning self-assembled monolayers to form hydrophilic and hydrophobic regions. Alkanethiol chemistry is utilized to create self-assembled monolayers (Nuzzo et al., JACS, 105:4481 [1983]). DNA is placed on the hydrophilic regions by using an automated robotic device (e.g., a pin-loading tool).

H. Detection

In some embodiments of the present invention, products of an INVADER assay reaction are detected using any suitable method. For example, in some embodiments, a signal probe is utilized for the detection of cleavage products. In some embodiments, the signal probe comprises a fluorescent moiety and a quenching moiety (e.g., a FRET signal probe). Cleavage results in the separation of the quenching group from the fluorescent group, thus generating signal. In other embodiments, cleavage is detected using charge-based separation (e.g., the uncleaved and cleaved signal probes have different charges).

However, the present invention is not limited to any particular detection method. Indeed, a variety of additional methods are contemplated, including, but not limited to, scanning probe microscopy, atomic force microscopy, confocal microscopy, scanning tunneling microscopy, angle-dependent x-ray photoelectron spectroscopy, and Auger electron spectroscopy. For example, in some embodiments, thiol-modified oligonucleotides are attached to gold surfaces (See e.g., U.S. Pat. No. 5,472,881; herein incorporated by reference) and detection of cleavage is accomplished using scanning tunneling microscopy or atomic force microscopy. These techniques make it possible to visualize individual atoms in a DNA molecule. For example, in some embodiments, cleaved probe molecules are distinguished from uncleaved probe molecules on the basis of size. Instruments for the microscopy techniques disclosed herein are available commercially (e.g., Thermomicroscopes, Sunnyvale, Calif.).

In other embodiments, signal probe cleavage may be characterized by ellipsometry. For example, in some embodiments, signal probes are labeled with a biotin or other hapten allowing attachment of an enzyme such as peroxidase. Attachment of a peroxidase to a surface allows deposition of an insoluble thin film that can be detected and quantitated using an instrument such as a fixed polarizer ellipsometer (See e.g., Ostroff et al., Clinical Chem., 45:1659 [1999]), which can sensitively detect perturbations in the layer such as those created by cleavage of a labeled probe. One skilled in the relevant art recognizes that any number of additional suitable methods may be utilized to detect products of an INVADER assay reaction.

I. Activity Assays

In some embodiments, the parameters of solid-phase INVADER assay system are optimized using a model system. Initial characterization of INVADER assay performance may be done using short double-stranded PCR products or synthetic oligonucleotide as substrates. In some embodiments, the hybridization reaction time and temperature may be optimized. In other embodiments, sheared genomic DNA may be added to investigate interference with the specific reaction from any competing sequences present.

In some embodiments, it may be useful to compare the performance of variously configured INVADER assay reactions in the presence of a solid support. Different reaction supports may differently affect the rate of cleavage observed in an INVADER assay reaction (e.g., due to differences in the interactions between the support and one or more reactions components). For example, significant differences in the cleavage rate may indicate impaired access of the enzyme to the cleavage sites bound to the support, or may indicate some other inhibition of the enzyme. In some embodiments, a support may be pre-washed before exposure to the reaction components, as one way of determining if the support has inhibiting factors that may be removed by washing. In other embodiments, the support may be pretreated with carriers, (e.g., agents that are chemically similar to reaction components but which are not intended to participate in the INVADER assay reaction), for the purpose of neutralizing or occupying support factors that might otherwise interact with reaction components. For example, supports may be pretreated with a protein such as BSA or a nucleic acid such as yeast tRNA, both commonly used carriers, to reduce unintended interactions between the support and its associated factors and the protein or nucleic acid components of the INVADER assay reaction, respectively. In some embodiments, carriers are added directly to the reaction mixture, instead of, or in addition to their use in pretreatment of a support. Carriers may be used alone, as described above, or they may be combined (e.g., protein and nucleic acid carriers may be combined in a single pretreatment of a support). Use of carriers in the treatment of supports and in the optimization of reactions is not limited to those cited above. Many carriers for protein and nucleic acid-based reactions are known in the art.

J. Fractionation of Specific Nucleic Acids by Selective Charge Separation

Some nucleic acid-based detection assays involve the elongation and/or shortening of oligonucleotide probes. For example, as described herein, the INVADER assay involves the cleavage (i.e., shortening) of oligonucleotides as a means for detecting the presence of a target nucleic sequence. Examples of other detection assays that involve the shortening of an oligonucleotide probe include the "TAQMAN" or nick-translation PCR assay described in U.S. Pat. No. 5,210,015 to Gelfand et al. (the disclosure of which is herein incorporated by reference), the assays described in U.S. Pat. Nos. 4,775,619 and 5,118,605 to Urdea (the disclosures of which are herein incorporated by reference), the catalytic hybridization amplification assay described in U.S. Pat. No. 5,403,711 to Walder and Walder (the disclosure of which is herein incorporated by reference), and the cycling probe assay described in U.S. Pat. Nos. 4,876,187 and 5,011,769 to Duck et al. (the disclosures of which are herein incorporated by reference). Examples of detection assays that involve the elongation of an oligonucleotide probe (or primer) include the polymerase chain reaction (PCR) described in U.S. Pat. Nos. 4,683,195 and 4,683,202 to Mullis and Mullis et al. (the disclosures of which are herein incorporated by reference) and the ligase chain reaction (LCR) described in U.S. Pat. Nos. 5,427,930 and 5,494,810 to Birkenmeyer et al. and Barany et al. (the disclosures of which are herein incorporated by reference). The above examples are intended to be illustrative of nucleic acid-based detection assays that involve the elongation and/or shortening of oligonucleotide probes and do not provide an exhaustive list.

Typically, nucleic acid-based detection assays that involve the elongation and/or shortening of oligonucleotide probes require post-reaction analysis to detect the products of the reaction. It is common that the specific reaction product(s) must be separated from the other reaction components, including the input or unreacted oligonucleotide probe. One detection technique involves the electrophoretic separation of the reacted and unreacted oligonucleotide probe. When the assay involves the cleavage or shortening of the probe, the unreacted product will be longer than the reacted or cleaved product. When the assay involves the elongation of the probe (or primer), the reaction products will be greater in length than the input. Gel-based electrophoresis of a sample containing nucleic acid molecules of different lengths separates these fragments primarily on the basis of size. This is due to the fact that in solutions having a neutral or alkaline pH, nucleic acids having widely different sizes (i.e., molecular weights) possess very similar charge-to-mass ratios and do not separate (Andrews, Electrophoresis, 2nd Edition, Oxford University Press (1986), pp. 153-154). The gel matrix acts as a molecular sieve and allows nucleic acids to be separated on the basis of size and shape (e.g., linear, relaxed circular or covalently closed supercoiled circles).

Unmodified nucleic acids have a net negative charge due to the presence of negatively charged phosphate groups contained within the sugar-phosphate backbone of the nucleic acid. Typically, the sample is applied to gel near the negative pole and the nucleic acid fragments migrate into the gel toward the positive pole with the smallest fragments moving fastest through the gel.

The present invention provides a means for fractionating nucleic acid fragments on the basis of charge. This separation technique is related to the observation that positively charged adducts can affect the electrophoretic behavior of small oligonucleotides because the charge of the adduct is significant relative to charge of the whole complex. In addition to the use of positively charged adducts (e.g., Cy3 and Cy5 fluorescent dyes), the oligonucleotide may contain amino acids (particularly useful amino acids are the charged amino acids: lysine, arginine, asparate, glutamate), modified bases, such as amino-modified bases, and/or a phosphonate backbone (at all or a subset of the positions). In other embodiments, as discussed further below, a neutral dye or detection moiety (e.g., biotin, streptavidin, etc.) may be employed in place of a positively charged adduct, in conjunction with the use of amino-modified bases and/or a complete or partial phosphonate backbone.

This observed effect is of particular utility in assays based on the cleavage of DNA molecules. Using the assays described herein as an example, when an oligonucleotide is shortened through the action of a cleavage agent, the positive charge can be made to not only significantly reduce the net negative charge, but to actually override it, effectively "flipping" the net charge of the labeled entity. This reversal of charge allows the products of target-specific cleavage to be partitioned from uncleaved probe by extremely simple means. For example, the products of cleavage can be made to migrate towards a negative electrode placed at any point in a reaction vessel, for focused detection without gel-based electrophoresis. When a slab gel is used, sample wells can be positioned in the center of the gel, so that the cleaved and uncleaved probes can be observed to migrate in opposite directions. Alternatively, a traditional vertical gel can be used, but with the electrodes reversed relative to usual DNA gels (i.e., the positive electrode at the top and the negative electrode at the bottom) so that the cleaved molecules enter the gel, while the uncleaved disperse into the upper reservoir of electrophoresis buffer.

An important benefit of this type of readout is the absolute nature of the partition of products from substrates (i.e., the separation is virtually 100%). This means that an abundance of uncleaved probe can be supplied to drive the hybridization step of the probe-based assay, yet the unconsumed (i.e., unreacted) probe can, in essence, be subtracted from the result to reduce background by virtue of the fact that the unreacted probe will not migrate to the same pole as the specific reaction product.

Through the use of multiple positively charged adducts, synthetic molecules can be constructed with sufficient modification that the normally negatively charged strand is made nearly neutral. When so constructed, the presence or absence of a single phosphate group can mean the difference between a net negative or a net positive charge. This observation has particular utility when one objective is to discriminate between enzymatically generated fragments of DNA, which lack a 3' phosphate, and the products of thermal degradation, which generally retain a 3' phosphate (and thus two additional negative charges).

The present invention contemplates embodiments wherein the specific reaction product produced by any cleavage of any oligonucleotide can be designed to carry a net positive charge while the unreacted probe is charge neutral or carries a net negative charge. The present invention also contemplates embodiments where the released product may be designed to carry a net negative charge while the input nucleic acid carries a net positive charge. Depending on the length of the released product to be detected, positively charged dyes may be incorporated at the one end of the probe and modified bases may be placed along the oligonucleotide such that upon cleavage, the released fragment containing the positively charged dye carries a net positive charge. Amino-modified bases may be used to balance the charge of the released fragment in cases where the presence of the positively charged adduct (e.g., dye) alone is not sufficient to impart a net positive charge on the released fragment. In addition, the phosphate backbone may be replaced with a phosphonate backbone at a level sufficient to impart a net positive charge (this is particularly useful when the sequence of the oligonucleotide is not amenable to the use of amino-substituted bases. An oligonucleotide containing a fully phosphonate-substituted backbone would be charge neutral (absent the presence of modified charged residues bearing a charge or the presence of a charged adduct) due to the absence of the negatively charged phosphate groups. Phosphonate-containing nucleotides (e.g., methylphosphonate-containing nucleotides) are readily available and can be incorporated at any position of an oligonucleotide during synthesis using techniques that are well known in the art.

In essence, the invention contemplates the use of charge-based separation to permit the separation of specific reaction products from the input oligonucleotides in nucleic acid-based detection assays. The foundation of this novel separation technique is the design and use of oligonucleotide probes (typically termed "primers" in the case of PCR) which are "charge balanced" so that upon either cleavage or elongation of the probe it becomes "charge unbalanced," and the specific reaction products may be separated from the input reactants on the basis of the net charge.

In the context of assays that involve the elongation of an oligonucleotide probe (i.e., a primer), such as is the case in PCR, the input primers are designed to carry a net positive charge. Elongation of the short oligonucleotide primer during polymerization will generate PCR products that now carry a net negative charge. The specific reaction products may then easily be separated and concentrated away from the input primers using the charge-based separation technique described herein.

II. Other Solid Phase Reactions

The above example of invasive cleavage reactions on solid surfaces illustrates the functionality of enzyme/nucleic acid reactions on solid surfaces. In some embodiments of the present invention, one or more other nucleic acid/enzyme reactions are carried out independently of or in conjunction with invasive cleavage reactions. Where reactions are carried out in conjunction with invasive cleavage reactions, the additional reactions may be carried out on the same solid surface as the invasive cleavage reaction or on a different solid surface (e.g., on the same or on different beads), or in solution phase or any other format that can be linked to the invasive cleavage reactions, directly or indirectly. In some embodiments, multiple assays are carried out simultaneously. In other embodiments, multiples assays are carried out consecutively. In some embodiments, one or more reaction components (e.g., nucleic acids, enzymes, etc.) may be shared between two or more different assays (e.g., one or more primers or probes). Examples of other nucleic acid/enzyme reactions include, but are not limited to the reactions described below.

A. Polymerase Chain Reaction

The "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying a target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

In some embodiments of the present invention, one or more components of a PCR reaction are attached to a solid surface, including, but not limited to, the target nucleic acid, one or more amplification primers, polymerases, oligonucleotides used to promote or maintain the target in a single stranded form, and the like (See e.g., Rasmussen et al., Anal Biochem., 198:138 [1991] and Rasmussen et al., Clin. Chem., 40:200 [1994]).

B. TAQMAN Assay

The TAQMAN assay (Applied Biosystems, Foster City, Calif.; See e.g., U.S. Pat. Nos. 5,210,015 and 5,538,848, each of which is herein incorporated by reference) utilizes the 5'-nuclease activity of polymerase enzymes during PCR reactions. For example, during PCR, a fluorogenic probe, consisting of an oligonucleotide with both a reporter and a quencher dye attached, anneals specifically between the forward and reverse primers. When the probe is cleaved by the 5' nuclease activity of the DNA polymerase, the reporter dye is separated from the quencher dye and a sequence-specific signal is generated. With each cycle, additional reporter dye molecules are cleaved from their respective probes, and the fluorescence intensity is monitored during the PCR.

In some embodiments of the present invention, one or more components of the TAQMAN assay are attached to a solid surface including, but not limited to, TAQMAN probes, polymerases, or components of the PCR reaction.

C. SNP-IT Primer Extension Assay

In still further embodiments, the present invention may employ the SNP-IT primer extension assay (Orchid Biosciences, Princeton, N.J.; See e.g., U.S. Pat. Nos. 5,952,174 and 5,919,626, each of which is herein incorporated by reference), wherein at least one of the components of this assay is attached to a solid surface. In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labeled antibody specific for biotin).

D. Additional Assays

A number of additional assays that involved the enzymatic modification of nucleic acids find use in the present invention including, but not limited to, the assays described in U.S. Pat. Nos. 4,775,619 and 5,118,605 to Urdea (the disclosures of which are herein incorporated by reference), the catalytic hybridization amplification assay described in U.S. Pat. No. 5,403,711 to Walder and Walder (the disclosure of which is herein incorporated by reference), the cycling probe assay described in U.S. Pat. Nos. 4,876,187 and 5,011,769 to Duck et al. (the disclosures of which are herein incorporated by reference), and the ligase chain reaction (LCR) described in U.S. Pat. Nos. 5,427,930 and 5,494,810 to Birkenmeyer et al. and Barany et al. (the disclosures of which are herein incorporated by reference.

III. Kits

In some embodiments, the present invention provides kits comprising one or more of the components necessary for practicing the present invention. For example, the present invention provides kits for storing or delivering the enzymes of the present invention and/or the reaction components necessary to practice a detection assay (e.g., the INVADER assay). The kit may include any and all components necessary or desired for the enzymes or assays including, but not limited to, the reagents themselves, buffers, control reagents (e.g., tissue samples, positive and negative control target oligonucleotides, etc.), solid supports, labels, written and/or pictorial instructions and product information, inhibitors, labeling and/or detection reagents, attachment reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered. For example, a first container (e.g., box) may contain an enzyme (e.g., structure specific cleavage enzyme in a suitable storage buffer and container), while a second box may contain oligonucleotides (e.g., INVADER oligonucleotides, probe oligonucleotides, control target oligonucleotides, etc.).

Additionally, in some embodiments, the present invention provides methods of delivering kits or reagents to customers for use in the methods of the present invention. The methods of the present invention are not limited to a particular group of customers. Indeed, the methods of the present invention find use in the providing of kits or reagents to customers in many sectors of the biological and medical community, including, but not limited to customers in academic research labs, customers in the biotechnology and medical industries, and customers in governmental labs. The methods of the present invention provide for all aspects of providing the kits or reagents to the customers, including, but not limited to, marketing, sales, delivery, and technical support.

In some embodiments of the present invention, quality control (QC) and/or quality assurance (QA) experiments are conducted prior to delivery of the kits or reagents to customers. Such QC and QA techniques typically involve testing the reagents in experiments similar to the intended commercial uses (e.g., using assays similar to those described herein). Testing may include experiments to determine shelf life of products and their ability to withstand a wide range of solution and/or reaction conditions (e.g., temperature, pH, light, etc.).

In some embodiments of the present invention, the compositions and/or methods of the present invention are disclosed and/or demonstrated to customers prior to sale (e.g., through printed or web-based advertising, demonstrations, etc.) indicating the use or functionality of the present invention or components of the present invention. However, in some embodiments, customers are not informed of the presence or use of one or more components in the product being sold. In such embodiments, sales are developed, for example, through the improved and/or desired function of the product (e.g., kit) rather than through knowledge of why or how it works (i.e., the user need not know the components of kits or reaction mixtures). Thus, the present invention contemplates making kits, reagents, or assays available to users, whether or not the user has knowledge of the components or workings of the system.

Accordingly, in some embodiments, sales and marketing efforts present information about the novel and/or improved properties of the methods and compositions of the present invention. In other embodiments, such mechanistic information is withheld from marketing materials. In some embodiments, customers are surveyed to obtain information about the type of assay components or delivery systems that most suits their needs. Such information is useful in the design of the components of the kit and the design of marketing efforts.

EXAMPLES

The following examples serve to illustrate certain preferred embodiments and aspects of the present invention and are not to be construed as limiting the scope thereof.

In the disclosure which follows, the following abbreviations apply: ° C. (degrees Centigrade); g (gravitational field); hr (hour); min (minute); oligo (oligonucleotide); rxn (reaction); vol (volume); w/v (weight to volume); v/v (volume to volume); DNA (deoxyribonucleic acid); μl (microliters); ml (milliliters); μg (micrograms); mg (milligrams); M (molar); mM (milliMolar); μM (microMolar); pmoles (picomoles); amoles (attomoles); zmoles (zeptomoles); and nm (nanometers).

The following examples provide illustrative examples of certain preferred embodiments of the present invention. For example, the results of these experimental examples demonstrate that multi-component substrates for the invasive cleavage assay properly assemble on a solid surface and are accurately recognized by structure-specific nucleases. As in solution-phase assays, a single target molecule associates sequentially with multiple probe molecules and facilitates cleavage of these probes, thus yielding linear amplification of the signal. Several different configurations were shown to be successful. The examples use the following materials and methods:

Materials:

Spherotech (Libertyville, Ill.) donated streptavidin-coated latex microparticles of density 1.05 g/cm$^3$. Chill-out 14 liquid wax was purchased from MJ Research, Inc. (Cambridge, Mass.), and D-biotin from Pierce Chemical Co. (Rockford, Ill.). Phosphoramidite reagents for oligonucleotide synthesis were obtained from Glen Research (Sterling, Va.). Other chemicals and buffers were from Sigma Chemical (St. Louis, Mo.). The CLEAVASE enzyme was prepared and quantified by Third Wave Technologies, Inc. (Madison, Wis.) as described (Lyamichev et al., Nature Biotechnol., 17:292 [1999]). Enzyme storage, enzyme dilution buffer, and oligonucleotide synthesis are as previously described (Hall et al., Proc. Natl. Acad. Sci. USA 97:8272 [2000]). Sequences of the oligonucleotides are listed in Table 1.

TABLE 1

A. Model System Oligonucleotides:

Upstream: 5'-atagagccataaactcaaagtggtaataat-3'
(SEQ ID NO:1)

Probe: 5'-F1 gagtCy3cctgtgatBc-3'
(SEQ ID NO:2)

Target: 5'-tgacaaaatcacaggtact
Cttattaccactttgagtttatggctctat-3'
(SEQ ID NO:3)

B. ApoE Oligonucleotides:

Upstream:

No-spacer 5'-ccccggcctggtacactgccaggct-3'
(SEQ ID NO:4)

Long-spacer 5'-B Sp Sp Sp Sp Sp Sp Sp Sp Sp Sp
ccccggcctggtacactgccaggct-3'
(SEQ ID NO:5)

Probe:

No-spacer 5'-D actt(F1-dT)tgcaggtcatcggB-3'
(SEQ ID NO:6)

Long-spacer 5'-D actt(F1-dT)tgcaggtcatcgg Sp Sp Sp
Sp Sp Sp Sp Sp Sp-3'
(SEQ ID NO:7)

Target

Cys 5'-cgcgatgccgatgacctgcagaag
Tgcctggcagtgtaccaggccgggccgcga-3'
(SEQ ID NO:8)

TABLE 1-continued

| Arg | 5'-cgcgatgccgatgacctgcagaag Cgcctggcagtgtaccaggccggggcccgcga-3' (SEQ ID NO:9) |

(Solid underlining on each target sequence indicates the region complementary to the upstream oligonucleotide; dashed underlining marks sequence complementary to the probe. The double-underlined, capitalized base is the site of the SNP. D = dabcyl; Cy3 = indocarbocyanine-3; Fl-dT = flouresceindeoxythymidylic acid; B = biotin; Sp = hexaethylene glycol spacer).

Unless otherwise stated, invasive cleavage assays were conducted in 10 mM 4-morpholinepropanesulfonic acid (MOPS), pH 7.5; 7.5 mM $MgCl_2$; 0.1% Tween 20; 10 µg/ml yeast tRNA; 5% enzyme dilution buffer; 10 ng/µl CLEAVASE enzyme, for particle-based assays, 20 µg oligonucleotide-coated particles. To prevent evaporation, 50 µl CHILL-OUT 14 liquid wax was layered on top of each reaction.

Data Collection:

Real-time FRET measurements of invasive cleavage assays were acquired with a previously described fluorometer constructed on an optical breadboard (Wilkins et al., Nucleic Acids Res., 27:1719 [1999]; Henry et al., Anal. Biochem., 276:204 [1999]). The sample was heated in the temperature-controlled tube holder for approximately 10 minutes, and the reaction was initiated by manual addition of 10 µl enzyme. For each sample, one hundred 10-ms measurements of fluorescence intensity were made at 15-s intervals over a period of at least 30 min. To minimize potential photobleaching, an electronic shutter blocked the excitation beam from the sample except during each read.

Model System:

Streptavidin-coated particles (0.86 µm diameter) were coated at 20% surface saturation with model-system probe, upstream oligonucleotide, or a 50-50 mixture of both. The coating procedure was essentially as described (Henry et al., Anal. Biochem., 276:204 [1999]), but since both the probe and upstream oligonucleotides were biotiynilated, an additional biotin-blocking step was included. After the 48-h coating period, particles were washed once and then resuspended in coating buffer containing 1 µM D-biotin and rotated for 10 min. Subsequent washes were as described, but the final particle resuspension was in 10 mM MOPS, 0.5% Tween 20, 0.5% Nonidet P-40.

In the same manner, streptavidin-coated particles were coated with the model system oligonucleotide at 40%, 80%, and 100% surface saturation. The particles for all model system studies were the same lot as those described in Henry et al. (Anal. Biochem., 276:204 [1999]), so the particle capacity at 100% surface saturation was known to be 11 pmol oligonucleotide/$cm^2$.

Invasive cleavage assays were conducted in 200 µl volume reactions at 45° C., the approximate $T_m$ of the model-system probe. Reactions were initiated by manual addition of enzyme in a 10 µl volume. The final concentration of enzyme dilution buffer for the model-system assays was 1%.

ApoE System:

Streptavidin-coated particles (0.83 µm diameter) were coated with ApoE probe or with a mixture of both probe and upstream oligonucleotide, essentially as described above for the model system, except that the biotin-blocking solution contained 10 µM D-biotin. For each batch of particles prepared, a small batch of control particles was prepared under identical conditions but with probe oligonucleotide that did not contain the 5'-terminal dabcyl quencher. During the particle coating procedures, the amount of fluorescent oligomer in control particle solutions was quantified and thereby indicating the oligonucleotide surface capacity of these particles to be approximately 4 pmol/$cm^2$.

Invasive cleavage reactions were conducted in 200 µl volumes at either 60° C. or 54° C., as stated. Reactions were initiated by manually adding enzyme to the preheated tube, inverting the tube to mix, layering 50 µl CHILL-OUT on top, and returning the tube to the heating block.

Example 1

Model System Invasive Reaction Functions in Three Solid-phase Configurations

For a functional solid phase invasive cleavage reaction, a three-component substrate consisting of target annealed to upstream oligonucleotide and probe is assembled on the surface. Additionally, an enzyme recognizes this substrate and forms a productive enzyme-substrate complex.

An indication that this complicated series of associations occurs on a solid phase came when the invasive cleavage reaction was tested in a format where the model-system target strand and probe were present in solution while the model-system upstream oligonucleotide was bound to microparticles. In this format, reaction kinetics for particle-based cleavage were virtually identical to those of a solution-phase reaction containing the same amounts of each oligonucleotide. In control reactions, where target oligonucleotide was omitted from the reaction mixture, no probe cleavage occurred. Data for these experiments is shown in FIG. 1A. The data in this figure was generated from particles that were coated with model-system oligonucleotides at 20% surface saturation. Solution phase reactions (shown in dark gray) contained the same amount of each oligonucleotide as the particle-based reactions (shown in black). Control particle-based reactions without any target oligonucleotide are shown in light gray. The graphs of FIG. 1 plot signal generation versus time; RFU=relative fluorescence units. In FIG. 1A, reactions included 15 nM upstream oligonucleotide in solution or particles coated with upstream oligonucleotide, 500 nM probe in solution, and 1 nM target, if present.

In a second assay format, the model-system probe oligonucleotide was the particle-bound reagent. In a third format, equimolar amounts of both model-system oligonucleotides were attached to the particles. The particle-based invasive cleavage reaction was also functional in these assay formats, but cleavage on the solid phase occurred considerably slower than in solution-phase reactions with equivalent amounts of each oligonucleotide. Again in these formats, signal generation occurred only in reactions containing target oligonucleotide but not in control reactions with no target. Higher concentrations of solid-phase probe oligonucleotide increase reaction rates. Data for the second and third formats are shown in FIGS. 1B and 1C, respectively. For FIG. 1B, 15 nM of probe, 25 nM upstream oligonucleotide, and 100 pM of target, if present, was used. For FIG. 1C, 7.5 nM of each oligonucleotide and 100 pM target, if present, was used.

Example 2

Figure 2:
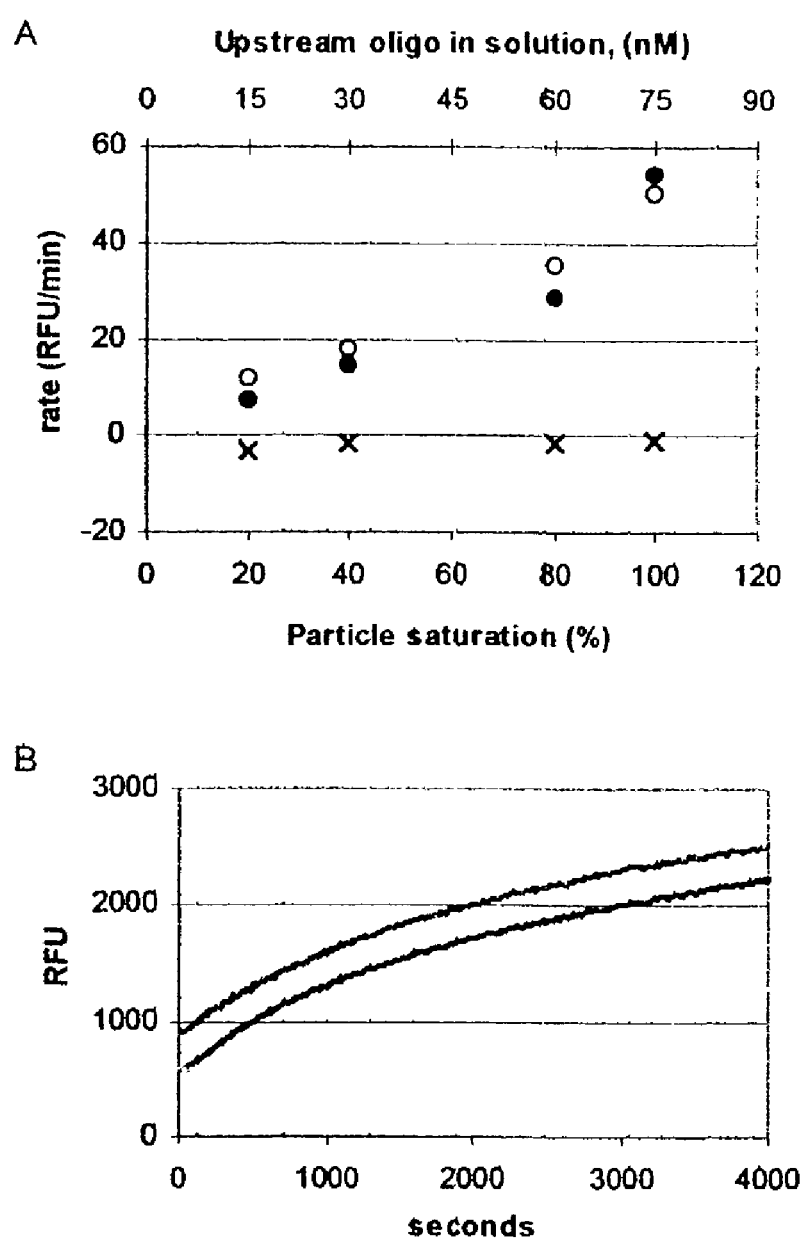
FIGS. 2A-B show graphs plotting data of model-system reactions with various concentrations of solution-phase and solid-phase probe.

Higher Concentrations of Solid-phase Probe Oligonucleotide Increase Reaction Rates Particles coated with model-system probe at surface densities of 20%, 40%, 80%, and 100% of the bead's maximal oligonucleotide capacity were tested in invasive cleavage reactions. The initial rates of these particle-based reactions increased with surface density of the probe oligonucleotide and were very similar to initial rates of solution-phase reactions containing equivalent amounts of each oligonucleotide. Data for these experiments is shown in FIG. 2A. Reactions were conducted with 50 nM upstream oligonucleotide and 100 pM target (filled circles) or no target (shown with an X). Each solution-phase reaction (open circles) contained 50 nM upstream oligonucleotide, 100 pM target, and an amount of probe equivalent to that in the corresponding particle-based reaction. The lower horizontal axis is for particle-based data; the upper axis is for the solution phase data. Initial reaction rates were calculated from the slopes of data from 30-480 seconds.

For reactions with particles saturated with probe oligonucleotide, the shape of the response curve was the same as for solution-phase reactions with 75 pM probe as shown in FIG. 2B, showing invasive cleavage assay signal versus time for solution-phase assay with 100 pM target (dark gray), particle-based assay with 100 pM target (black), or particle-based assay with no target (light gray). The surface of the particles was saturated with probe oligonucleotide. For reactions with particles coated with probe at less than 100% surface density, however, after about 5 to 10 minutes, the rate on the particles decreased relative to the solution-phase rate. The results in FIG. 1B, where particles are 20% saturated with probe oligonucleotide, illustrate this trend.

Example 3

Fluorophore and Quencher can be Reversed in Solid-phase Reaction

Experiments with the model system demonstrated that the invasive cleavage reaction successfully adapted to a solid-phase format. Productive tripartite substrate molecules were assembled on the particle surface, and enzyme cleavage resulted in signal amplification. In the model system the fluorescein molecule was released from the particle surface and detected in solution, so that assay configuration would be difficult to adapt to solid-phase applications requiring signals at addressable locations. Therefore, a second oligonucleotide system was investigated based on the ApoE 158 SNP. In the second system the positions of the fluorophore and quenching molecules on the probe were reversed. The dabcyl quencher was positioned at the 5' end of the ApoE probe, while the fluoresceinated nucleotide was at the fifth position as shown in Table 1.

TABLE 2

| Probe density | Initial slope, 0-2 min (RFU/min) | | | | Ratio of initial slopes longer spacer: no spacer | Slope, 10-30 min (RFU/min) long spacer probe | | | |
|---|---|---|---|---|---|---|---|---|---|
| | long-spacer probe | | no-spacer probe | | | 100 pM target | | 10 pM target | |
| | 1 nM target | | 1 nM target | | | | | | |
| | Cys | Arg | Cys | Arg | | Cys | Arg | Cys | Arg |
| 100% | 102 | 4.5 | 214 | 19 | 2.1 | 11 | 0.14 | 1.2 | −0.041 |
| 75% | 120 | 11 | 229 | 17 | 1.9 | 11 | 0.12 | 1.2 | 0.091 |
| 40% | 102 | 13 | 234 | 14 | 2.3 | 9.1 | −0.016 | 1.2 | −0.056 |
| 20% | 110 | 16 | 178 | 8.9 | 1.6 | 7.7 | −0.12 | 0.88 | 0.019 |

(Reactions at 60° C. with 50 mM INVADER oligonucleotide and 1 nM, 100 pM, or 10 pM ApoE 158 Cys or Arg target. For reactions with 1 nM target, initial slopes were calculated from 0-2 min data, as explained in Example 3. The ratio of initial slope is based on values for the Cys target. Reactions with 100 pM and 10 pM target were conducted on particles coated with the long-spacer probe, and slopes were calculated from 10-30 min data).

An objective was to test whether a productive tripartite substrate would assemble when a probe configured with the 5' quencher and internal fluorescein was attached to the solid phase and whether target-specific cleavage of the probe would be detected by fluorescence increase of the particle-bound fluorescein. In the ApoE system, two different types of target molecules corresponding to the two human alleles for the SNP at residue 158 were tested as shown in Table 2, above. Target molecules containing the sequence corresponding to Cys at ApoE position 158 (herein referred to as "Cys target") have a T that is complementary to the A at the 5' end of the probe. On the other hand, the "Arg target," with the sequence corresponding to Arg at position 158, is not complementary to the final nucleotide of the probe. In solution-phase invasive cleavage reactions, Cys probes are efficiently cleaved when the Cys target is included in the reaction, while Cys probes are not cleaved when the Arg target is included.

Figure 3:
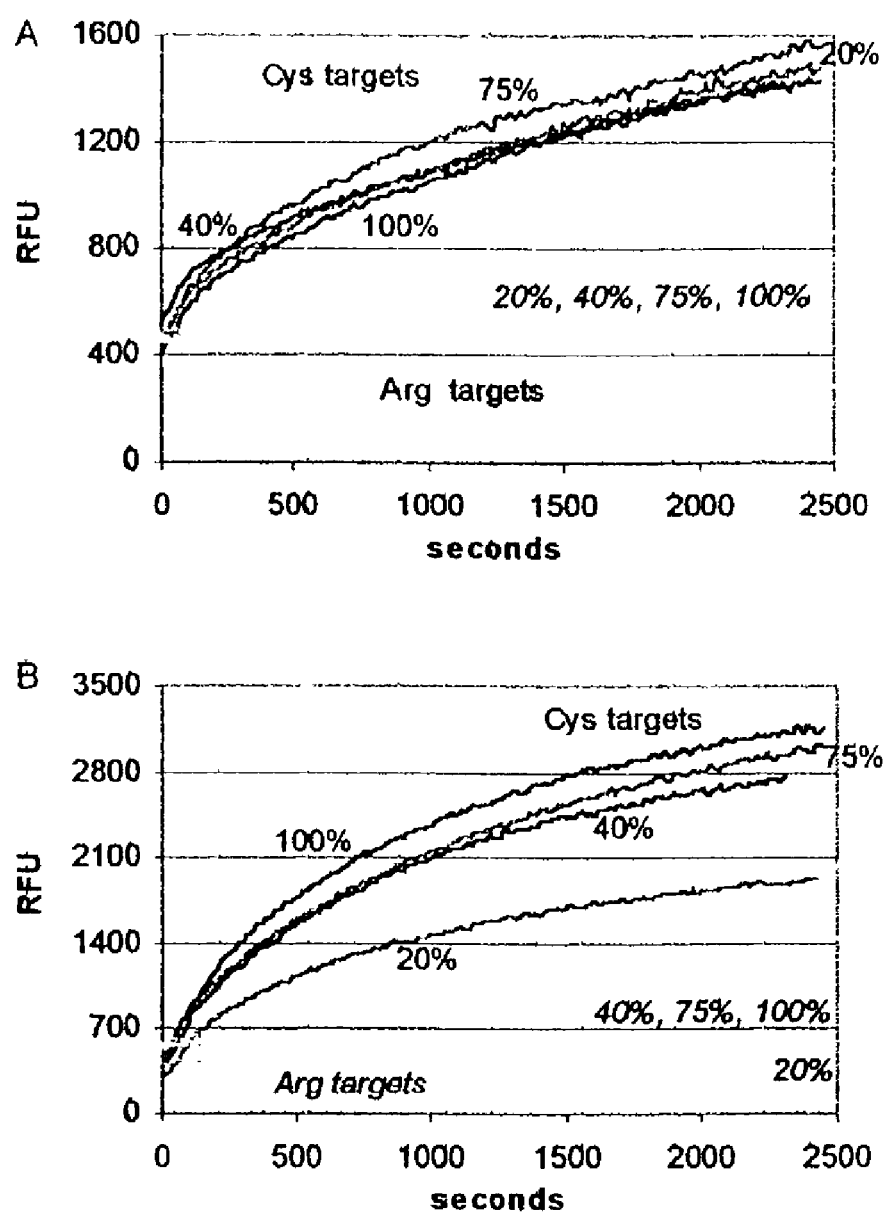
FIGS. 3A-B show graphs plotting data of solid-phase ApoE reactions with various surface densities of short-spacer or long-spacer probe.

To test whether particle-based ApoE probe could function in the invasive cleavage reaction and discriminate the single nucleotide difference between the Cys and Arg targets, particles were coated with the ApoE probe at four different surface densities, and each type of particle was tested with the Cys and Arg targets. The Cys target was cleaved well by particles coated with probe at all four surface densities, while the Arg target demonstrated virtually no cleavage, as shown in FIG. 3. FIG. 3 shows data from particles coated at various surface densities with the no-spacer (FIG. 3A) or long-spacer (FIG. 3B) ApoE probe. The particles were tested at 60° C. with 50 nM upstream oligonucleotide and 1 nM Cys target. Black lines represent Cys target data for probe surface densities of 100% and 40%; Cys target data for densities of 75% and 20% are shown in dark gray. In the lower portion of each graph, Arg target data are represented by light gray lines for all probe surface densities.

Unlike particle-based reactions with the model-system oligonucleotides, surface density of the ApoE probe had little effect on the initial reaction rates and overall signal generation kinetics. While the present invention is not limited by any mechanism and an understanding of the mechanism is not required to practice the present invention, it is contemplated that self quenching of probe fluorophores on the surface of ApoE particles at least partially accounts for this difference between the two systems.

Example 4

Probes with Long Tethers Exhibit Higher Signals and Improved Reaction Rates

ApoE probes were positioned away from the surface of the particle with a long spacer to investigate the effect on invasive cleavage reactions. An ApoE probe with a long spacer containing ten hexaethylene glycol units between the end of the probe sequence and the 3' biotin was used. In the previous experiments, the 3' biotin had been directly attached to the probe sequence without any intervening spacer (Table 1, above).

When invasive cleavage reactions were conducted with particles coated with this long-spacer probe at different surface densities, signals were dramatically higher than in reactions with particles coated with the ApoE probe containing no spacer as shown in FIGS. 3A and 3B. As was the case with the model system, where the fluorescein molecule was released into solution, increasing the surface density of the long-spacer version of the ApoE probe resulted in increased signal from the reaction. With the long-spacer ApoE probe, the solid-phase signal observed for the particles with a probe surface density of 40% of the saturating concentration was clearly greater than the signal observed for particles with 20% probe surface density. At the higher probe densities, however, the increase in solid-phase signal was less dramatic. While the present invention is not limited to any mechanism and an understanding of the mechanism is not necessary to practice the present invention, the less dramatic increase perhaps indicates that some fluorophore self-quenching occurred in this system at the increased surface densities, even with the long tethers.

For 1 nM Cys target, initial reaction rates on particles with the long-spacer ApoE probe were about 2-fold faster than on particles with the no-spacer probe, although the 20% saturated particles demonstrated somewhat less than a 2-fold rate increase as shown in Table 2. With this relatively high concentration of Cys target, the reaction rate was linear for approximately the first 3 minutes, but became nonlinear as the reaction progressed. Initial slopes for the 1 nM Cys target data in Table 2 are calculated from 0-2 min reaction data, a region where all types of particles demonstrated linear slopes with the Cys target. With 1 nM Arg target, however, there was a small increase in signal during the first minute or two of the reaction, and then the signal remained essentially flat throughout the remainder of the reaction. The initial burst in signal after enzyme addition appears to be due to temperature and buffer equilibration of the reaction solution, since fluorescence of the fluorescein reporter molecule is extremely sensitive to environmental conditions (Sjoback et al., Biopolymers 46:445 [1998]). The Arg target data did not exhibit linear signal increases in the 0-2 min range, so the initial slopes reported in Table 2 for the 1 nM Arg targets are dominated by the equilibration-related signal increase. Slopes calculated from the 1 nM Arg target data in the linear region from 10-30 min are much lower, ranging from 0.2-0.6 relative fluorescence units/minute (RFU/min) for the particles with no-spacer probe and from 0.5-0.8 RFU/min for the particles with long-spacer probe.

Figure 4:
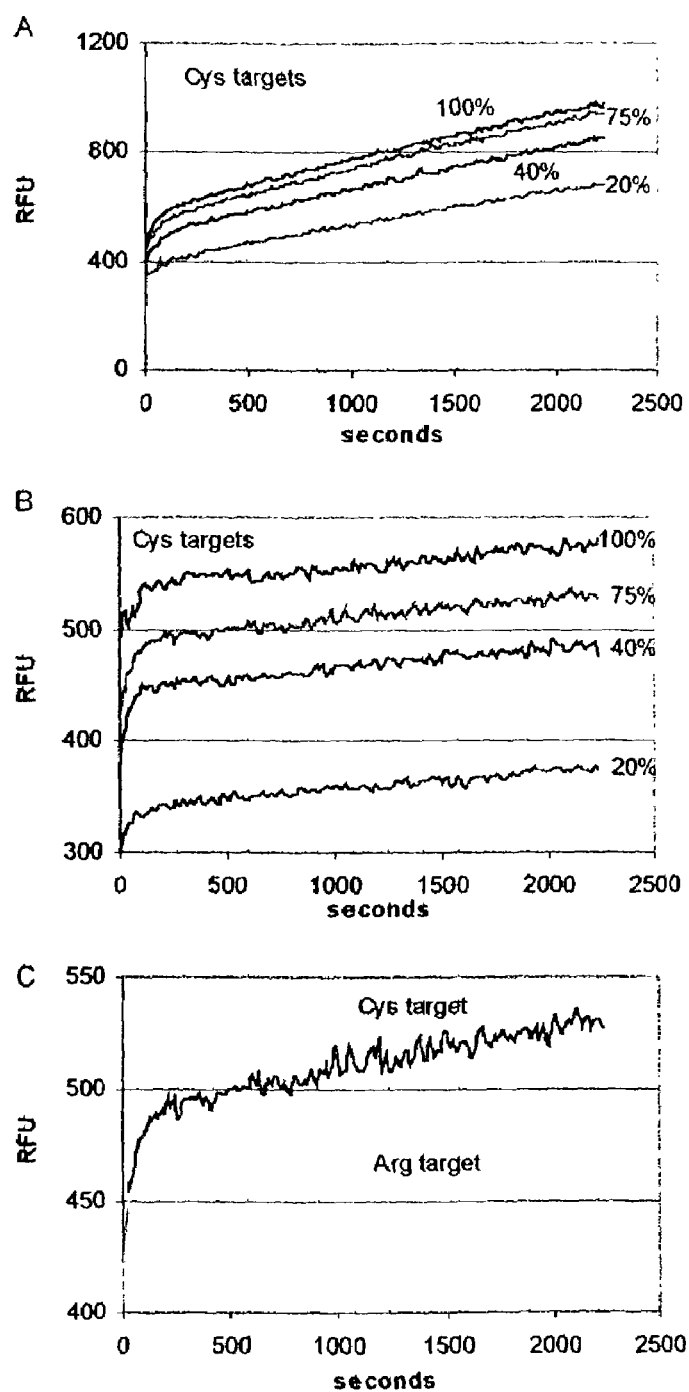
FIGS. 4A-B show graphs plotting data of solid-phase ApoE reactions with 100 pM or 10 pM target concentrations.

When 100 pM and 10 pM target concentrations were tested with the particles coated with long-spacer ApoE probe oligonucleotide, responses of both the Cys and Arg targets demonstrated an initial burst in fluorescence signal in the first minute or two of the reaction. As described above for the 1 nM Arg target data, this increase appears to be related to equilibration of the solution after enzyme addition. Past the equilibration time, linear kinetics were observed for each Cys target level and each probe surface density. With 10 pM Cys target, the cleavage rate was approximately 1 RFU/min, a cleavage rate clearly distinguishable from the rate observed with 10 pM Arg target, as shown in Table 2 and FIGS. 4A-C. In FIG. 4, particles coated at various surface densities with long ApoE probe were tested at 60° C. with 50 nM upstream oligonucleotide and 100 pM (FIG. 4A) or 10 pM (FIG. 4B) Cys target. Black lines represent Cys target data for oligonucleotide surface densities of 100% and 40%; Cys target data for densities of 75% and 20% are shown in dark gray. In FIG. 4C, invasive cleavage reaction with particles of 75% surface density were conducted as in FIG. 4B, but with 10 pM Cys (dark gray) or Arg (light gray) target.

Because of better performance, long-spacer probes were utilized for all further investigations. Also, since the data did not point to any advantage for an oligonucleotide coating level of less than 100%, only surface-saturated particles were used in subsequent experiments. To determine the optimal reaction temperature for the ApoE system's solid phase invasive cleavage reaction, cleavage rates of the particle-bound ApoE probe with 10 pM Cys target were measured. Of temperatures tested in the range from 50° C. to 60° C., the optimal temperature was 54° C. Thus for further ApoE studies, 54° C. became the standard reaction temperature. This temperature is similar to the 54.5° C. optimum determined for the ApoE 158 invasive cleavage reaction on a planar surface. For the solution-phase reaction, the maximal reaction rate was observed at 60° C.

Example 5

Reactions with Both Upstream Oligonucleotide and Probe Attached to Surface

For parallel analysis of multiple SNPs, the solid-phase invasive cleavage reaction would be simplified if both upstream oligonucleotide and probe were confined on the surface. The results described above for the model system (FIG. 1C) support the feasibility of this approach. To further investigate this format, upstream oligonucleotide was synthesized for the ApoE invasive cleavage reaction with a 5' biotin separated from the oligonucleotide sequence by ten hexaethylene glycol spacers (Table 1). Particles were coated with mixtures of the probe and upstream oligonucleotide and tested in invasive cleavage assays with the Cys and Arg targets.

Figure 5:
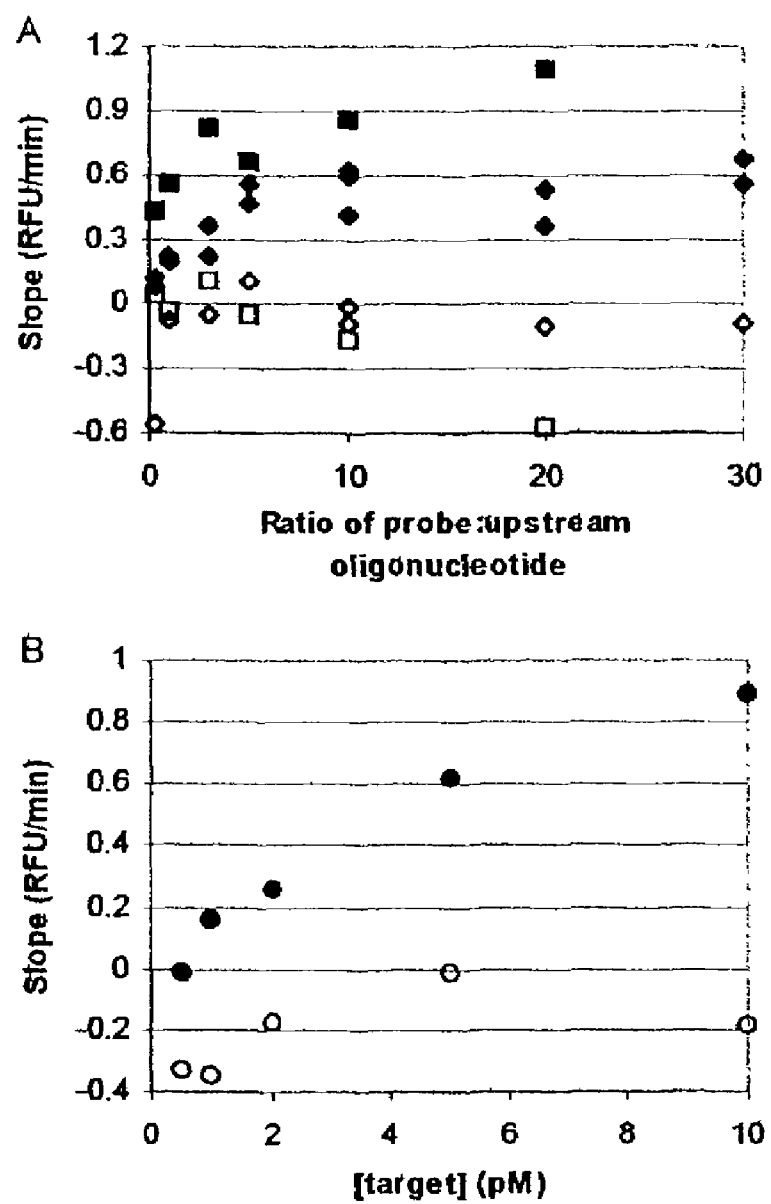
FIGS. 5A-B show graphs plotting data of solid-phase ApoE reactions on particles coated with mixtures of long-spacer probe and upstream oligonucleotide.

FIG. 5A summarizes results from particle-based invasive cleavage reactions conducted with 5 or 10 pM Cys or Arg target. Reactions were run at 54° C., with slopes calculated form 10-30 minute data. Particles coated with various ratios of ApoE probe and upstream oligonucleotide were tested with the following targets: 5 pM Cys (filled diamond); 5 pM Arg (open diamond); 10 pM Cys (filled square); and 10 pM Arg (open square). The particles had Cys probe:upstream oligonucleotide ratios of 1:3, 1:1, 3:1, 5:1, 10:1, 20:1, and 30:1. At all ratios tested, the particle-based assay was able to discriminate between the specific Cys target and the non-specific Arg target. In general, particles with higher ratios of probe:upstream oligonucleotide demonstrated greater separation of values for the positive and negative targets.

Example 6

Titration of Target for Solid-phase Invasive Cleavage Reactions

To test discrimination between Cys and Arg ApoE targets at different target levels, the particles coated with probe and upstream oligonucleotide at a ratio of 10:1 were used. FIG. 5B shows that the solid-phase reaction with these particles demonstrated clear differences in the initial cleavage rates for the Cys and Arg targets down to 0.5 pM (100 amol/assay). Although the slope for the reaction with 0.5 pM Cys target was essentially zero, it was significantly different from the slope for the reaction with Arg target at the same concentration.

For each of the Examples above, one skilled in the art will appreciate that comparisons may be carried out using end-point data rather than, or in conjunction with, kinetic data.

Example 7

Genotyping SNPs Directly from Genomic DNA by Invasive Cleavage on Microspheres

This Example describes the results of a microsphere-based genotyping assay that detects single nucleotide polymorphisms (SNPs) directly from human genomic DNA samples (e.g., without prior amplification by PCR or other amplification techniques). Genomic DNA samples were genotyped for the SNP in the Apolipoprotein E gene at amino acid position 158. The assay successfully scored wild type, heterozygous and homozygous mutants. This example provides a simple assay that has multiplexing capabilities, making it adaptable for high-throughput genotyping applications.

A number of solution-phase SNP-genotyping methodologies have been combined with a microsphere-capture step in what has become known as "suspension array technology" (Nolan and Sklar, Trends Biotechnol 20: 9 [2002]). Mini sequencing, single base chain extension (SBCE), allele-specific primer extension (ASPE), and the oligonucleotide ligation assay (OLA) have all been incorporated into microsphere-based flow-cytometry SNP-detection assays. For each of these methodologies, the starting material is PCR-amplified genomic DNA. In mini sequencing, SBCE and ASPE, address-tagged oligonucleotides are hybridized to PCR-amplified genomic DNA targets and then extended by DNA polymerase. In OLA, address-tagged capture oligonucleotides and reporter probes are hybridized to PCR-amplified genomic DNA target and then ligated. In all cases, the reaction products are hybridized to microsphere-immobilized oligonucleotides complementary to the address tags, and the fluorescently-coded microspheres are analyzed by flow cytometry.

Figure 7:
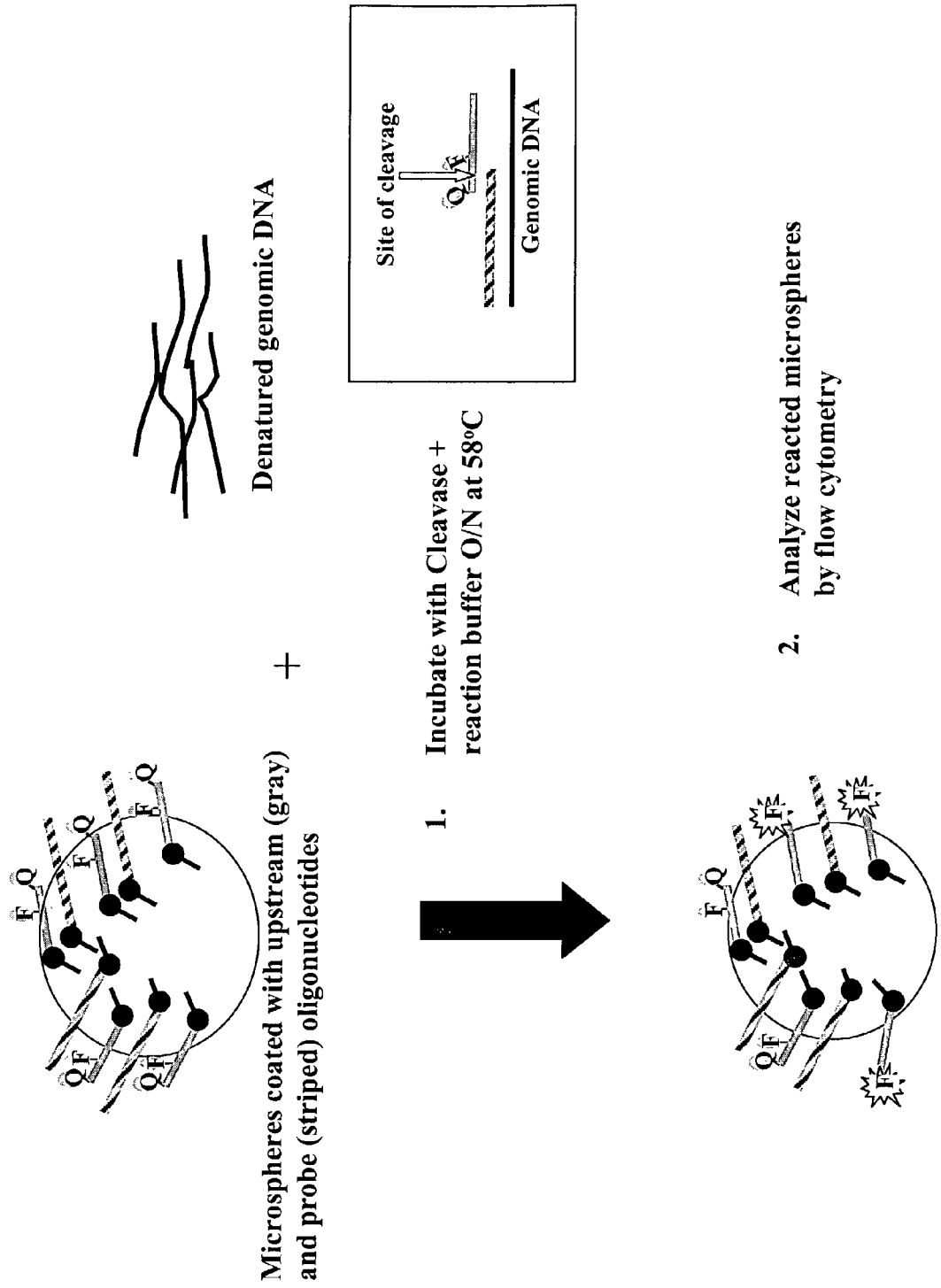
FIG. 7 shows a schematic diagram of invasive cleavage reaction on microspheres in some embodiments of the present invention. Gray lines represent probe oligonucleotides, which are labeled with fluorescein (F) and a dabcyl quencher moiety (Q). Striped lines represent upstream oligonucleotides. Both types of oligonucleotides are tethered to the microsphere surface by a long linker, represented in the figure by a black lollipop shape. Genomic DNA hybridizes to the probe and upstream oligonucleotides to form a tripartite substrate, as shown in the inset box. When the probe is complementary to the genomic DNA at the position of the SNP, the enzyme cleaves the probe, releasing the quencher. In the figure, fluorescence of fluorescein molecules on cleaved probes is represented by an F highlighted by a starburst.

Invasive cleavage reactions offer a simple and specific method for genotyping SNPs without prior PCR amplification of the genomic DNA target. In the current example, it is demonstrated that flow cytometry analysis of a microsphere-based invasive cleavage assay can be applied to genotype SNPs from human genomic DNA without any prior amplification. This assay format is extremely simple, with a single isothermal incubation step followed by flow cytometry analysis as shown in FIG. 7. The high precision of flow cytometry analysis, the ease of preparing a suspension array, the possibility for reading large numbers of replicates, and the potential for multiplexing are all factors that make the microsphere-based invasive cleavage reaction an attractive new SNP-genotyping methodology.

As a model system for these studies, the SNP in the apolipoprotein E (ApoE) gene at amino acid position 158 was chosen. Genomic DNA samples isolated from 32 individuals were analyzed with the microsphere-based invasive cleavage assay to determine the ApoE 158 genotype. Previously genotyped at Third Wave Technologies with the commercially available solution phase Invader® assay, the 32 samples included wild-type, heterozygous, and homozygous mutant genetic variants of ApoE 158.

All genomic DNA samples were tested with both Arg and Cys microspheres, in which probe cleavage occurs with ApoE 158 DNA containing, respectively, the cgc triplet coding for arginine or the tgc triplet encoding cysteine. For each genomic DNA sample, assay data is recorded as ordered pairs representing signals from reactions with Arg microspheres and Cys microspheres, respectively, with both reactions being from the same thermocycler run.

Figure 8:
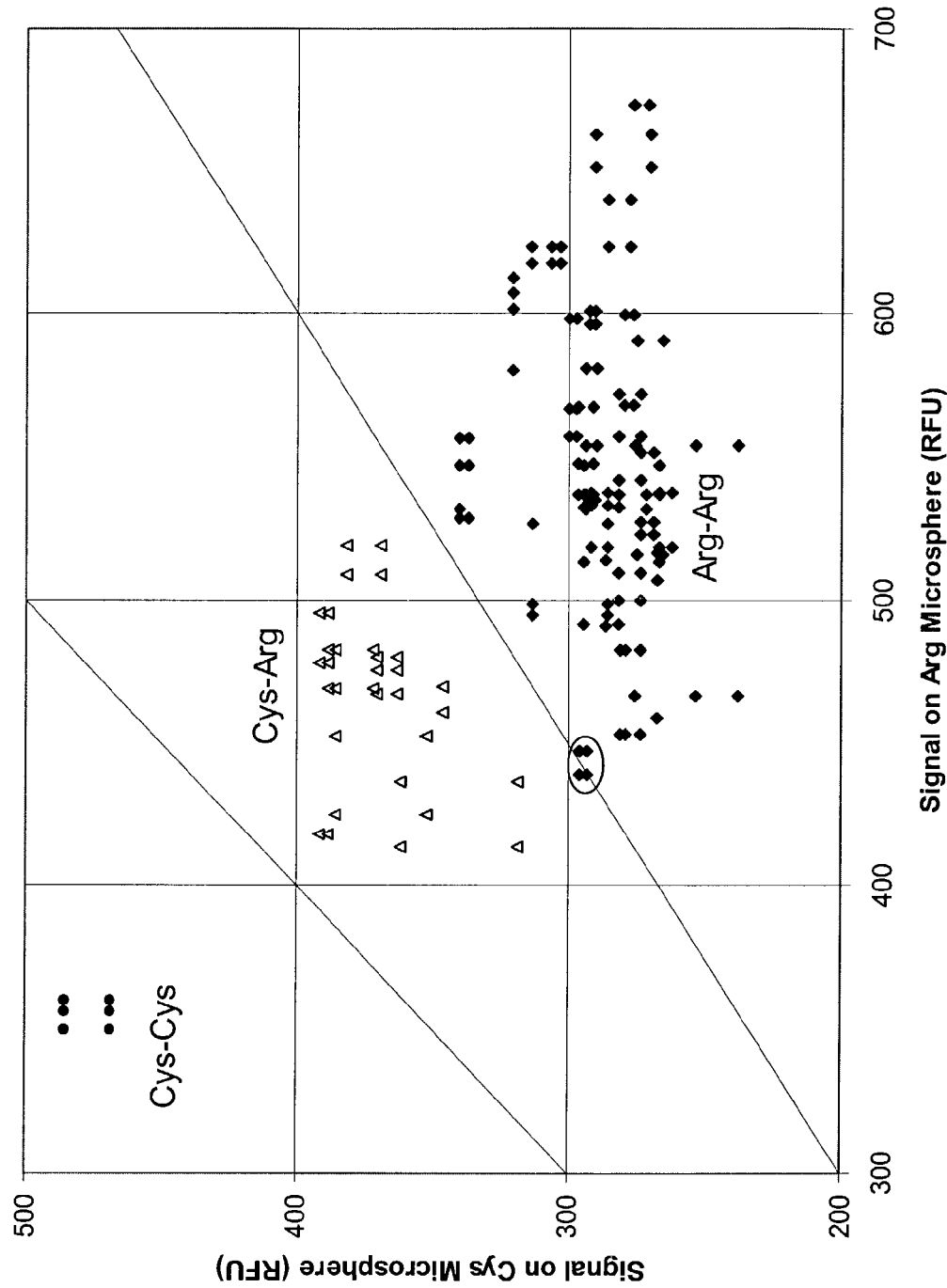
FIG. 8 shows a graph of data obtained from human subjects using methods of the present invention.
Figure 9:
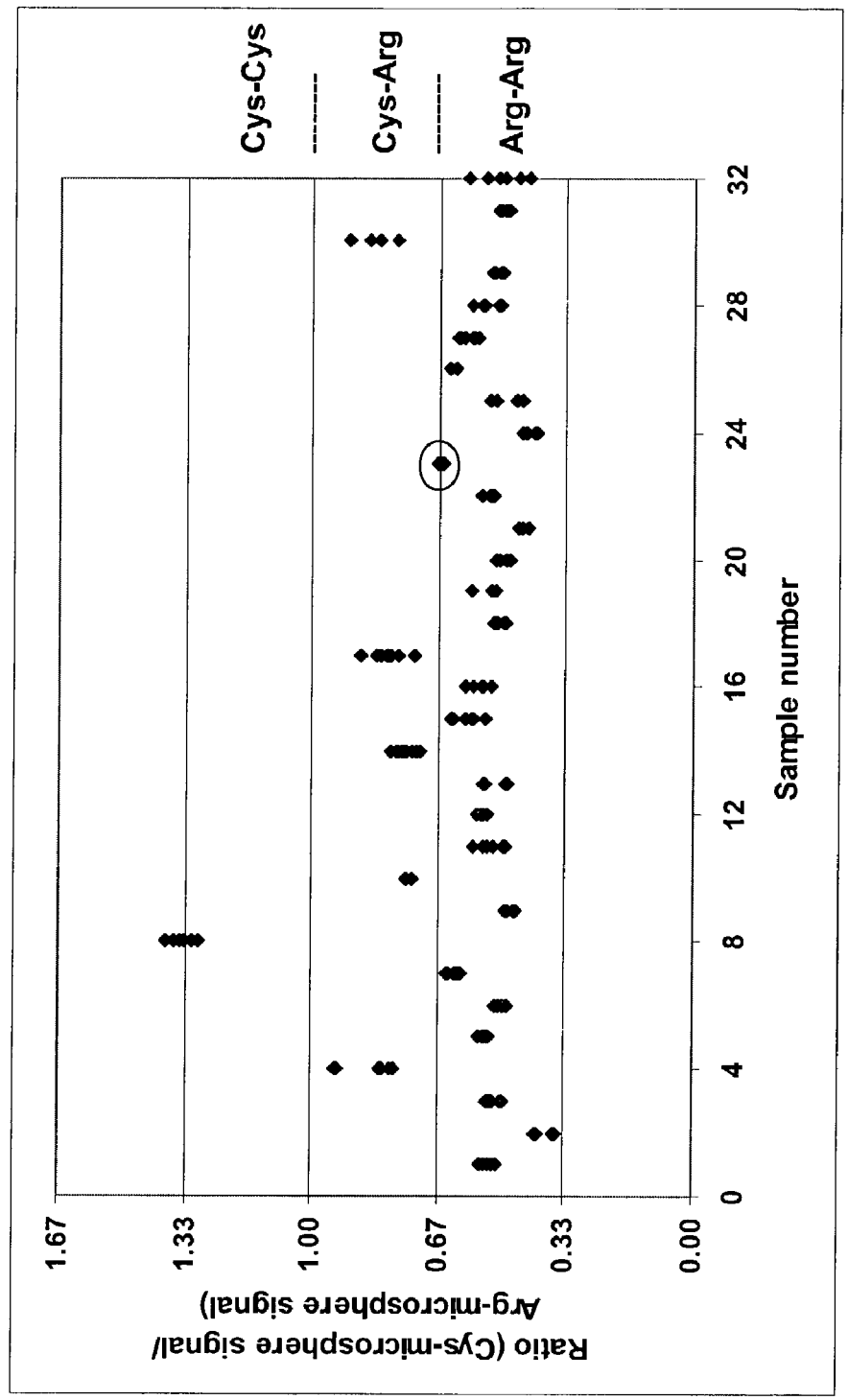
FIG. 9 shows a graph of data obtained from human subjects using methods of the present invention.

FIG. 8 plots ordered pairs for all ApoE 158 tests of the 32 genomic DNA samples with the microsphere-based invasive cleavage assay. In FIG. 8, the relative fluorescence signal obtained from reaction with Arg microspheres is plotted along the x-axis, and a corresponding relative fluorescence signal obtained from reaction with Cys microspheres is plotted along the y-axis. Lines through the origin with slopes of 1 (upper line) and 0.67 (lower line) divide the plotted data into 3 groupings representing Cys-Cys homozygotes (upper left-hand corner), Cys-Arg heterozygotes (central region), and Arg-Arg homozygotes (lower right-hand corner). In FIG. 9, data from the same ordered pairs are plotted by sample number as ratios, where the Cys-microsphere signal is the ratio's numerator and the Arg-microsphere signal is the denominator. Samples with ratios greater than 1.0 are designated as Cys-Cys homozygotes; samples with ratios between 1.0 and 0.67 are Cys-Arg heterozygotes; and samples with ratios of 0.67 or less are Arg-Arg heterozygotes.

Of the 32 genomic DNA samples tested for ApoE 158 genotype, 1 sample was from a Cys-Cys homozygote; 5 samples were from Cys-Arg heterozygotes; and 26 were from Arg-Arg homozygotes. Circled data represent ordered pairs from tests of genomic DNA sample 23. Although categorized as having an ApoE 158 genotype homozygous for the Arg codon, this DNA sample yielded signals extremely close to those expected for heterozygous samples. These 4 ordered pairs (2% of the 187 pairs tested) were therefore too close to call with confidence.

Genotyping SNPs from human genomic DNA with the microsphere-based invasive cleavage reaction has several advantages over other methods. 1) The assay does not require PCR amplification (or other forms of amplification) of the genomic DNA. 2) The two-step assay presented in this study is very simple and could easily be adapted to an automated format. 3) No wash steps are required prior to analysis on the flow cytometer. 4) Reactions are isothermal, simplifying oligonucleotide design for multiplex applications. 5) This technique inherits the powerful analytical capabilities of flow cytometry: robustness, precision, sensitivity, and the potential for simultaneous quantitative measurement of multiple parameters. 6) The possibility of suspension array multiplexing means the assay is compatible with high-throughput applications. 7) Each array element can be prepared in bulk to provide a long-term supply of the microsphere reagents. 8) Array elements can be stored in solution without having the problems associated with the drying of arrays.

Most SNP genotyping assays developed so far require a PCR amplification step to achieve the required specificity and sensitivity. This constraint limits throughput for genotyping applications that seek to achieve parallel probing of millions of SNPs. Multiplexing PCR by generating amplicons from multiple targets in a single tube is possible, but it has proven difficult to amplify more than 10 DNA fragments simultaneously (Syvanen, Nat Rev Genet 2:930 [2001]).

The number of steps and the technical expertise required for performing each step in an assay are important factors for high-throughput and clinical applications. Since the number of steps in the current assay are few, it is readily adopted by any analytical clinical laboratory, and it is also amenable to automation.

The ability of flow cytometry to distinguish the free fluorescence from microsphere-bound fluorescence (Nolan and Sklar, Nat. Biotechnol. 16:638 [1998]) eliminates washing steps from the microsphere-based invasive cleavage assay. In the present example, the samples were read directly after reaction by simply suspending the 10 µl reaction into 200 µl of buffer.

Although the solution-phase invasive cleavage assay has been successfully applied to genotype directly from as little as 70 ng of genomic DNA in a 96-well plate format, a complete genotype analysis of an individual with 3 million SNPs would require handling several thousands of microplates and several milligrams of DNA. A highly multiplexed microsphere-based assay would circumvent this problem by limiting handling to a few tubes and quantities of genomic DNA on the order of a few µg. The throughput of such a multiplexed system is limited not by digital signal processing (~100,000 events $s^{-1}$) but by microsphere density. At 0.5% w/v, the 3.2-µm-diameter microspheres used in this example are equivalent to 300,000 microspheres $\mu l^{-1}$, the equivalent of at least $10^4$ assays in a 10 µl volume, wherein each assay class is represented by 300 microspheres.

For multiplex applications, microspheres can be coded by different techniques. The Luminex FlowMetrix™ system consists of 64 different bead sets manufactured with uniform, distinct proportions of red and orange fluorescent dyes (Vignali, J Immunol Methods 243:243 [2000]). Another option that offers the potential for even higher level multiplexing, up to several thousand-fold for high-throughput applications, is multi-color optical coding in which different size quantum beads are embedded in microspheres at precisely controlled ratios (Han et al., Nat. Biotechnol. 19:631 [2001]).

The experimental conditions used in the example are provided below.

Materials

Streptavidin-coated 3.18- and 2.17-µm-diameter polystyrene microspheres and 3-µm Rainbow Calibration Particles for flow cytometry were the kind gifts of Dr. Jeff Wang, Spherotech, Inc., Libertyville, Ill. Cleavase X enzyme, dilution buffer, and reaction buffer were prepared and quality controlled at Third Wave Technologies (Madison, Ill.) as described previously (Hall et al., Proc Natl Acad Sci USA 97: 8272 [2000]). D-biotin was purchased from Pierce Chemicals (Rockford, Ill.), and other reagents were purchased from Sigma (St. Louis, Mo.). Disposable borosilicate glass cuvettes of 6×50 mm for fluorometry analyses and 12×75 mm polystyrene tubes for flow cytometry analyses were from Fisher Scientific (Itasca, Ill.).

SNP for Genomic DNA Studies

For the current study, the SNP system is the SNP in the apolipoprotein E gene at amino acid position 158. Alleles contain either the cgc triplet coding for arginine or the alternative codon tgc, which codes for cysteine. The ApoE 158 upstream and probe oligonucleotides, described previously (Wilkins Stevens et al., Nucleic Acids Res 29: E77 [2001]), are biotinylated and contain linkers with 10 hexaethylene glycol spacers. Microspheres coated with Arg probe are called "Arg microspheres," and those coated with Cys probe are termed "Cys microspheres." The same upstream oligonucleotide is utilized for both types of microspheres.

For most experiments, the probe coated onto the microspheres contained a fluorescein and a Dabcyl quencher moiety. Enzyme cleavage of the probe releases the quencher. For the determinations of oligonucleotide density and fluorescence linearity described below, particle coating solutions contained cleaved probe, which we have termed "fluorescent probe." These oligonucleotides retain the fluorescein label but lack the quencher.

Coating of Microspheres with Oligonucleotides

Polystyrene microspheres were coated with a 1:1 ratio of upstream and probe oligonucleotides as described previously (Wilkins Stevens et al., 2001). Briefly, 3.18-µm-diameter polystyrene microspheres were washed with phosphate-buffered saline, 0.1% Tween 20 (PBST) 4 times, sonicated for 30 s with a probe sonicator (Fisher Scientific), and then coated with 1 µM upstream and probe oligonucleotides in PBST by incubating in a rotary shaker for 48 h at room temperature. The microspheres were centrifuged, washed with PBST, and blocked for 10 minutes with 10 µM D-biotin. The microspheres were washed again in PBST 4 times, resuspended in 10 mM MOPS, 0.5% Tween-20, 0.5% NP-40, and stored at 4° C.

Human Genomic DNA Samples

At Third Wave Technologies, human genomic DNA samples were prepared from whole blood by an automated Gentra Systems procedure and genotyped for the ApoE SNP by a solution-phase invasive cleavage assay. For the current study, all DNA samples were repurified manually with the Puregene DNA isolation kit (Gentra Systems, Minneapolis, Minn.) and dissolved in distilled water. Prior to reaction set-up, DNA samples were denatured in a boiling water bath for 20 minutes and then snap chilled on ice. The amount and purity of each DNA sample was estimated from absorbances of the denatured DNA at 260 and 280 nm (Pharmacia LKB Ultrospec III).

Selecting Concentration of Genomic DNA for Assay

To investigate the amount of genomic DNA required for performing the invasive cleavage assay on microspheres, various concentrations of genomic DNA were tested on Arg microspheres using Arg-Arg homozygous genomic DNA in the assay protocol described below. With increasing concentrations of DNA, there was a linear increase in the relative fluorescence signal. With 7.5 µg of genomic DNA concentration, the fluorescence signal was not distinguishable from that of control microspheres, but with 15 µg of genomic DNA the signal was clearly significant. With 25 µg of genomic DNA, the signal was double the background signal of control microspheres. To allow enough DNA for adequate signal from heterozygous samples, the assay was run with 25-35 µg genomic DNA per reaction.

Assay Set-up

Assays were performed overnight in a 10 µl volume in a Perkin-Elmer 2400 thermal cycler. Unless otherwise specified, each reaction contained assay buffer (10 mM MOPS, pH 7.5), 125 mM $MgCl_2$, 0.1% Tween-20, 10 µg/ml tRNA, 1 µg/ml Cleavase X enzyme, and 1,250 Cys or Arg microspheres. Finally, denatured genomic DNA was added to the tubes. Reactions with synthetic DNA targets at 250 fM were included in each thermocycler run as positive and negative controls. In addition, microspheres alone (no target DNA) with and without enzyme addition were included in each run as negative controls. After incubation overnight at 58° C., the 10 µl reaction was transferred into 200 µl 0.2 M carbonate buffer (pH 9.4) in a 12×75 mm polystyrene tube. To disrupt aggregates, microspheres were sonicated 30 min in a Sonic water bath (FS9, Fisher Scientific) and then vortexed briefly prior to flow-cytometry measurements.

Flow Cytometry Measurements of Microsphere Fluorescence

Flow-cytometry measurements were performed on a FACScan (Becton-Dickinson Immunocytometry Systems, SanJose, Calif.) equipped with a 15-mW argon-ion air-cooled laser emitting 488-nm light. Data for fluorescence, forward scatter, and side scatter were acquired through CELLQuest Version 3.3 software. Rainbow Calibration Particles (Spherotech, Inc.) were run on the flow cytometer, and the instrument's gain was adjusted so that peak 4 of these calibration particles read ~1000 fluorescence units. The threshold on the fluorescence channel was set such that negative control microspheres could just be read, thus eliminating the background fluorescence associated with any small particle contamination. At least 500 microspheres were counted for each assay.

Flow cytometry data was analyzed on Microsoft Windows with Windows Multiple Document Interface Flow Cytometry Systems (WinMDI) software, version 2.8. The software is available at the facs.scripps.edu web site. Samples containing control microspheres were utilized to set gates on forward scatter and/or side scatter to select for microsphere-sized objects. Then, for each sample's gated microspheres, median fluorescence units were determined. Relative fluorescence units (RFU) reported in the text are normalized values calculated with reference to peak 4 of the Rainbow Calibration Particles adjusted to 1000 fluorescence units.

Oligonucleotide Density on Microspheres

To determine the number of oligonucleotides on a fully packed microsphere, microspheres were coated with 1:1 ratios of various concentrations of fluorescent probe and upstream oliogonucleotide. A series of tubes containing 400 µl equimolar fluorescent probe and upstream oligonucleotide with each of the two oligonucleotides at concentrations from 50 nM to 0.1 nM were prepared by diluting into PBST. From these tubes, 200 µl of each coating solution was coated on to $5.66 \times 10^5$ streptavidin microspheres by incubating overnight at room temperature on a rotary platform. Microspheres were pelleted by centrifugation, and the supernatant of each sample was recovered. Fluorescence signals from the 200 µl supernatant and the 200 µl remaining from the original coating solution were measured by fluorometry. From the measured fluorescence signals of the coating solutions before and after coating, the amount of microsphere-bound fluorescent probe was calculated. Multiplying the fraction bound by the concentration of fluorescent probe oligonucleotide in the coating solution yields the maximum amount of probe that can bind to the microspheres, which is about 5 pmol/$cm^2$. As the coating solution contained an equal number of upstream oligonucleotides, the total occupancy of the microspheres is 10 pmol/$cm^2$. This corresponds to 2 million oligonucleotides per microsphere or 60,000 per $\mu m^2$.

Linearity of Fluorescence

To verify that microsphere fluorescence increases linearly with the number of cleaved probes, a set of microspheres was prepared with known concentrations of fluorescent probe, quenched probe (containing both fluorescein and dabcyl quencher), and upstream oligonucleotide. Ratios of the three oligonucleotides were chosen to simulate from 0 to 25% cleavage of the probes on the microsphere surface. In 200-µl volume coating reactions, $5.66 \times 10^5$ streptavidin microspheres were rotated overnight with the various concentrations of the three oligonucleotides. Coated microspheres were centrifuged, resuspended in 500 µl of 0.2 M carbonate buffer, and analyzed by flow cytometry. A minimum of 10,000 microspheres was counted per sample. Microsphere-sized objects were gated on forward scatter, and median fluorescence values for each sample's microspheres were determined and then normalized to fluorescence of the calibration particles. As the number of oligonucleotides that can bind per $\mu m^2$ at the given concentration had been determined, it was possible to calculate the number of unquenched probes bound per $\mu m^2$. When the relative fluorescence of each sample was plotted against the number of fluorescent probe molecules on the microsphere surface, the plot was linear, with a correlation coefficient of 0.999206.

Analysis of Assay Data

Threshold values for assays with each type of microsphere were based on signals from control reactions where Cys or Arg microspheres were incubated with all reaction components except genomic DNA. For Arg microspheres, the mean for 8 control reactions was 353 RFU, while the mean for 6 control reactions with Cys microspheres was 287 relative fluorescence unit (RFU). Threshold values were therefore arbitrarily set at 400 RFU for reactions with Arg microspheres and at 300 RFU for reactions with Cys microspheres.

Tests with two genomic DNA samples (samples 2 and 10) yielded ordered pairs where neither of the two signals exceeded its corresponding threshold value. At the other extreme, anomalously high values (>1300 RFU) for both signals occurred with one DNA sample (sample 3). In both cases, these values were discarded, and the DNA samples were retested. For another genomic DNA sample (sample 6), tests yielded disparate values for replicates within the same thermocycler run. The discrepant ordered pairs were discarded, and that genomic DNA sample was retested. Data from the anomalous low-value, high-value, and discrepant-value ordered pairs mentioned above are not plotted in FIGS. 8 or 9, while data from retested samples are plotted in FIGS. 8 and 9.

Example 8

Probe and Upstream Oligonucleotides with Uniform Length Spacers Exhibit Higher Signal Invasive cleavage reaction performance experiments were conducted in the ApoE system (See, Example 3) using 5, 10, or 20 unit hexaethylene gycol spacers, respectively, to attach upstream oligonucleotides to a solid support, combined with 10 unit hexaethylene gycol spacers used to attach probe oligonucleotides.

Figure 10B:
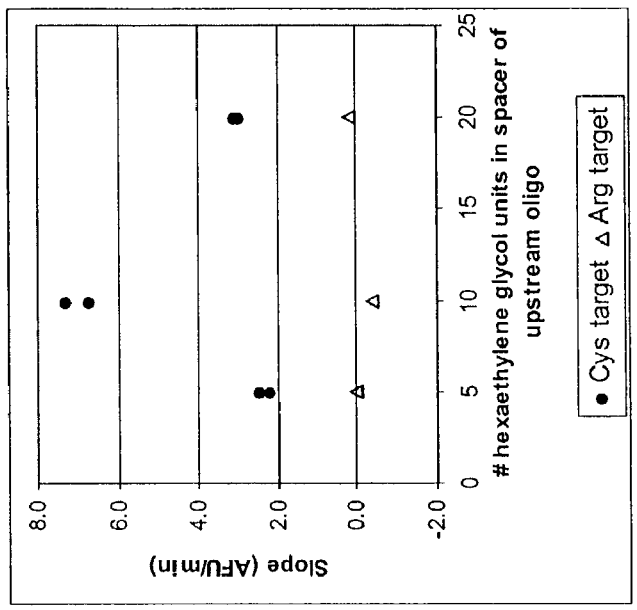
FIGS. 10A-B show graph plotting data of solid-phase ApoE reactions with varying length upstream oligonucleotide tethers.
Figure 10A:
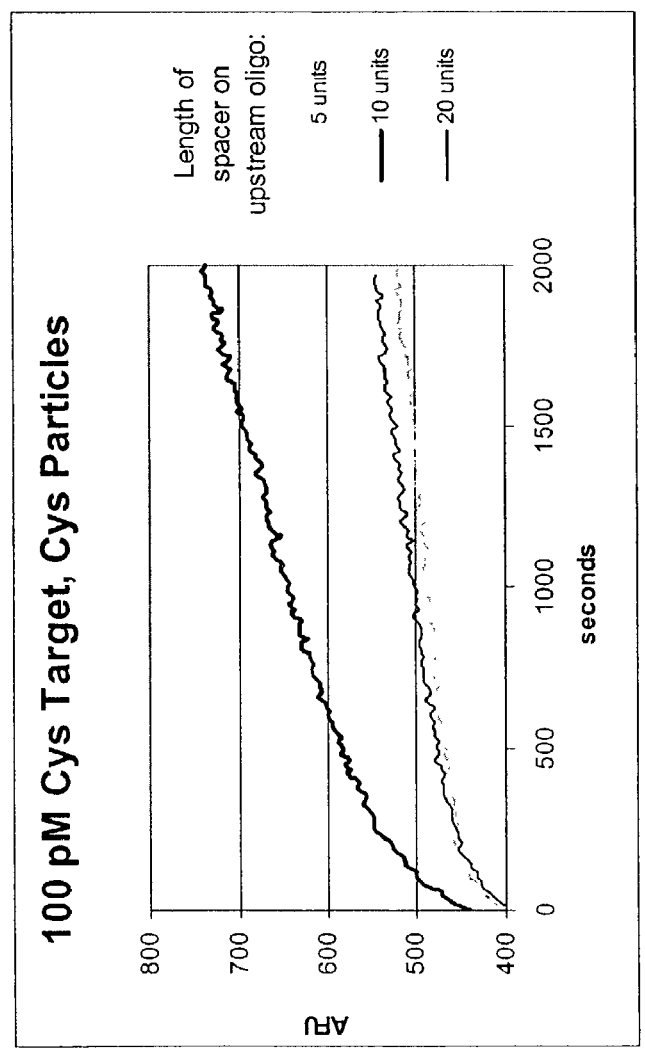

FIGS. 10A-B summarizes the results from experiments conducted to compare invasive cleavage reaction performance using various lengths of upstream oligonucleotide tethers (i.e., hexaethylene gycol spacers) combined with 10 unit probe oligonucleotide tethers. The graph in FIG. 10A plots signal generation versus time. In FIG. 10A, data was generated from reactions including 100 pM Cys target and Cys particles. Data in FIG. 10A show 5 unit (light gray) and 20 (thin black) unit upstream oligonucleotide tethers, respectively, combined with 10 unit probe oligonucleotide tethers, produced less signal than invasive cleavage reactions conducted with uniform 10 unit upstream and probe oligonucleotide tethers.

The graph in FIG. 10B plots slope (AFU/time [in min.]) versus the number of hexaethylene glycol units in the upstream oligonucleotide spacer. The data in FIG. 10B shows an increasing slope in experiments conducted with 10 unit upstream oligonucleotide tethers as compared to 5 and 20 unit upstream oligonucleotide tethers for the Cys target (filled circles). The slope of the Arg target data is nearly flat (hollow triangles).

The data in FIGS. 10A and 10B shows that, in the experiments conducted, particles having both upstream and probe oligonucleotides 10-unit hexaethylene gycol spacers showed good assay performance.

Invasive cleavage reactions were conducted in: 200 μl volumes at 54° C. for 35 min (rocked continuously); 10 ng/μl enzyme concentration; 30:1 probe:upstream oligo; 20 μg (~57,000,000) particles/assay; 210:1 target:particle; and 0.8 μm particle size. Measurements were conducted using a fluorometer as described above.

Example 9

Probe and Upstream Oligonucleotides with Uniformly Increasing Length Spacers Exhibit Higher Signal Experiments measuring signal generation in invasive cleavage reactions conducted in the ApoE system (See, Example 3) demonstrate that uniformly increasing the lengths of both probe and upstream oligonucleotides increases signal production.

Figure 11:
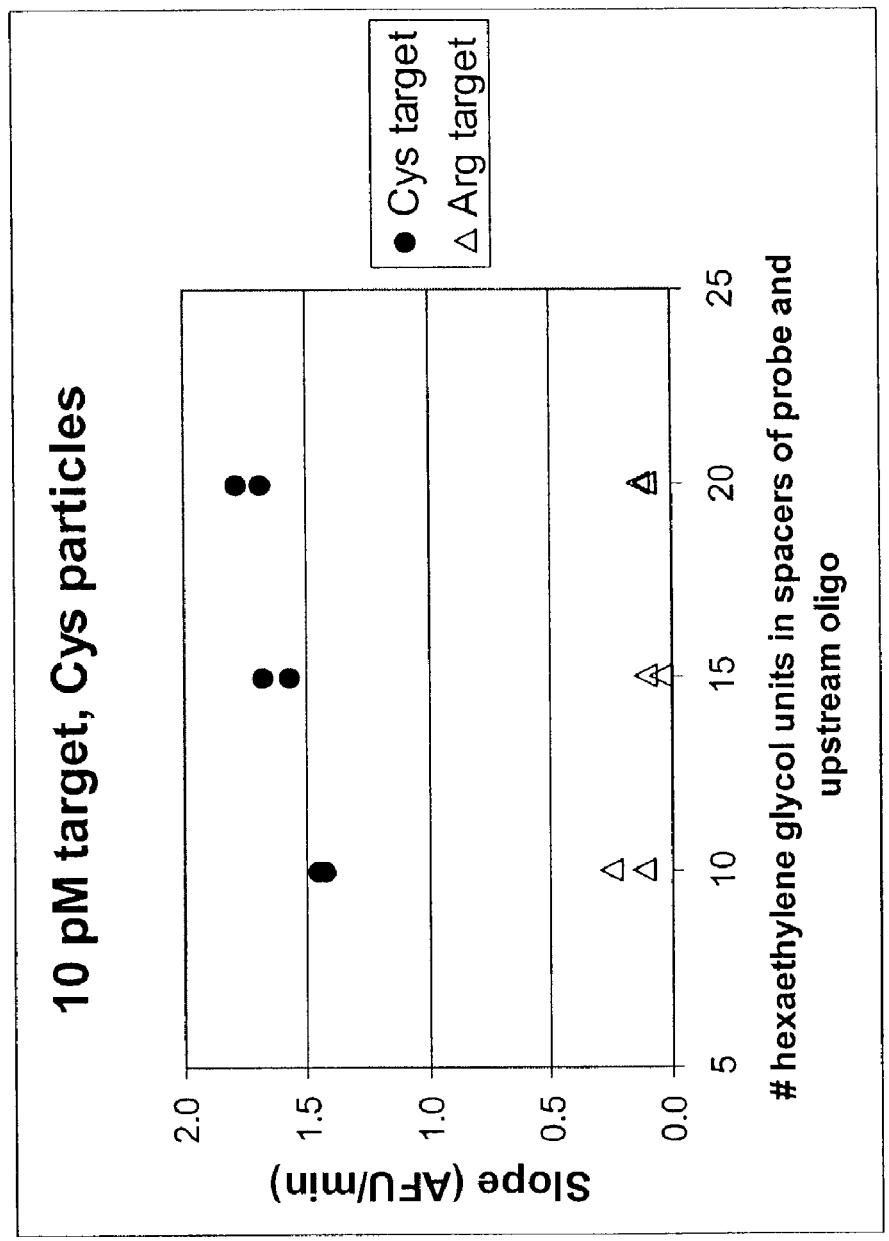
FIG. 11 shows a graph plotting data of solid-phase ApoE reactions with varying length probe and upstream oligonucleotide tethers.

The graph in FIG. 11 plots slope (AFU/time [in min.]) versus the number of hexaethylene glycol units in both the probe and upstream oligonucleotide tethers. The data in FIG. 11 shows increasing slope in experiments conducted with progressively longer (i.e., 10, 15, or 20 unit hexaethylene glycol spacers) probe and upstream oligonucleotide tethers for Cys target (filled circles). The slope of the Arg target data is nearly flat (hollow triangles).

The data in FIG. 11 show that, in the experiments conducted, particles having both upstream and probe oligonucleotides tethered with uniform hexaethylene glycol spacers increase assay performance.

Invasive cleavage reactions were conducted in: 200 μl volumes at 54° C. for 30 min (rocked continuously); 10 ng/μl enzyme concentration; 30:1 probe:upstream oligo; 15 μg (~850,000) particles/assay; 1,400:1 target:particle; and 3.2 μm particle size. Measurements were conducted using a fluorometer as described above.

Example 10

Upstream Oligonucleotide Tm

Experiments were conducted to examine the effects of upstream oligonucleotides having standard or reduced Tm points on invasive cleavage reaction performance. Briefly, particles were coated with probe oligonucleotides and upstream oligonucleotides as shown in Table 3 below.

| ApoE Upstream Olionucleotides | Tm | Length |
|---|---|---|
| Full-length; 5'-Biotin-(spacer)-Ccccggcctggtacactgccaggct-3' SEQ ID NO: 16 | 83.9 | 24 |
| Tm ~5 degrees higher than probe; 5'-Biotin-(spacer)-ggtacactgccaggct-3' SEQ ID NO: 17 | 65.4 | 15 |
| Tm ~equal to probe; 5'-Biotin-(spacer)-gtacactgccaggct-3' SEQ ID NO: 18 | 61.8 | 14 |
| Tm ~5 degrees lower than probe; 5'-Biotin-(spacer)-cactgccaggct-3' SEQ ID NO: 19 | 55.7 | 11 |

Figure 12:
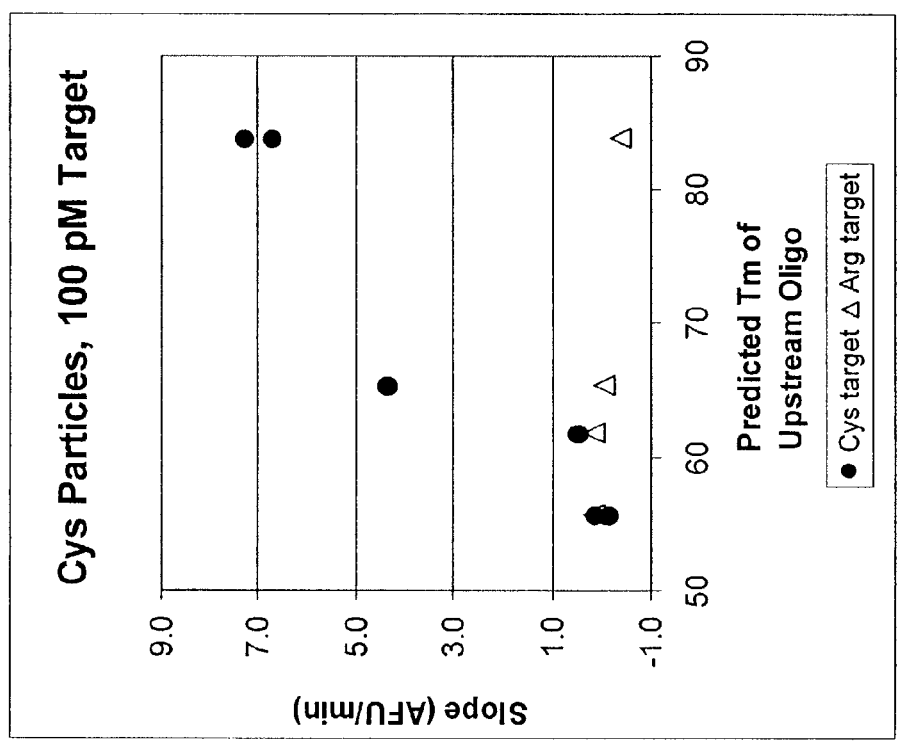
FIG. 12 shows a graph plotting data of solid-phase ApoE reactions with particles having varying upstream oligonucleotide Tm points.

Data for these experiments is shown in FIG. 12. The graph shown in FIG. 12 plots slope (AFU/time [min]) versus the predicted Tm of the upstream oligonucleotide. Particles with standard (i.e., high Tm) upstream oligonucleotides demonstrated better assay performance (signal generation) than particles with lower Tm upstream oligonucleotides.

Invasive cleavage reactions were conducted in: 200 μl volumes at 54° C. for 30 min (rocked continuously); 10 ng/μl enzyme concentration; 30:1 probe:upstream oligo; 20 μg (~57,000,000) particles/assay; 210:1 target:particle; 10 unit oligonucleotide spacers; and 0.8 μm particle size. Measurements were conducted using a fluorometer as described above.

Example 11

Figure 13A:
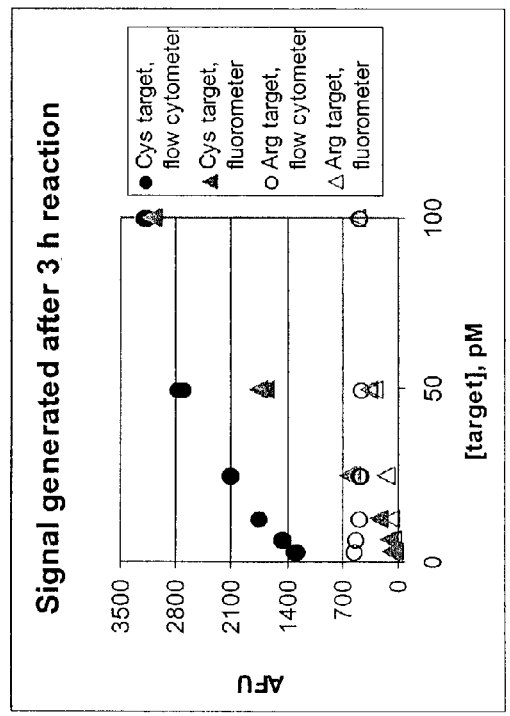
FIGS. 13A-B show graphs plotting data of solid-phase ApoE reactions.
Figure 13B:
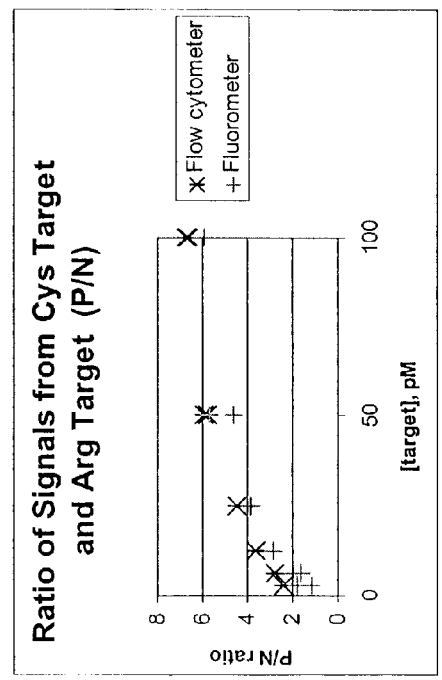

Flow Cytometer Analysis of Solid-phase Invasive Cleavage Reaction Assay Provides Endpoint Data for Individual Particles Experiments were conducted to provide endpoint data for individual particles as follows. Six 2-fold dilutions of target (100, 50, 25, 13, 6.3, 3.1 pM) were tested, respectively, with six 2-fold dilutions of Cys particles (195, 98, 49, 24, 12, 6 μg/ml), in the ApoE system (See, Example 4). Signal measurements were conducted by fluorometer (AFU/tube) and flow cytometer (AFU/particle). As is shown in FIGS. 13A and 13B, fluorometer and flow cytometer signal measurements yielded similar P/N ratios. Positive to negative ratios (P/N) for fluorometer data were calculated by averaging endpoint fluorometer signals for replicate reactions of Cys target with Cys microspheres (P) and dividing that average by the average of endpoint fluorometer signals for replicate reactions of Arg target with Cys microspheres (N).

The graph shown in FIG. 13A plots AFU (arbitrary fluorescence units) versus target (Cys or Arg) pM after a 3 hr reaction. The data in FIG. 13A shows a steadily increasing AFU measurement for Cys target versus target concentration (pM). FIG. 13B shows a plot of signal from Cys targets (triangles) and Arg targets (circles) measure using both flow cytometry (filed shapes) and fluorometric (hollow shapes)

methodologies as described above. The data in FIG. 13B show that flow cytometric and fluorometric measurements yielded similar P/N ratios.

Invasive cleavage reactions were conducted in: 200 µl-6.4 ml reaction volumes at 54° C. for 3 hr (rocked continuously); 10 ng/µl enzyme concentration; 30:1 probe:upstream oligo; 38 µg (~2,200,000) particles/assay; 5,600:1 target:particle; 10 unit oligonucleotide spacers; and 3.2 µm particle size. Measurements were conducted using both a fluorometer and a flow cytometer as described above.

Example 12

Increasing the Amount of Upstream Oligonucleotides Per Particle Improves P/N Ratios for Solid-phase Invasive Cleavage Reactions Increasing amounts of upstream oligonucleotides per particle were investigated to determine affects on P/N ratios in solid-phase invasive cleavage reactions in an ApoE system (See, Example 4). Briefly, the P/N ratios of particles coated with probe and upstream oligonucleotides at the following ratios: 1:1; 12:1; 18:1; 24:1; and 30:1 were determined.

Figure 14:
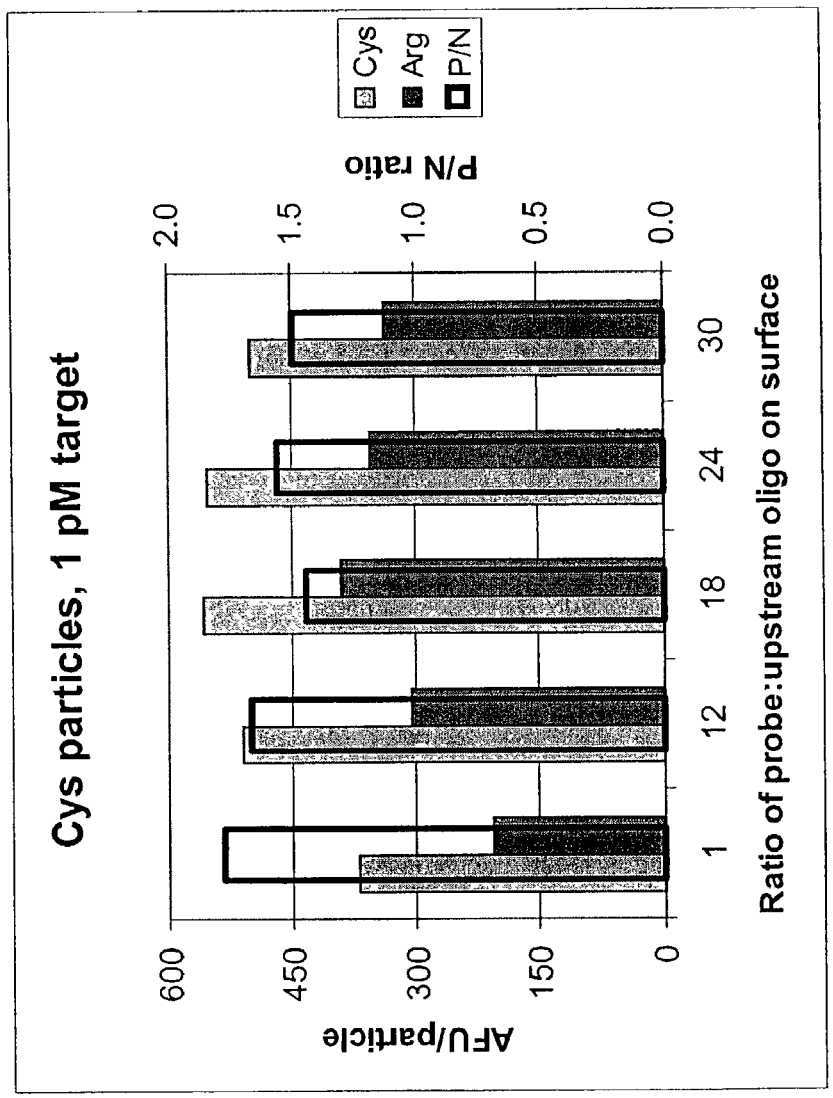
FIG. 14 shows a graph plotting data of solid-phase ApoE reactions with increasing amounts of upstream oligonucleotides per particle.

FIG. 14 plots the ratio of AFU to particles versus the ratio of probe to upstream oligonucleotides on the particle surface versus P/N ratio. The data in FIG. 14 show that the best P/N ratio (hollow box) was obtained at a 1:1 ratio of probe to upstream oligonucleotide.

Invasive cleavage reactions were conducted in: 200 µl reaction volume at 54° C. overnight (rocked continuously); 10 ng/µl enzyme concentration; probe:upstream oligo varied [1:1; 12:1; 18:1; 24:1; and 30:1]; 3.8 µg (~200,000) particles/assay; 5,60:1 target:particle; 10 unit oligonucleotide spacers; and 3.2 µm particle size. Measurements were conducted using a flow cytometer as described above.

Example 13

Invasive Cleavage Reactions at Low Particle Concentration Favor a 1:1 Ratio of Probe to Upstream Oligonucleotide on the Particle Surface Experiments were conducted to determine the optimal probe to upstream oligonucleotide ratio for invasive cleavage reactions using low particle concentrations in the ApoE system described above (See, Example 4). In these experiments, the number of particles per assay was reduced 12-fold from those in Experiment 12.

Figure 15:
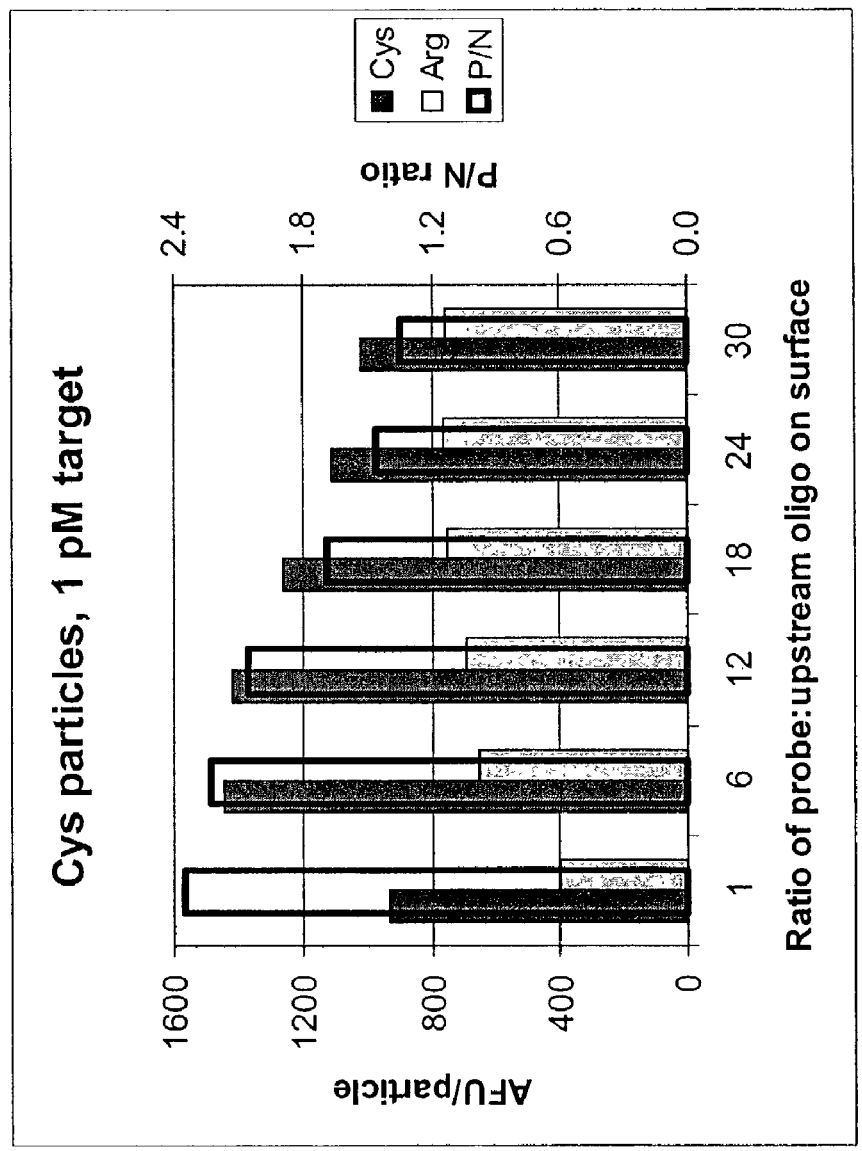
FIG. 15 shows a graph plotting data of solid-phase ApoE reactions with 1:1 probe to upstream oligonucleotide ratios and low particle concentrations.

FIG. 15 plots the ratio of AFU to particles versus the ratio of probe to upstream oligonucleotides on the particle surface versus P/N ratio. The data shown in FIG. 15 shows that a 1:1 probe to upstream oligonucleotide ratio produced the best P/N ratio (hollow box) at the concentrations tested (i.e., 1:1; 12:1; 18:1; 24:1; and 30:1. Particles coated with equal concentrations of probe and upstream oligo produced the best P/N ratios.

Invasive cleavage reactions were conducted in: 200 µl reaction volume at 54° C. overnight (rocked continuously); 10 ng/µl enzyme concentration; probe:upstream oligo varied [1:1; 12:1; 18:1; 24:1; and 30:1]; 300 ng (~17,000) particles/assay; 7,000:1 target:particle; 10 unit oligonucleotide spacers; and 3.2 µm particle size. Measurements were conducted using a flow cytometer as described above.

Example 14

Low Target Concentration Solid-phase Invasive Cleavage Reactions

Experiments were conducted to explore solid-phase cleavage reaction performance at low concentrations of target oligonucleotides in the ApoE system described above (See, Example 4).

Figure 16A:
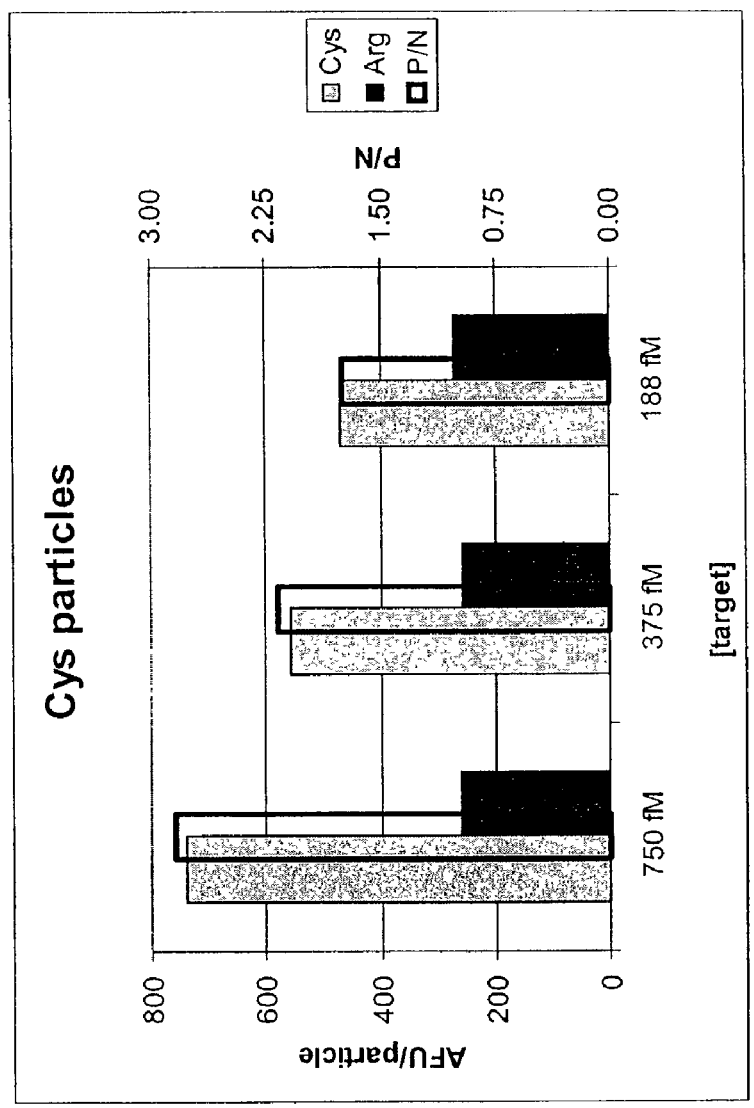
FIGS. 16A-B show graphs plotting data of solid-phase ApoE reactions with femtomolar target oligonucleotide concentrations.
Figure 16B:
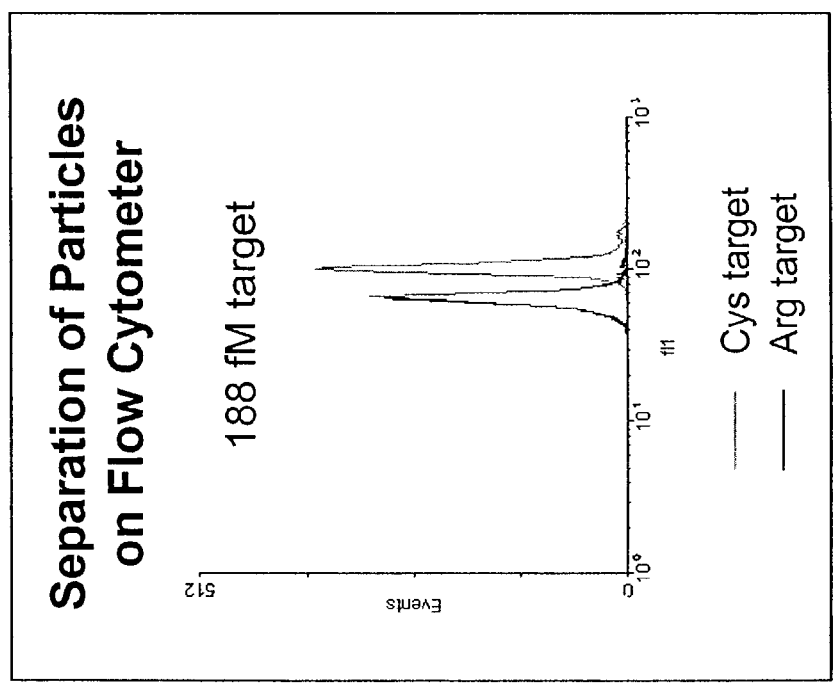

The graph in FIG. 16A plots the ratio of AFU to particles versus target oligonucleotide concentration (in fM) versus P:N ratio. The data in FIG. 16A show the solid-phase invasive cleavage reaction is capable of differentiating signals for Cys and Arg at target oligonucleotide concentrations of 188 fM. The graph in FIG. 16B shows the detection event peaks of Arg target (shown in black) and Cys target (shown in gray) for target concentration at 188 fM.

Invasive cleavage reactions were conducted in: 1.6 ml reaction volume at 54° C. overnight (rocked continuously); 1 ng/µl enzyme concentration; 1:1 probe:upstream oligo; 3 µg (~170,000) particles/assay; 426:1 (750 fM target), 213:1 (375 fN target), and 107:1 (188 fM target) target:particle; 10 unit oligonucleotide spacers; and 3.2 µm particle size. Measurements were conducted using a flow cytometer as described above.

Example 15

Solid-phase Invasive Cleavage Reactions at Low Reaction Volumes and Low Particle Numbers Experiments were conducted to explore invasive cleavage reaction performance at low particle numbers and low reaction volumes in the ApoE system (See, Example 4).

Figure 17:
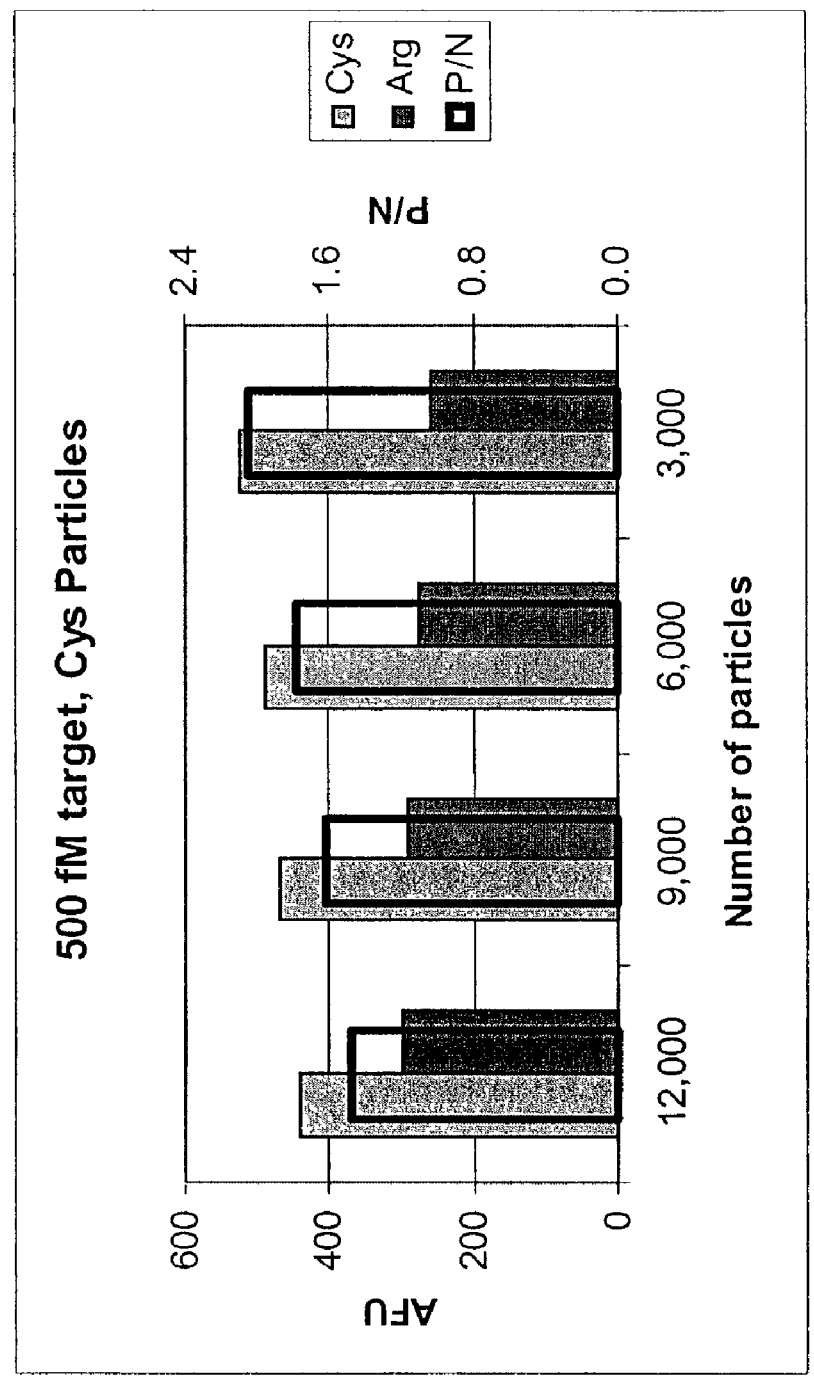
FIG. 17 shows a graph plotting data of solid-phase ApoE reactions having low reaction volumes and low particle numbers.

The graph in FIG. 17 plots AFU versus number of particles versus P:N ratio. The data show that good P:N ratios (hollow box) were obtained using as little as 3,000 particles and 500 fM of target oligonucleotides.

Invasive cleavage reactions were conducted in: 10 ml reaction volume at 54° C. overnight (rocked continuously); 1 ng/µl enzyme concentration; 1:1 probe:upstream oligo; 0.5-2 µg particles/assay; 250:1 (12,000 particles), 330:1 (9,000 particles), 500:1 (6,000 particles), and 1,000:1 (3,000 particles) target:particle; 10 unit oligonucleotide spacers; and 3.2 µm particle size. Measurements were conducted using a flow cytometer as described above.

All publications and patents mentioned in the above specification are herein incorporated by reference. Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method for detecting polymorphisms in unamplified DNA, comprising:
   a. providing:
      i. unamplified genomic DNA, wherein said unamplified genomic DNA comprises 50 micrograms or less of genomic DNA;
      ii. a microsphere;
      iii. oligonucleotides and enzymes for conducting an invasive cleavage reaction, wherein said oligonucleotides comprise a probe oligonucleotide and an upstream oligonucleotide each attached to said microsphere via a spacer molecule, wherein said spacer molecule has a length of 10 hexaethylene glycol molecules and, wherein said upstream oligonucleotide is configured to hybridize to a target sequence in a manner that overlaps with said probe oligonucleotide; and
   b. treating said unamplified genomic DNA with said oligonucleotides and enzymes under conditions such that said upstream oligonucleotide and said probe oligonucleotide hybridize to said unamplified genomic DNA such that said upstream oligonucleotide overlaps said probe oligonucleotide, and an invasive cleavage reaction occurs on said microsphere such that the presence or absence of a polymorphism in said unamplified genomic DNA is identified.

2. The method of claim 1, wherein said oligonucleotides and enzymes are configured to detect a plurality of different polymorphisms in said unamplified genomic DNA.

3. The method of claim 2, wherein said plurality of different polymorphisms comprises at least 100 different polymorphisms.

4. The method of claim 2, wherein said plurality of different polymorphisms comprises at least 1000 different polymorphisms.

5. The method of claim 2, wherein said plurality of different polymorphisms comprises at least 1,000,000 different polymorphisms.

6. The method of claim 1, wherein said treating step is carried out in a single reaction vessel.

7. The method of claim 1, wherein said oligonucleotides and enzymes are present in approximately equal concentrations.

8. The method of claim 1, wherein said treating comprises use of flow cytometry.

9. A method for detecting polymorphisms in unamplified DNA, comprising:
   a. providing:
      i. unamplified genomic DNA, wherein said unamplified genomic DNA comprises 50 micrograms or less of genomic DNA;
      ii. a solid surface;
      iii. oligonucleotides and enzymes for conducting an invasive cleavage reaction, wherein said oligonucleotides comprise a probe oligonucleotide and an upstream oligonucleotide each attached to said solid surface via a spacer molecule, wherein said spacer molecule has a length of 10 hexaethylene glycol molecules, and wherein said upstream oligonucleotide is configured to hybridize to a target sequence in a manner that overlaps with said probe oligonucleotide;
      iv. a flow cytometer;
   b. treating said unamplified genomic DNA with said oligonucleotides and enzymes under conditions such that said probe oligonucleotide and said upstream oligonucleotide hybridize to said unamplified genomic DNA such that said upstream oligonucleotide overlaps said probe oligonucleotide, and an invasive cleavage reaction, occurs on said solid surface such that a signal is generated, said signal indicating the presence or absence of said polymorphism; and
   c. detecting said signal with said flow cytometer.

* * * * *